US010675166B2

(12) United States Patent
Paulos et al.

(10) Patent No.: US 10,675,166 B2
(45) Date of Patent: *Jun. 9, 2020

(54) ADJUSTABLE BRACE ASSEMBLY AND METHODS OF USE

(71) Applicants: THE LONNIE AND SHANNON PAULOS TRUST, Salt Lake City, UT (US); Kim A. Nelson, Salt Lake City, UT (US)

(72) Inventors: Lonnie E. Paulos, Salt Lake City, UT (US); Kim A. Nelson, Salt Lake City, UT (US); Jordan Terry, Salt Lake City, UT (US)

(73) Assignee: THE LONNIE AND SHANNON PAULOS TRUST, Salt Lake City, UT (US)

( * ) Notice: Subject to any disclaimer, the term of this patent is extended or adjusted under 35 U.S.C. 154(b) by 518 days.

This patent is subject to a terminal disclaimer.

(21) Appl. No.: 15/423,851

(22) Filed: Feb. 3, 2017

(65) Prior Publication Data

US 2017/0143527 A1    May 25, 2017

Related U.S. Application Data

(63) Continuation-in-part of application No. 15/406,738, filed on Jan. 15, 2017, and a continuation-in-part of
(Continued)

(51) Int. Cl.
*A61F 5/01* (2006.01)
*A63B 21/00* (2006.01)
(Continued)

(52) U.S. Cl.
CPC ...... *A61F 5/0123* (2013.01); *A63B 21/00069* (2013.01); *A63B 21/0552* (2013.01);
(Continued)

(58) Field of Classification Search
CPC .... A61F 5/0123; A61F 5/0109; A61F 5/0125; A61F 2005/0176; A61F 5/0102;
(Continued)

(56) References Cited

U.S. PATENT DOCUMENTS 2,603,786 A     7/1953   Haines
3,669,105 A *   6/1972   Castiglia ............... A61F 5/0125
                                                            2/22
(Continued)

FOREIGN PATENT DOCUMENTS

EP            1462072        9/2004
JP            01150916       6/1989
(Continued)

OTHER PUBLICATIONS

USPTO, Nelson, Keri Jessica, U.S. Appl. No. 13/195,608, Office Action, dated, Dec. 21, 2018, 8 pages, US.
(Continued)

*Primary Examiner* — Ophelia A Hawthorne
(74) *Attorney, Agent, or Firm* — John Brooks Law LLC; John J. Brooks, III

(57) ABSTRACT

Example embodiments of the brace assembly utilize an elastic cross strap attached to mounting facilities about a joint to provide progressive resistance to the extension, flexion or other movement of body parts about the joint. In some embodiments for a knee joint, the brace assembly provides a progressive resisting force to resist hyperextension of the knee. Some embodiments of the brace assembly further comprise adjusting facilities to accommodate different joints, different size wearers of the assembly and different tension settings such as for athletes during competition. Some embodiments of the brace assembly may be used bilaterally and can be made without metal bracing to comply with the requirements of some sports.

14 Claims, 34 Drawing Sheets

Related U.S. Application Data application No. 15/195,618, filed on Jun. 28, 2016, now abandoned, said application No. 15/406,738 is a continuation of application No. 14/447,703, filed on Jul. 31, 2014, now Pat. No. 9,554,934, which is a continuation-in-part of application No. 13/188,506, filed on Jul. 22, 2011, now Pat. No. 8,808,211, and a continuation-in-part of application No. 12/993,258, filed as application No. PCT/US2009/046183 on Jun. 3, 2009, now Pat. No. 8,852,133, said application No. 14/447,703 is a continuation-in-part of application No. 13/541,796, filed on Jul. 5, 2012, now Pat. No. 9,320,634, said application No. 13/188,506 is a continuation-in-part of application No. PCT/US2009/067152, filed on Dec. 8, 2009, which is a continuation-in-part of application No. PCT/US2009/046183, filed on Jun. 3, 2009, said application No. 13/188,506 is a continuation-in-part of application No. 12/993,258, filed on Nov. 18, 2010, now Pat. No. 8,852,133, said application No. 13/541,796 is a continuation-in-part of application No. 12/993,258, filed on Nov. 18, 2010, now Pat. No. 8,852,133, which is a continuation-in-part of application No. 13/188,506, filed on Jul. 22, 2011, now Pat. No. 8,808,211, said application No. 15/195,618 is a continuation-in-part of application No. 14/447,703, filed on Jul. 31, 2014, now Pat. No. 9,554,934.

(60) Provisional application No. 62/300,131, filed on Feb. 26, 2016, provisional application No. 62/186,192, filed on Jun. 29, 2015, provisional application No. 61/864,674, filed on Aug. 12, 2013, provisional application No. 61/148,973, filed on Feb. 1, 2009, provisional application No. 61/058,555, filed on Jun. 3, 2008, provisional application No. 61/262,723, filed on Nov. 19, 2009, provisional application No. 61/263,737, filed on Nov. 23, 2009, provisional application No. 61/504,341, filed on Jul. 5, 2011, provisional application No. 61/466,909, filed on Mar. 23, 2011, provisional application No. 62/300,131, filed on Feb. 26, 2016.

(51) Int. Cl.
| | | |
|---|---|---|
| *A63B 21/055* | (2006.01) | |
| *A63B 69/00* | (2006.01) | |
| *A63B 23/04* | (2006.01) | |
| *A63B 23/12* | (2006.01) | |
| *A63B 23/035* | (2006.01) | |
| *A63B 71/12* | (2006.01) | |

(52) U.S. Cl.
CPC ...... *A63B 21/0557* (2013.01); *A63B 21/4005* (2015.10); *A63B 21/4007* (2015.10); *A63B 21/4009* (2015.10); *A63B 21/4011* (2015.10); *A63B 21/4013* (2015.10); *A63B 21/4015* (2015.10); *A63B 21/4017* (2015.10); *A63B 21/4025* (2015.10); *A63B 21/4039* (2015.10); *A63B 23/03508* (2013.01); *A63B 23/0494* (2013.01); *A63B 23/1281* (2013.01); *A63B 69/0059* (2013.01); *A61F 2005/0165* (2013.01); *A63B 21/00061* (2013.01); *A63B 21/00065* (2013.01); *A63B 2071/1258* (2013.01); *A63B 2209/10* (2013.01); *A63B 2225/09* (2013.01)

(58) Field of Classification Search
CPC .. A61F 5/01; A61F 13/08; A61F 13/00; A61F 13/00029; A61F 13/06; A61F 2007/0001; A61F 2007/0039; A61F 2007/0042; A61F 2/64; A61F 5/0193; A61F 5/3715; A61F 2005/0137; A61F 2005/0165; A61F 2005/0181; A61F 2005/0144; A61F 5/0106; A61F 2005/0158; A61F 2005/0172; A61F 2005/0139; A61F 2005/0146; A61F 2005/0148; A61F 2005/0167; A61F 2005/0179; A61F 2/68; A61F 5/0111; A61F 13/061; A61F 2002/7625; A61F 2002/7635; A61F 2005/0134; A61F 2005/0169; A61F 2005/0174; A61F 2210/0057; A61F 2250/001; A61F 5/0127; A61F 5/013; A61F 13/062; A61F 2002/6818; A61F 2002/704; A61F 2002/708; A61F 2002/74; A61F 2002/741; A61F 2002/745; A61F 2002/748; A61F 2002/764; A61F 2002/7645; A61F 2002/7655; A61F 2005/0132; A61F 2005/0153; A61F 2250/0012; A61F 2/60; A61F 2/72; A61F 5/00; A61F 5/0118; A61F 5/012; A61F 5/022; A61F 5/04; A61F 5/05; A61F 5/058; A61F 5/05841; A61F 5/0585; A61F 5/30; A61F 5/37; A61F 5/373; A61F 5/3761

See application file for complete search history.

(56) References Cited

U.S. PATENT DOCUMENTS

| | | | |
|---|---|---|---|
| 4,240,414 | A | 12/1980 | Theisler |
| 4,294,238 | A | 10/1981 | Woodford |
| 4,556,054 | A | 12/1985 | Paulseth |
| 4,702,234 | A | 10/1987 | Huntjens et al. |
| 4,817,588 | A | 4/1989 | Bledsoe |
| 4,854,308 | A * | 8/1989 | Drillio ................. A61F 5/0123 602/16 |
| 5,063,916 | A | 11/1991 | France et al. |
| 5,277,698 | A | 1/1994 | Taylor |
| 5,399,153 | A | 3/1995 | Caprio, Jr. et al. |
| 5,417,647 | A | 5/1995 | Down |
| 5,512,039 | A | 4/1996 | White |
| 5,554,105 | A * | 9/1996 | Taylor ................ A41D 13/0568 128/882 |
| 5,891,079 | A | 4/1999 | Barnes |
| 6,368,297 | B1 | 4/2002 | Smits |
| 7,198,610 | B2 | 4/2007 | Ingimundarson et al. |
| 7,871,388 | B2 | 1/2011 | Brown |
| 7,959,591 | B2 | 6/2011 | Powers et al. |
| 8,007,457 | B2 | 8/2011 | Taylor et al. |
| 8,167,829 | B2 | 5/2012 | Sterling et al. |
| 8,905,956 | B2 | 12/2014 | Waeger |
| 9,168,167 | B2 | 10/2015 | Brown |
| 9,320,634 | B2 * | 4/2016 | Paulos ................. A61F 5/0102 |
| 9,452,078 | B2 | 9/2016 | Waeger |
| 2002/0010410 | A1 | 1/2002 | Steponovich |
| 2003/0204156 | A1 | 10/2003 | Nelson et al. |
| 2003/0232701 | A1 | 12/2003 | Latella, Jr. |
| 2004/0116260 | A1 * | 6/2004 | Drennan ............... A61F 5/0193 482/124 |
| 2005/0197607 | A1 | 9/2005 | Brown |
| 2006/0000478 | A1 | 1/2006 | Taylor |
| 2006/0089583 | A1 | 4/2006 | Reinhardt |
| 2007/0219478 | A1 * | 9/2007 | Powers ................. A61F 5/0104 602/62 |
| 2008/0066272 | A1 | 3/2008 | Hammerslag et al. |
| 2008/0083055 | A1 | 4/2008 | Onda et al. |
| 2009/0062704 | A1 | 3/2009 | Brown et al. |
| 2009/0090027 | A1 | 4/2009 | Baudouin et al. |
| 2010/0069802 | A1 | 3/2010 | Motyer |
| 2010/0088803 | A1 | 4/2010 | Orloff et al. |

(56) References Cited

U.S. PATENT DOCUMENTS

| | | | |
|---|---|---|---|
| 2011/0009793 A1 | 1/2011 | Lucero et al. |
| 2011/0213283 A1 | 9/2011 | Brown |
| 2012/0316483 A1 | 12/2012 | Waeger |
| 2015/0040286 A1 | 2/2015 | Schultz et al. |
| 2015/0094634 A1 | 4/2015 | Waeger |

FOREIGN PATENT DOCUMENTS

| | | |
|---|---|---|
| KR | 100742181 | 7/2007 |
| WO | WO1988001855 | 3/1988 |
| WO | WO199400082 | 1/1994 |
| WO | WO2007020372 | 2/2007 |

OTHER PUBLICATIONS

USPTO, Hawthorne, Ophelia Althea, U.S. Appl. No. 15/406,738, Office Action dated Feb. 4, 2019, 10 pages, US.

Christopher Geiser, Kristian M. O'Connor, Jennifer E. Earl, Effects of Isolated Hip Abductor Fatigue on Frontal Plane Knee Mechanics, Marquette University e-Publications@Marquette, Health Sciences Faculty Research and Publications, College of Health Sciences, Medicine and Science in Sports and Exercise, vol. 42, No. 3, Mar. 2010, pp. 535-545.

Sue D. Barber-Westin, Stephanie T. Smith, Thomas Campbell, and Frank R. Noyes, The Drop-Jump Video ScreeningTest: Retention of Improvement in Neuromuscular Control in Female Volleyball Players, Journal of Strength and Conditioning Research 2010 National Strength and Conditioning Association, vol. 0, No. 0, Month 2010, 8 pages.

Cale A. Jacobs, Timothy L. Uhl, Carl G. Mattacola, Robet Shapiro, William S. Rayens, Hip Abductor Function and Lower Extremity Landing Kinematics: Sex Differences, Journal of Athletic Training 2007; 42 (1):76-83 by the National Athletic Trainers' Association, Inc. www.journalofathletictraining.org, 8 pages.

Gregory D. Myer, Kevin R. Ford, Joseph P. Palumbo, and Timothy E. Hewett, Neuromuscular Training Improves Performance and Lower-Extremity Biomechanics in Female Athletes, Journal of Strength and Conditioning Research, 2005, 19(1), 51-60, 2005 National Strength & Conditioning Association, 10 pages.

WIPO, Park, Se Young, International Searching Authority, International Search Report and the Written Opinion of the International Searching Authority of parent PCT Application No. PCT/US09/67152 to Lonnie E. Paulos, 9 pages, dated Jul. 26, 2010, Korea.

WIPO, Moon Song, John, International Search Report and the Written Opinion of the International Searching Authority, Korean Intellectual Property Office for PCT Application No. PCT/US2009/046183 to Lonnie E. Paulos, 11 pages, dated Jan. 18, 2010, Korea.

USPTO, Lewis, Kim M, USPTO Office Action for U.S. Appl. No. 12/993,258, 14 pages, dated Aug. 19, 2013, USA.

USPTO, Lewis, Kim M., U.S. Appl. No. 12/993,258, Final Office Action dated Feb. 4, 2014, 9 pages, US.

USPTO, Lewis, Kim M., U.S. Appl. No. 12/993,258, Notice of Allowance dated Jun. 4, 2014, 17 pages, US.

USPTO, Hawthorne, Ophelia Althea, USPTO Office Action for U.S. Appl. No. 13/188,506, 17 pages, dated Aug. 5, 2013, USA.

USPTO, Hawthorne, Ophelia Althea, USPTO Office Action for U.S. Appl. No. 13/188,506, 17 pages, dated Sep. 3, 2013, USA.

USPTO, Hawthorne, Ophelia Althea, U.S. Appl. No. 13/188,506, Final Office Action dated Jan. 15, 2014, 11 pages, US.

USPTO, Hawthorne, Ophelia Althea, USPTO, U.S. Appl. No. 13/188,506, Notice of Allowance, dated Apr. 11, 2014, 11 pages, US.

USPTO, Hawthorne, Ophelia Althea, USPTO, U.S. Appl. No. 14/447,703, Non-Final Office Action, dated Dec. 14, 2015, 18 pages, USA.

USPTO, Hawthorne, Ophelia Althea, USPTO, U.S. Appl. No. 14/447,703, Final Office Action, dated Jun. 27, 2016, 12 pages, US.

USPTO, Hawthorne, Ophelia Althea, USPTO, U.S. Appl. No. 14/447,703, Notice of Allowance, dated Sep. 21, 2016, 3 pages, USA.

USPTO, Hawthorne, Ophelia, Althea, U.S. Appl. No. 13/541,796, Non-Final Office Action, dated Dec. 16, 2014, 15 pages, US.

USPTO, Hawthorne, Ophelia, Althea, U.S. Appl. No. 13/541,796, Final Office Action, dated Jul. 29, 2015, 19 pages, US.

USPTO, Hawthorne, Ophelia, Althea, U.S. Appl. No. 13/541,796, Notice of Allowance, dated Oct. 29, 2015, 13 pages, US.

Jeremy Paul Loenneke and Thomas Joseph Pujol, The Use of Occlusion Traiing to Product Muscle Hypertrophy, National Strength and Conditioning Association, Strength and Conditioning Journal, vol. 00, No. 0, 2009, USA.

Click Medical, Click Medical Solutions Guide, 2009, USA.

USPTO, Nelson, Keri Jessica, U.S. Appl. No. 15/195,618, Office Action dated Jun. 20, 2019, 10 pages, US.

USPTO, Hawthorne, Ophelia Althea, U.S. Appl. No. 15/406,738, Office Action dated Aug. 7, 2019, 17 pages, US.

USPTO, U.S. Appl. No. 15/406,738, Office Action dated Feb. 5, 2020, 17 pages.

\* cited by examiner

FIG. 20D
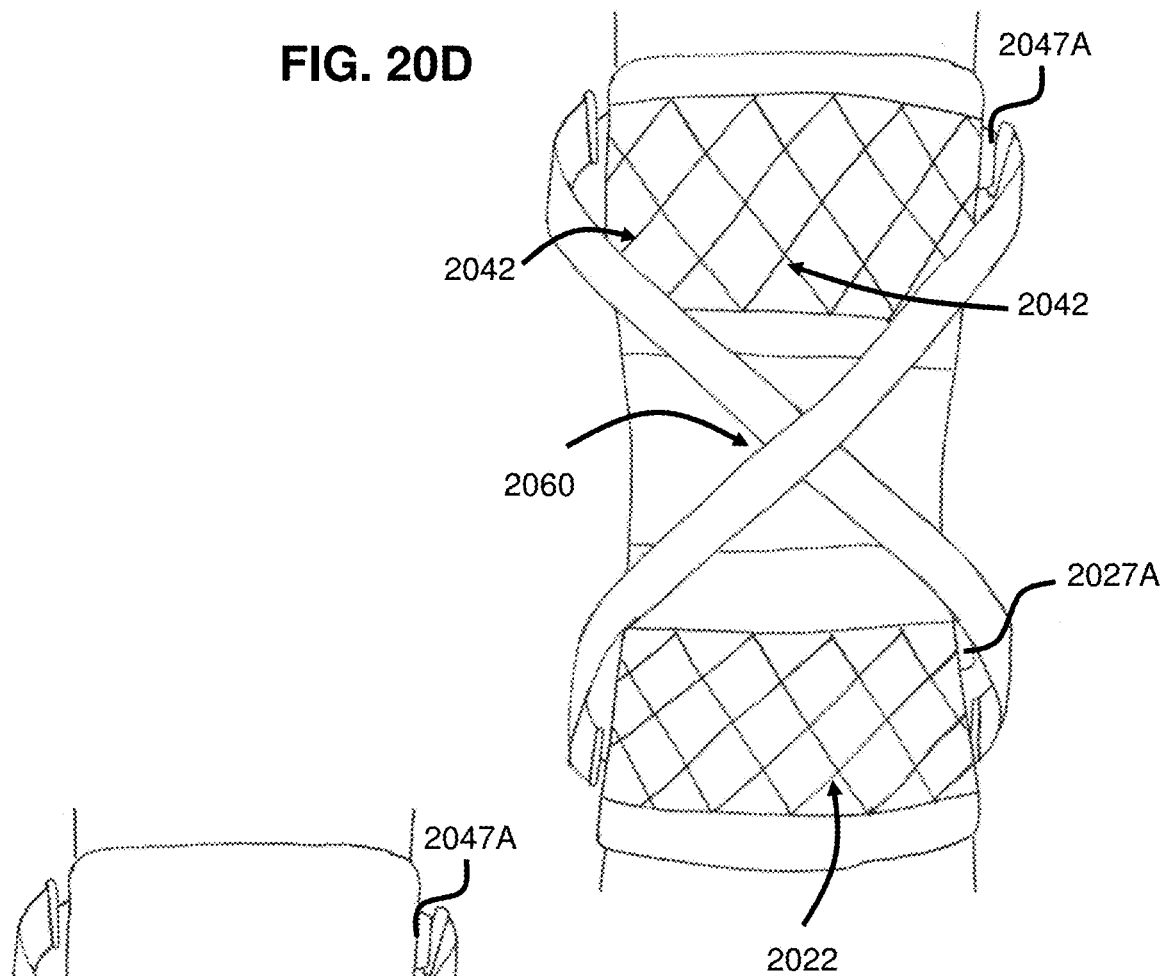
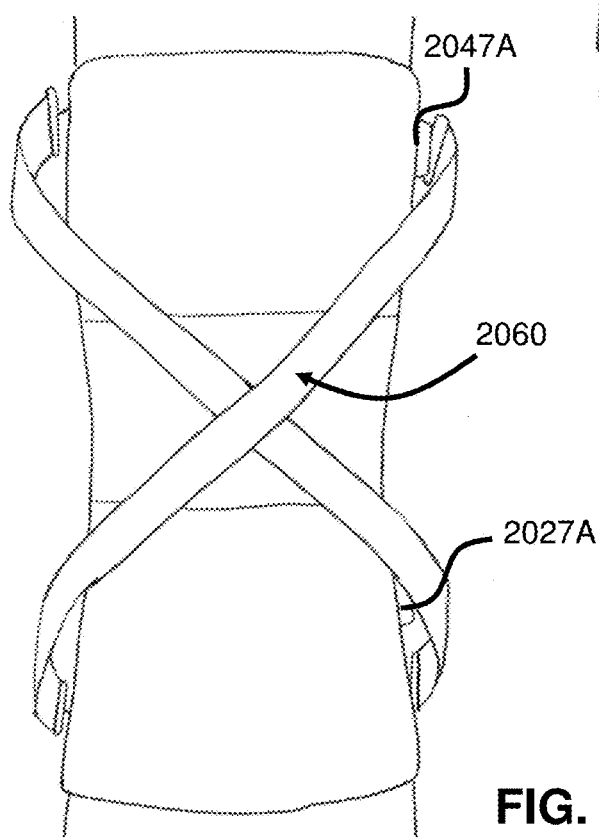
FIG. 20E

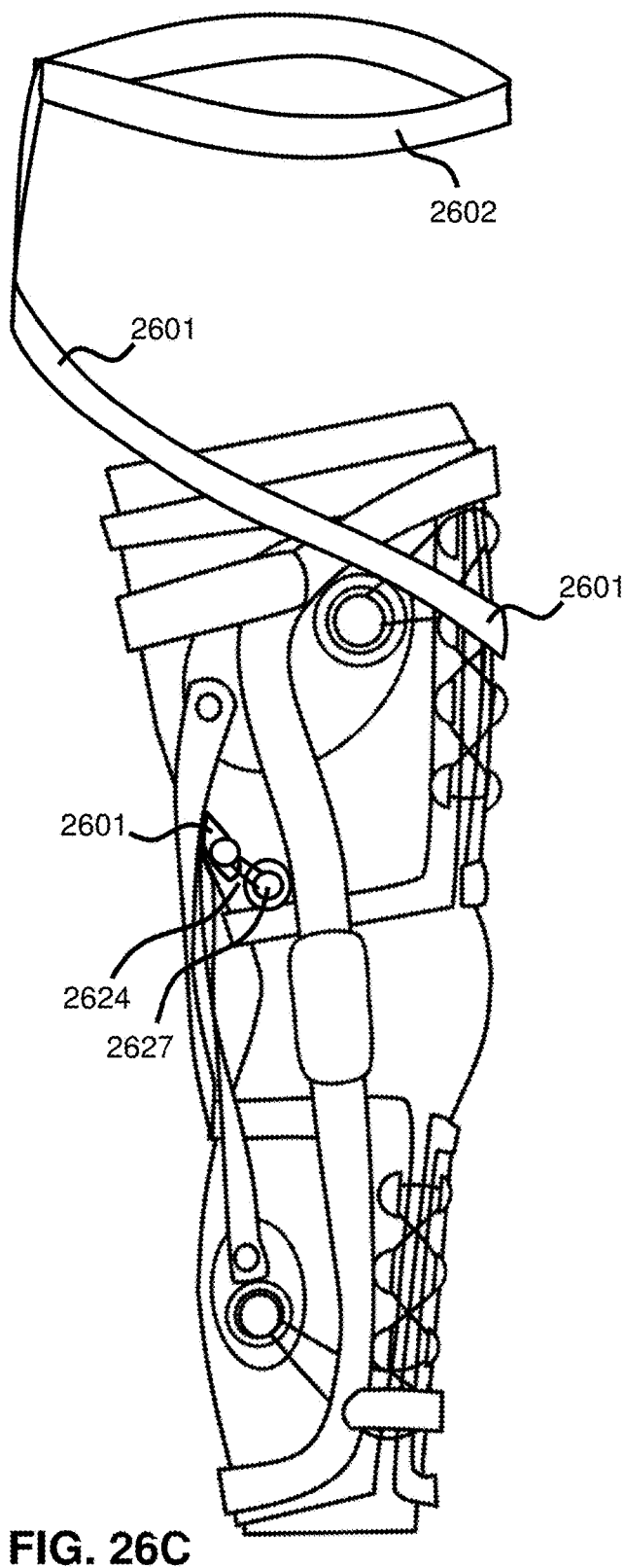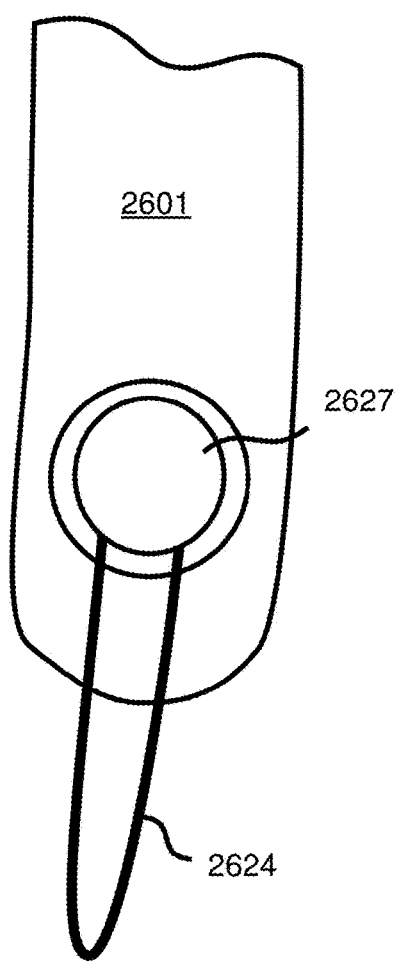
FIG. 26C
FIG. 26D

ADJUSTABLE BRACE ASSEMBLY AND METHODS OF USE

CROSS-REFERENCE TO RELATED APPLICATIONS

This application is a Continuation in Part App. of U.S. patent application Ser. No. 15/406,738 filed Jan. 15, 2017; this application also claims benefit of U.S. Pat. App. No. 62/300,131 filed Feb. 26, 2016; this application is also a Continuation in Part App. of U.S. patent application Ser. No. 15/195,618 filed Jun. 26, 2016; U.S. patent application Ser. No. 15/406,738 is a Continuation of U.S. patent application Ser. No. 14/447,703 filed Jul. 31, 2014 now U.S. Pat. No. 9,554,934 issued Jan. 31, 2017; U.S. patent application Ser. No. 15/195,618 claims benefit of U.S. Pat. App. No. 62/186,192 filed Jun. 29, 2015; U.S. patent application Ser. No. 15/195,618 also claims benefit of U.S. Pat. App. No. 62/300,131 filed Feb. 26, 2016; U.S. patent application Ser. No. 15/195,618 is also a Continuation in Part App. of U.S. patent application Ser. No. 14/447,703; U.S. patent application Ser. No. 14/447,703 claims benefit of U.S. Pat. App. No. 61/864,674 filed Aug. 12, 2013; U.S. patent application Ser. No. 14/447,703 is also a Continuation in Part App. of U.S. patent application Ser. No. 12/993,258 filed Nov. 18, 2010 now U.S. Pat. No. 8,852,133 issued Oct. 7, 2014; U.S. patent application Ser. No. 14/447,703 is also a Continuation in Part App. of U.S. patent application Ser. No. 13/188,506 filed Jul. 22, 2011 now U.S. Pat. No. 8,808,211 issued Aug. 19, 2014; U.S. patent application Ser. No. 14/447,703 is also a Continuation in Part App. of U.S. patent application Ser. No. 13/541,796 filed Jul. 5, 2012 now U.S. Pat. No. 9,320,634 issued Apr. 26, 2016; U.S. patent application Ser. No. 12/993,258 is the U.S. National Stage App. of International App. No. PCT/US09/46183 filed Jun. 3, 2009; U.S. patent application Ser. No. 13/188,506 claims benefit of U.S. Pat. App. No. 61/466,909 filed Mar. 23, 2011; U.S. patent application Ser. No. 12/188,506 is also a Continuation in Part App. of International App. No. PCT/US09/67152 filed Dec. 8, 2009; U.S. patent application Ser. No. 12/188,506 is also a Continuation in Part App. of U.S. patent application Ser. No. 12/993,258 filed Nov. 18, 2010; U.S. patent application Ser. No. 13/541,796 claims benefit of U.S. Pat. App. No. 61/504,341 filed Jul. 5, 2011; U.S. patent application Ser. No. 13/541,796 is also a Continuation in Part App. of U.S. patent application Ser. No. 13/188,506 filed Jul. 22, 2011 now U.S. Pat. No. 8,808,211 issued Aug. 19, 2014; U.S. patent application Ser. No. 13/541,796 is also a Continuation in Part App. of U.S. patent application Ser. No. 12/993,258 filed Nov. 18, 2010; International App. No. PCT/US09/67152 claims benefit of U.S. Pat. App. No. 61/262,723 filed Nov. 19, 2009; International App. No. PCT/US09/67152 also claims benefit of U.S. Pat. App. No. 61/263,737 filed Nov. 23, 2009; International App. No. PCT/US09/67152 is also a Continuation in Part App. of International App. No. PCT/US09/46183 filed Jun. 3, 2009; International App. No. PCT/US09/46183 claims benefit of U.S. Pat. App. No. 61/058,555 filed Jun. 3, 2008; International App. No. PCT/US09/46183 also claims benefit of U.S. Pat. App. No. 61/148,973 filed Feb. 1, 2009; and this application incorporates by reference all of the above referenced applications in their entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Lonnie E. Paulos, Kim A. Nelson, Jordan Terry and The Lonnie and Shannon Paulos Trust (as Amended and Restated) F/K/A The James Dizikis Trust, Dated Feb. 26, 2008.

REFERENCE TO SEQUENCE LISTING, A TABLE, OR A COMPUTER PROGRAM LISTING COMPACT DISC APPENDIX

Not Applicable

BACKGROUND OF THE INVENTION

Field of the Invention

Embodiments of the present invention relate to joint braces that can help prevent the hyperextension, flexion or undesirable movement of a joint, and more specifically relates to brace assemblies and methods utilizing adjusting facilities to adjust the force of brace elements on a body or the joint.

Background

Braces are often utilized to support joints when damage, deformation, surgery or the like has caused the joint to be instable. Sports, physical labor and everyday physical movement can create strains and injuries to joints such as the shoulder, elbow, back, wrist, ankle and knee. Specific to the knee, most of the running, jumping, cutting or twisting sports today have the risk of damaging the knee. These injuries frequently involve a tearing the ACL in the knee. Many injures to the knee joint have a mechanism of injury of hyperextension in which the ACL is stretched or torn. Many methods have been employed to prevent this action to the knee and prevent the injury to the ACL. Taping techniques as well as rigid braces have been designed to prevent this condition.

One common method of treatment and prevention for these injures today is the use of the rigid braces. Common to most, if not all, of these devises for use on the knee are, adjustable metal hinges on the medial and lateral side of the knee. Rigid arms on each side connect the hinges to curved thigh and calf pieces or cuffs. A series of Velcro straps attached to these rigid side pieces then wrap around the leg to mount and hold them in place with the cuffs and the hinges. Adjusting the hinge from allowing extension or hyperextension blocks the knee from moving into to these positions quite well.

With respect to these rigid braces however, many sports have rules in which players cannot have any metal or rigid devices on any part of their body to compete due to metal or hard structures that may cause injury to other players. One of these sports is soccer, which is also one of the most popular sports in the world. Additionally, with the introduction of bracing both knees for prevention of injury, the bracing must have a very low profile on the knees to prevent the braces from catching against each other during competition.

Another technique of treating and preventing joint injuries includes taping techniques. While reinforcing joint strength, taping typically does not involve rigid braces that cause problems with sporting rules.

Prior art embodiments of braces having strap elements that cross posterior to the knee joint include U.S. Pat. No. 4,817,588 filed on Jul. 1, 1987 to Gary Bledsoe (Bledsoe) and U.S. Pat. No. 6,368,297 filed on Oct. 22, 1999 to Jan F.

A. Smits (Smits) both of which are incorporated by reference in their entirety. Bledsoe discloses a restraining strap network positioned entirely behind the knee that has to cooperate with additional brace elements including hinges and connecting means to connect the brace elements to the wearer's leg. Bledsoe does not disclose embodiments of the strap network extending anterior to the limbs about the joint. Smits discloses a brace having a strap that crosses at the back of the knee that like Bledsoe is entirely behind the knee and has to cooperate with other brace elements. Smits also specifically uses stop portions in a hinge to limit extension of the brace elements. Smits does not disclose limiting extension of the brace with the strap.

SUMMARY OF THE INVENTION

The following summary is included only to introduce some concepts discussed in the Detailed Description below. This summary is not comprehensive and is not intended to delineate the scope of protectable subject matter.

In some example embodiments, a brace assembly is provided for use by a wearer, the brace assembly comprising an upper mounting facility operably coupled to a lower mounting facility and a training strap. In some embodiments, the training strap comprises an upper training strap mounting portion, a lower training strap mounting portion coupled to the upper mounting facility, and an elastic training strap portion configured to provide a change in a resistance force on the upper training strap mounting portion and the lower training strap mounting portion when one of the upper training strap mounting portion or the lower training strap mounting portion is moved from a first position to a second position relative to the other training strap mounting portion whereby the change in the resistance force affects the neuromuscular training of a body portion. In some embodiments, one of the upper training strap mounting portion or the lower training strap mounting portion further comprises an adjusting facility whereby the adjusting facility is configured to adjust the resistance force provided by the training strap. In some embodiments, the adjusting facility comprises an attachment point of the training strap to the upper mounting facility. In some embodiments, the adjusting facility comprises a cable and a tightening mechanism configured to operably couple with the training strap. In some embodiments, the tightening mechanism operates as a ratchet to shorten an effective length of the cable and the training strap.

In some embodiments, the brace assembly further comprises a patella stabilizer operably coupled to an upper attachment point on the upper mounting facility and a lower attachment point on the lower mounting facility. In some embodiments, the patella stabilizer further comprises an adjusting facility.

In some example embodiments, the brace assembly further comprises an elastic cross strap attached to mounting facilities about a joint to limit the extension of limbs about the joint. The cross strap may have elastic properties that allow it to provide progressive resistance as the strap is stretched. The elastic cross strap assembly is positioned from a cross origin behind or in the fossa of the joint to attachment points on mounting facilities on either side of the joint such that the assembly provides an opposing tensile force that limits the extension of the mounting facilities and the limbs about a joint. In some embodiments, the brace assembly further comprises an upper mounting facility and a lower mounting facility, at least one elastic cross strap coupled to the upper mounting facility and lower mounting facility. In some embodiments, one of the upper mounting facility or the lower mounting facility further comprises an adjusting facility whereby the adjusting facility is configured to adjust the resistance force provided by the at least one elastic cross strap. In some embodiments, the adjusting facility comprises an attachment point of the elastic cross strap to the upper mounting facility or the lower mounting facility. In some embodiments, the adjusting facility comprises a cable and a tightening mechanism configured to operably couple with the at least one elastic cross strap.

In some embodiments, one of the upper mounting facility or the lower mounting facility comprises an adjusting facility whereby the adjusting facility is configured to adjust an inside radius of the upper mounting facility or the lower mounting facility.

In some embodiments, the adjusting facility comprises a cable and a tightening mechanism whereby the tightening mechanism operates as a ratchet to shorten an effective length of the cable.

In some embodiments, the resistance force provided by the training strap or the elastic cross strap is a progressive resistance force. In some embodiments, the resistance force is a configurable resistance force. In some embodiments, the resistance force is provided by the elastic training strap portion or the cross strap comprising a composite of tensile elements. In some embodiments, the composite of tensile elements comprises a first tensile element having a first tensile strength and a first resting length and a second tensile element having a second tensile strength greater than the first tensile strength and a second resting length longer than the first resting length whereby a first resistance force is provided through a first stretch range up to the second resting length and a second resistance force is provided in a second stretch range beyond the second resting length.

In some embodiments, the resistance force is a configurable resistance force provided by the training strap or the elastic cross strap being one from a group consisting of: the training strap or the elastic cross strap having one of a plurality of different lengths, the training strap or the elastic cross strap having one of a plurality of different tensile elements, the training strap or the elastic cross strap comprising one of a plurality of elastic materials having different tensile properties, the training strap or the elastic cross strap comprising an adjustable length, the training strap or the elastic cross strap having a plurality of attachment points, and the training strap or the elastic cross strap coupling to attachment points at one of a plurality of attachment points.

In some example embodiments, a method of training a body portion of a wearer is provided, the method comprising providing an elastic training strap of a training brace assembly, the elastic training strap comprising a lower training strap mounting portion, an upper training strap mounting portion and an elastic training strap portion, positioning the lower training strap mounting portion and the upper training strap mounting portion about the body portion comprising a joint, positioning the elastic training strap portion to extend between a lower resistance point on the lower training strap mounting portion and an upper resistance point on the upper training strap mounting portion and moving one of the upper or lower resistance points relative to the other creating a change in a tensile force on the elastic training strap portion whereby the change in the tensile force affects a neuromuscular training of the body portion.

The advantages and features of the present invention will become apparent to those skilled in the art when the following description is read in conjunction with the attached drawings and the appended claims.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawing depict only typical embodiments of the invention and are not therefore to be considered to be limiting of its scope, the invention will be described and explained with additional specificity and detail through the use of the accompanying drawings in which:

FIG. 20D shows a rear/posterior view of an example embodiment of an adjustable brace assembly with adjusting facilities;

FIG. 20E shows a rear/posterior view of an example embodiment of an adjustable brace assembly with an outer sleeve;

FIG. 26C shows a side view of an example embodiment of the brace assembly with a training strap; and FIG. 26D shows an example embodiment of an end of a training strap with an adjusting facility.

DETAILED DESCRIPTION OF THE INVENTION

Figure 1A:
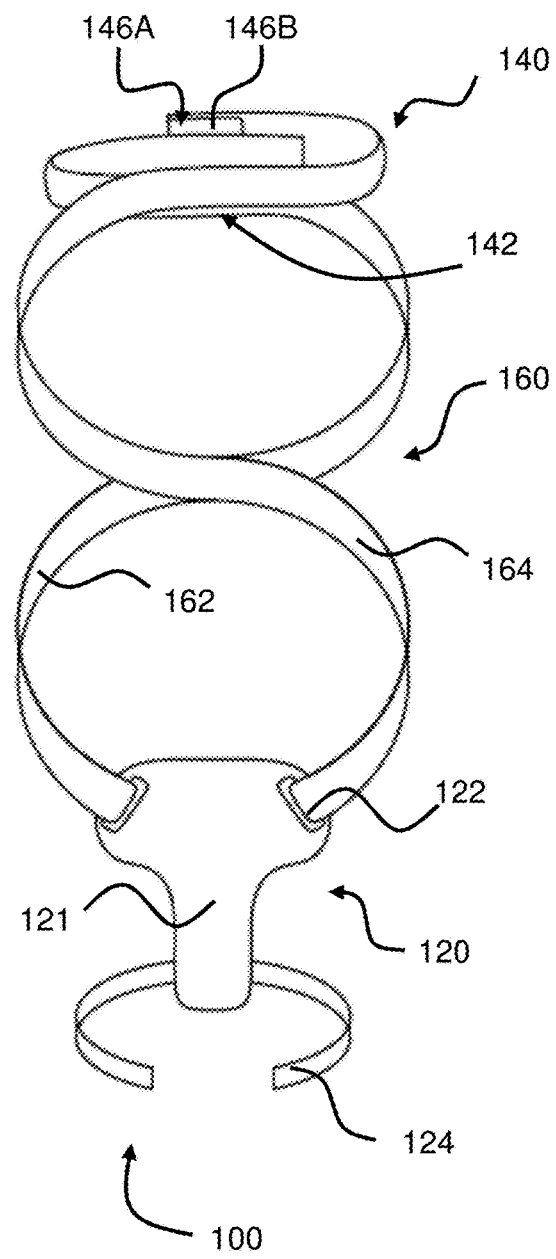
FIG. 1A illustrates a front view of one embodiment of the brace assembly showing a shin shell.

Although example embodiments are described in detail for use with knee bracing and reinforcement, it is understood that the methods and systems described can be used for similar medical situations where support of and resistance to moving joints may be needed. Examples of embodiments with other joints such as but not limited to the shoulder, elbow, back and ankle are also described and illustrated below. Notwithstanding the specific example embodiments set forth below, all such variations and modifications that would be envisioned by one of ordinary skill in the art are intended to fall within the scope of this disclosure.

Some embodiments of this elastic brace assembly comprise a non-rigid or semi-rigid brace utilizing an elastic cross strap to provide a progressive resisting force to joint movement such as hyperextension. In addition to providing a progressive resistance force, the elastic cross strap may provide neuromuscular feedback to help prevent atrophy of the wearer's muscles. Some embodiments of this brace assembly may include a flexible sleeve or other traditional brace components. Although some embodiments of the assembly do not need side hinges, metal upright stays or braces and hinges, it is contemplated that some embodiments of the brace assembly may also include these elements.

One Embodiment of the Brace Assembly:

Although it is contemplated that embodiments of the assembly can support many different types of skeletal joints such as elbows, ankle, shoulder, backs, wrists or knees, the illustrative examples below will use an embodiment directed to support a person's knee. Therefore, references to anatomical portions of the wearer's knee are for illustration purposes and not as a limitation.

Additionally, the terms upper and lower as used herein, identify different sides of a joint and are meant to include other similar terms for defining positional relationships around joints such as such as proximal and distal, front and rear, and near and far.

As used herein, the term point, for example attachment point, in addition to defining a location or position, may also be used to define an element. For example, an attachment point may also define a coupling element used to couple and/or attach elements.

Example embodiments of this new brace assembly comprise at least one elastic hyperextension cross strap, at least one upper mounting facility and at least one lower mounting facility. In these embodiment, generally, the upper mounting facility positions and secures the brace assembly about the thigh area of a user's leg, the lower mounting facility positions and secures the brace assembly about the shin area of the user's leg and the elastic hyperextension cross strap attaches to the upper and lower mounting facilities whereby the elastic cross strap can provide progressively increasing resistance to the extension of the user's knee when the elastic cross strap is positioned posterior to the user's knee. In some embodiments, the upper and lower mounting facility are defined entirely by the elastic cross strap to help secure the assembly to the user's leg. In some embodiments, the upper and lower mounting facilities are separate elements defined by portions of brace elements, such as upper and lower cuffs/pads or side braces, cooperating with the elastic cross strap.

In some embodiments, the brace assembly stabilizes the knee from hyperextension in the 5-25 degree range.

In some embodiments, the brace provides progressive resistance starting at an angle of flexion of about 60-80 or about 70 degrees and has a maximum resistance at about 15-25 or about 20 degrees of flexion.

Figure 1B:
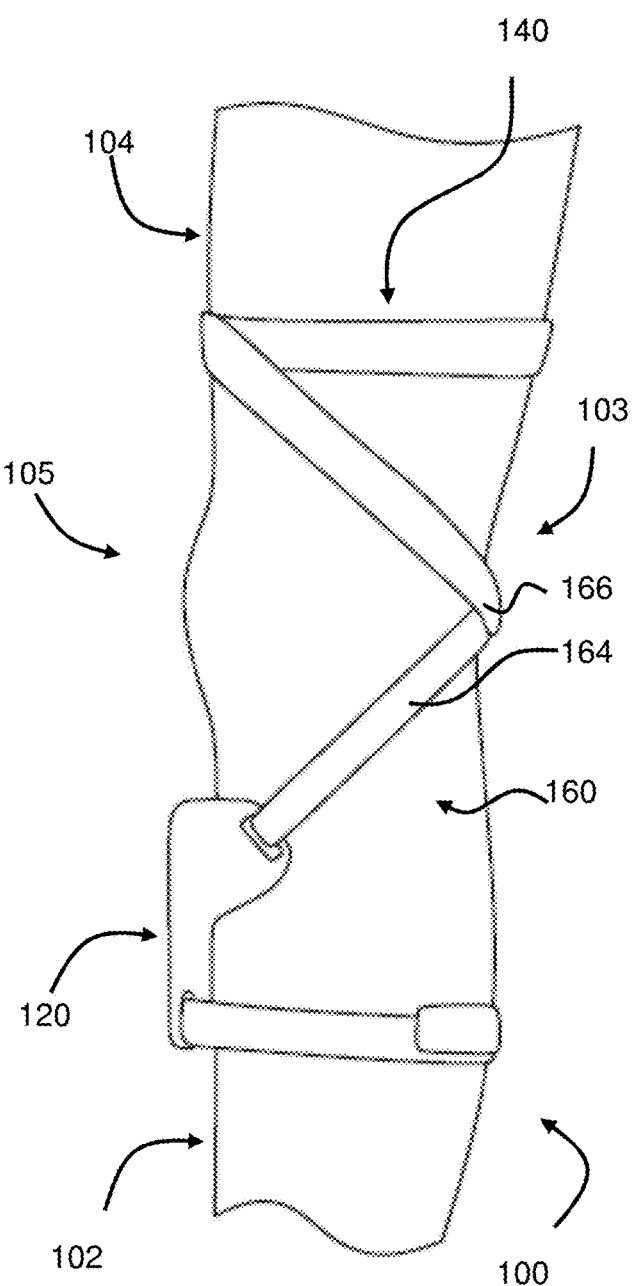
FIG. 1B illustrates a side view of the embodiment the brace assembly of FIG. 1A mounted on the knee of a wearer.

As shown in the example embodiments of FIGS. 1A and 1B, the elastic cross strap 160 is at least one elongated element able to provide a progressive tensile resistance force and capable of creating a cross pattern that creates a cross origin and cross strap arms. The elastic cross strap also comprises means to attach ends of the straps, the cross strap arms, to the upper and lower mounting facilities. In some embodiments, the elastic cross strap comprises the combination of multiple elongated elastic straps, cross strap arms, that may be configured to create the cross pattern that creates the cross origin and cross strap arms. In some embodiments, the elastic cross strap comprises a single cross strap that may be configured to create the cross pattern that creates the cross origin and cross strap arms. In some embodiments, the elastic cross strap comprises a single cross strap that has cross strap arms coming from a pre-defined or integrated cross origin.

In some embodiments, the elastic cross strap comprises one or more straps of pre-determined lengths and elastic cross straps are selected based on the length needed for that wearer. In other embodiments, the elastic cross strap has adjusting facilities or elements that allow the cross strap to be adjusted to fit the wearer and provide different resistance properties to help prevent joint extension.

The elastic cross strap can be made from material to provide resistance to stretching in one direction. In one example embodiment, the elastic cross strap is a pliable elastic material that provides progressive resistance to stretching and as the material stretches, the resistance to stretching increases. As an example, the resistance properties of embodiments function similar to the resistance properties of a rubber band. In one embodiment, the elastic material is similar to elastic sports tape. In other embodiments, the elastic material can comprise a rubber material, a plastic material or a spring that can provide resistance properties similar to those of a rubber band. It is also contemplated that the elastic cross strap may comprise a combination of elastic and non-elastic material that still provide the elastic properties required of the strap. As an example, and not for limitation purposes, these combinations may comprise combinations or laminates including cloths, fabrics, threads, struts or other materials combined with an elastic material through sewing, adhesives, Velcro® type attachment or even simple adjacent placement to elastic materials. These combinations or laminates may comprise multiple materials that can increase the adherence of the cross strap to itself or other materials and may be comprise combined materials at particular, not all areas of the cross strap. Combinations of elastomeric materials with varying resistance properties are also contemplated.

The length, width and elastic properties of the elastic cross strap can be varied based on the properties desired for the wearer and/or the sport the wearer will participate in. Although some of the discussion relates to a single elastic cross strap, it is understood that multiple elastic cross straps or straps can be used to provide the functional properties of the elastic cross strap. More than one elastic cross strap or strap can be used such that their properties combine to provide the desired resistance properties.

As shown in FIG. 1A, the elastic cross strap 160 has two cross strap arms 162 and 164 respectively configured to attach to a lower arm end to a lower mounting facility 120 at a lower attachment point. The lower mounting facility further comprises securing elements, such as straps 124 to engage the wearer's lower limb as well as points to attach this element to the other elements of the assembly. Embodiments of the lower mounting facility include but are not limited to a hard shell, pad, cuff, portions of the strap, portions of a sleeve or any other element capable of mounting the brace to the wearer's limb. In this embodiment, the lower mounting facility 120 is a shin shell 121 mounted anterior to the knee and just below the wearer's knee with one or more securing strap 124. In some embodiments, the lower mounting facility comprises a polyethylene cuff. In the embodiment shown, the tibial shell can be made of a flexible material or when desired, it can be made of more rigid material to provide some tibial protection to the wearer.

Means to attach or couple the elastic cross strap arms to the mounting facilities include, but are not limited to common attachment means such as: rigid fasteners such as rivets, adhesives or sewing; slidable attachment points such as slots or channels, pivoting fasteners such as rivets or buttons; and removable fasteners such as Velcro, buttons, buckles, snaps or hooks. It is contemplated that the means of attachment, such as with Velcro straps or buckles, will let the cross strap be tightened or loosened as desired for comfort, support or specific resistance reasons. As used herein, attach, attachment and means to attach include couple, coupling and means to couple.

As shown, the attachment of the elastic cross strap in FIG. 1 is through lower attachment points that comprise multiple openings 122 in the shell positioned so that the elastic cross strap arms 162 and 164 weave through the shell and extend up towards the wearer's thigh. When installed as in FIG. 1B, these elastic straps extend from the anterior tibia at the patellar attachment and wrap posterior with one wrapping medial and one wrap laterally to attach to the wearer's anterior thigh pad. This "X-strap" configuration creates elastic straps running from an anterior tibial pad 121 with one strap medial and one strap lateral to cross like an X in the popliteal fossa 103 behind the knee 105, then coming back to an anterior of thigh pad 140 in the middle to upper one-third of the thigh.

It is also contemplated that the shin shell can be configured to allow the same straps, or additional straps, clips or bands, to wrap around the wearer's lower leg to secure the lower arms of the elastic cross strap.

The upper mounting facility positions the brace assembly about the upper limb of a wearer's joint. Embodiments of this facility can similarly include those possible for the lower mounting facility. In the embodiment shown in FIG. 1, the upper arms of the elastic cross strap are configured to connect to each other and perform the function of the upper mounting facility 140, much like a thigh pad in a traditional knee brace. In this embodiment, the thigh side connection is made by connectors 146A and 146B on the end of the upper arms extending up the wearer's thigh. As shown, this connection is made by complementary hook and loop type Velcro fasteners on the thigh end of the straps but any connection or coupling means can be used such as but not limited to complementary hooks, buttons, buckles, slots, loops, adhesives or clips. In this embodiment, the thigh end of the straps can provide the functionality of a thigh cuff in traditional knee braces by wrapping the straps around the wearer's thigh to help secure the assembly to the thigh. In the embodiment shown, sections of the upper arms also contain optional facility attachment elements defining a facility attachment point 142 that allows the upper arms to attach to the upper mounting facility in particular places such as the anterior position shown. Examples of attachment element can include all those possible for the lower mounting facility. In one embodiment, the attachment elements comprise matching Velcro sections attached on the upper arms of the elastic cross strap. These sections are placed on the elastic cross strap arms 162 and 164 in pre-determined locations that will allow proper positioning of the elements and help ensure the attachment can be maintained anterior to the limb and towards a front portion of the mounting facility.

For the embodiment of FIG. 1, the attachment point 142 functions generally as an upper anterior resistance point and a point generally mid-way between the lower attachment points functions as the lower anterior resistance point.

Figure 2:
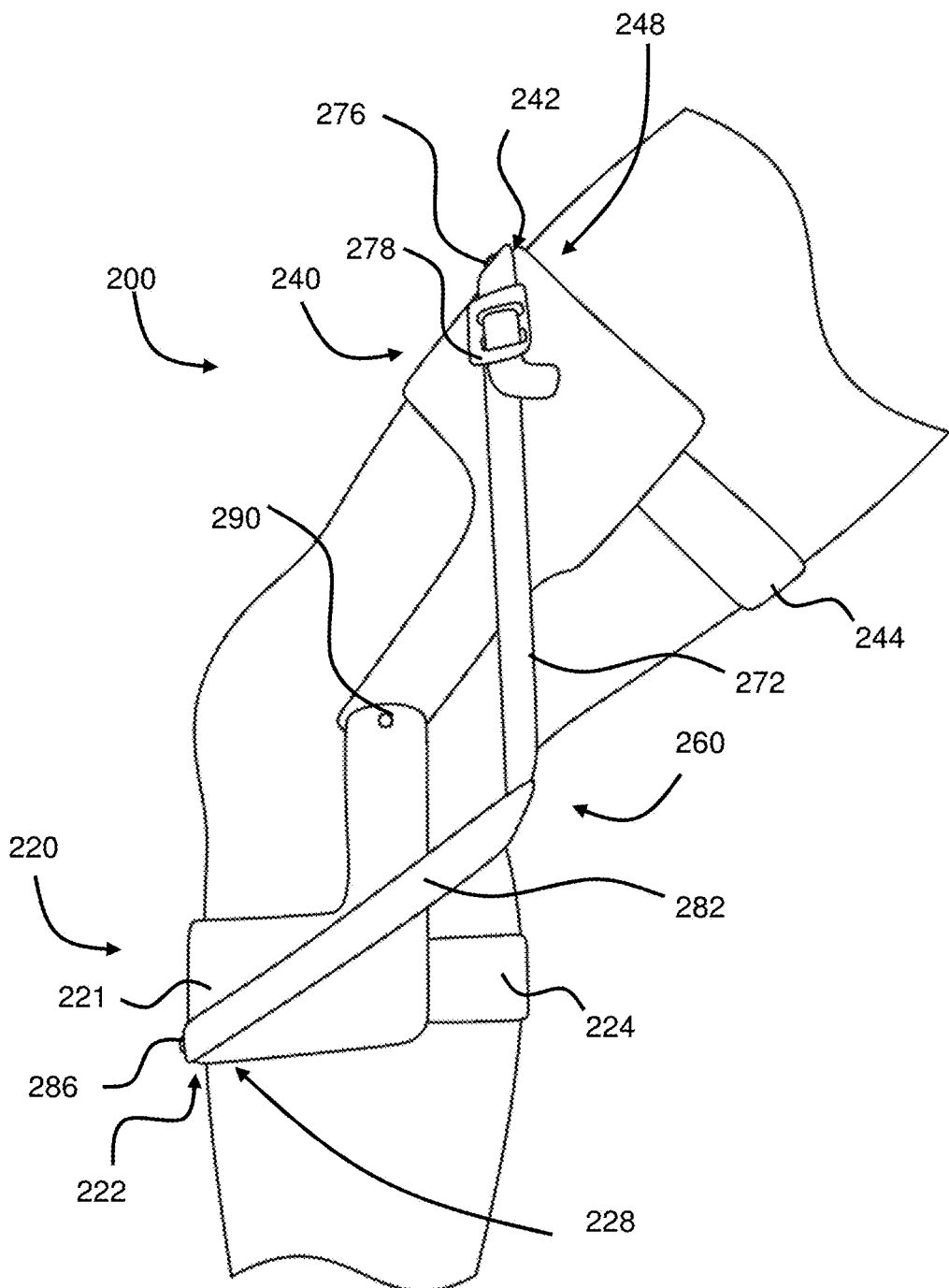
FIG. 2 illustrates a side view of one embodiment of the brace assembly having an upper and lower mounting facility.

In embodiments where the upper mounting facility comprises an upper pad or thigh pad, as shown in FIG. 2, the thigh pad 240 can comprise any non-rigid material that can engage the wearer's thigh and attach this pad to other elements of the assembly. Suitable materials for this pad include but are not limited to cloth, cotton, plastic, nylon, mesh, leather and elastic materials. This pad may further include padding or may be heat pliable, molded or contoured to be more comfortable for the wearer. In some embodiments, the upper mounting facility comprises a polyethylene cuff. The embodiment in FIG. 2 illustrates one embodiment of an anterior thigh pad 240 which can be shaped to the contour of the medial anterior thigh above the vastus medialis oblique.

FIG. 2 also shows that embodiments of the assembly 200 can include a lower mounting facility 220 having a tibial pad 221 with similar mechanical characteristics as the thigh pad 240.

In embodiments, as shown in FIG. 2, the mounting facilities 220 and 240 include at least one securing strap, here lower and upper securing straps 224 and 244, operably connected to the facilities to secure them onto the wearer's limbs. Any means to secure the pads and tighten the pads onto the wearer's body is suitable. In one embodiment, a Velcro type securing strap is attached to each of the pads and when the strap is secured to the pad around the wearer's limb, the pads are secured to the wearer. Other suitable means to secure the facilities to wearer's limbs include but are not limited to a sleeve around the limb and straps with adjusting facilities such as buckles.

It is contemplated that in some embodiments, rather than connecting or coupling the elastic cross strap 260 to the pads, the securing straps 224 and 244 can also provide the attachment means for the pads to the elastic straps. For example, the securing strap may wrap all the way around the limb and have the attachment means so that when the securing strap is secured to the pads, the elastic cross straps are attached to the securing strap.

The elastic cross strap 260 is attached to the upper and lower mounting facilities at upper and lower facility attachment points 242 and 222. This attachment can be made using any means that will secure the ends of the elastic cross straps onto the mounting facilities and is generally made at a front portion of the mounting facility. As shown in FIG. 2, the elastic cross strap arms are permanently attached to the attachment points 242 and 222 on the facility front portions 248 and 228 by rivets at strap attachment points 276 and 286. Attachment means includes any of the attachment means already described. If the thigh pad is not used, the elastic cross straps can be wrapped around the wearer's thigh and connected to themselves to secure the assembly to the wearer.

For the embodiment of FIG. 2, the attachment points 242 and 222 function generally as the upper and lower anterior resistance points respectively.

FIG. 2 also illustrates the adjusting facilities that can be used to adjust the length, or effective length, of the elastic cross strap. By adjusting the effective length of the elastic cross strap, the elastic tension and resistive properties of the cross strap can be adjusted. Adjusting element 278 comprises a buckle that allows the arms 272 and 282 of the elastic cross strap to be put through the buckle and adjusted. (An adjusting facility on the other side of the brace can be provided but is not shown.) Examples of suitable adjusting facilities include but are not limited to buttons, Velcro, snaps or hooks or any type of adjustable connections that allows a connection that can alter the effective length or resistance properties of the elastic cross strap. It is understood that providing elastic cross straps of varying length is also another example of a suitable adjusting facility.

FIGS. 1B and 2 illustrate the extension of the brace and the limbs about the joint. FIG. 2 illustrates one example embodiment of a brace and knee where the brace and knee joint are slightly bent. FIG. 1B illustrates one example embodiment of a brace and a knee joint extended from a position such as in FIG. 2. An extension of the brace or the limbs about the joint, when used herein as a verb, is the action by which the brace or the limbs about the joint are extended from a bent position to a straight position (180° angle) or sometimes beyond a straight angle (e.g. hyperextension).

Figures 3A, 3B:
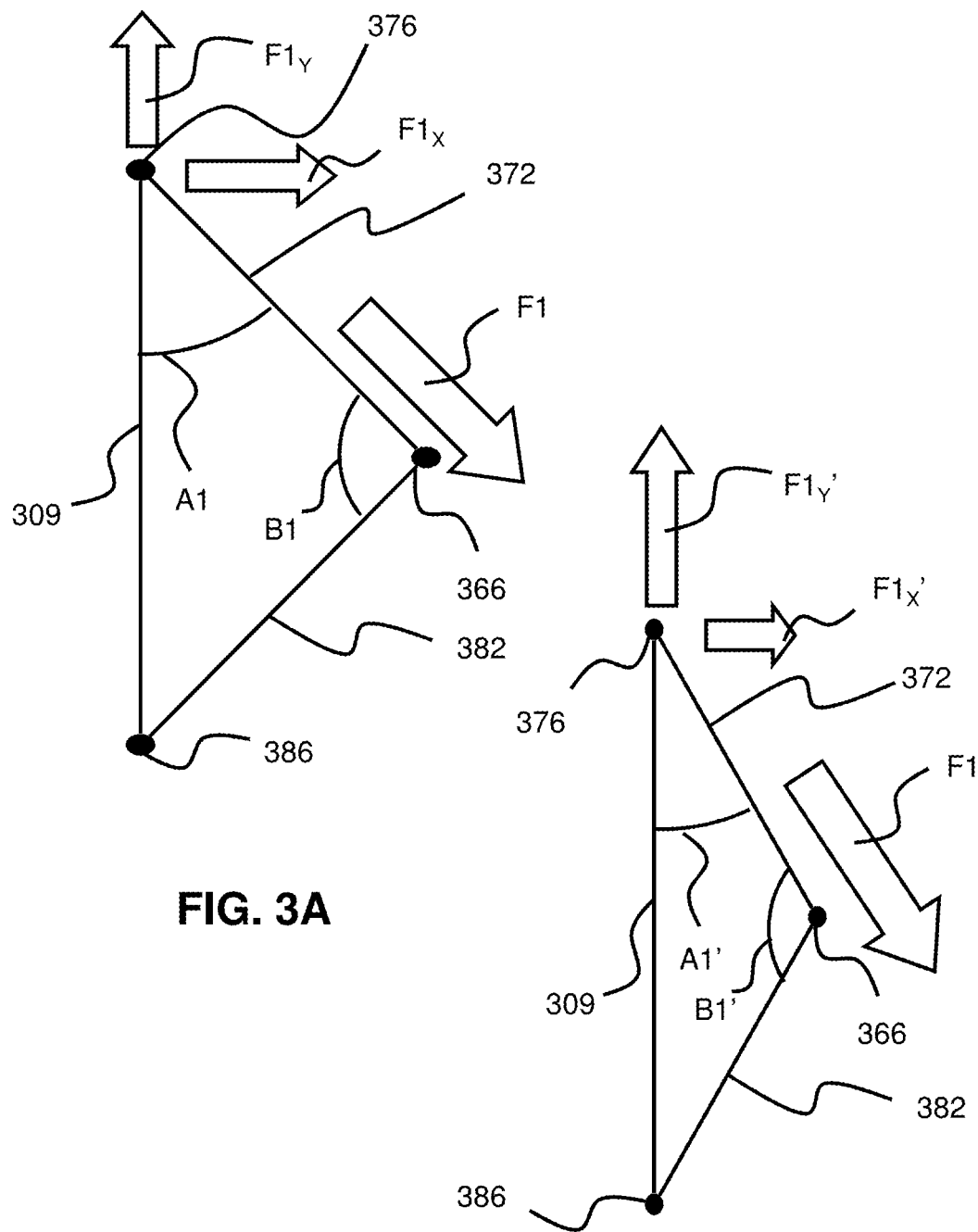
FIGS. 3A and 3B illustrate the force patterns of example embodiments of the cross strap when mounted around a knee.

In some embodiments of this brace assembly, it is beneficial for the elastic cross strap to provide a sufficient resistance force to an extension of the limbs about a joint at or near an anterior point of the wearer's leg. This resistance force is applied to the limbs about a joint by resisting an extension of elements of the brace itself between the cross origin and the anterior resistance points. By resisting the extension of elements of the brace, such as the anterior resistance points about the cross origin, elements of the brace are able to help limbs resist their extension about the bending axis of the joint. The bending axis of the joint is the actual or conceptually equivalent point of the joint about which the limb/body portions bend or rotate. When the cross origin is positioned posterior to the joint, which is posterior to the joint's bending axis such as in a fossa of the joint, this typically means that the anterior resistance point may be positioned anterior to the joint at a front portion of the mounting facilities. The anterior resistance point is typically the point at which the resistance force is applied to the brace portion that applies that resistance force to an extension force applied to the brace by the extension of the limbs. In most, but not necessarily all embodiments, the anterior resistance point is the same as the attachment points. For example, as represented in FIGS. 3A and 3B, this assembly benefits from a configuration that maximizes the tensile force that the elastic cross straps can provide. In FIG. 3A, the lines 372 and 382 represent the upper and lower elastic cross strap arms respectively of an elastic cross strap and the points 376 and 386 represent their strap attachment points and point 366 represents the cross origin. In the embodiment illustrated, the cross origin 366 would be posterior to the joint bending axis. The attachment points represent examples of the upper and lower anterior resistance points from which the cross strap provides the resistive force that counters the extension force caused by a joint extending. The line 309 generally represents the front part of the wearer's leg. Using the upper strap attachment point 376 as an example, the resistance force F1 that upper elastic cross strap upper arm 372 provides at the upper anterior resistance point can be translated into F1subX and F1subY forces as shown. Using trigonometric and static principals, the angle A1 allows the force to be translated in the X direction as F1subX=F1 (sin A1). As compared to FIG. 3B, where the angle A1prime of the elastic cross strap arm 372 to 309 is less than A1, the resistance force F1subX to be applied is less. Therefore, as designed, the attachment of the elastic cross strap onto the brace assembly towards the anterior, or front portion of the brace, provides more resistance than known prior art brace assemblies with straps that provide predominantly posterior resistance points and smaller angles at A1. This positioning also reduces the force that would otherwise be put on the brace in the direction of F1suby. By reducing this force, the forces that would tend to cause the brace mounting facilities to migrate towards each other are reduced.

The resulting angles shown in FIGS. 3A and 3B will vary for each patient given their size, strength in order to control extension of the joint. In some embodiments of the brace assembly, the angle from the lower attachment point and upper attachment point about the cross origin (FIG. 3A angle B1) can be in a range of about 50 to 160 degrees, 60 to 140 degrees or 75 to 115 degrees.

In addition to providing superior resistance properties, embodiments utilizing an elastic cross strap may also provide the benefit of eliminating the immediate hard stop typical of prior art embodiments that use hard stop features such as in a hinge or with a non-elastic strap. This lack of a hard stop helps prevent migration of the brace and reduces the jerking feeling making the brace more comfortable for the wearer. The inclusion of providing progressive resistance with the elastic cross strap provides additional benefits. The elastic properties of the cross strap can provide resistive properties earlier in the motion arch of the joint thereby controlling extension sooner. Additionally, the elastic properties can provide increasing resistance in a linear fashion as the joint goes from flexion to extension which increases neuromuscular control and causes the extensor muscles to gradually strengthen which is good for joint stability.

In some embodiments, the elastic cross strap has a limiting resistance capability. For these embodiments, the limiting resistance may be provided by the elastic properties of the elastic cross strap reaching its maximum extension and therefore the cross strap provides a direct resisting force to further cross strap extension. This limiting resistance may also be provided by having a non-elastic material used in combination with an elastic material whereby when the limiting resistance point is met, the non-elastic material is engaged and that provides the direct resisting force to any further extension of the elastic cross strap.

Figures 4A, 4B:
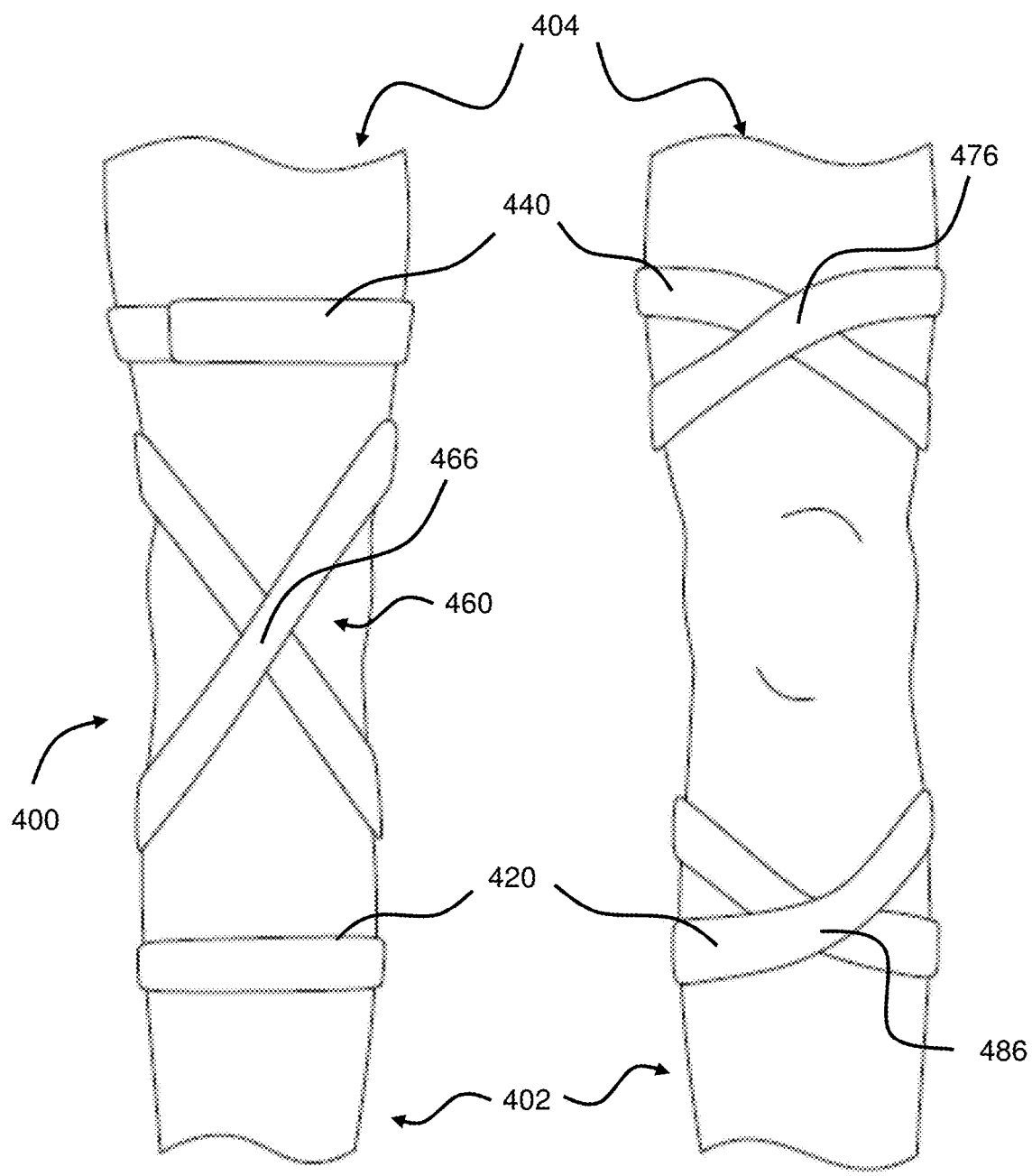
FIG. 4A illustrates a front view of one embodiment of the brace assembly comprising a single cross strap about the knee of a wearer.
FIG. 4B illustrates a rear view of one embodiment of the brace assembly comprising a single cross strap about the knee of a wearer.

Other Embodiments of the Brace:

One embodiment of the brace assembly comprises a single elastic cross strap mounted in a way that provides the functionality of the brace. As shown in FIGS. 4A and 4B, this embodiment comprises a single elastic cross strap 460 that is wrapped around the wearer's shin 402 to create the lower mounting facility 420, the arms of the elastic cross strap are then wrapped behind the knee to cross in the popliteal fossa of the knee to create the cross origin 466. The arms are then extended and wrapped around the wearer's thigh 404 to create the upper mounting facility 440.

In this embodiment of the brace assembly 400, the wrapping around the shin 402 may start with the middle of the elastic cross strap 460 being placed in the back of the calf. The wrapping can continue around the lower leg once or multiple times. At the point that the elastic cross strap is extended from a position anterior to the shin and then up behind the knee. There may be elements to help define the strap attachment points 486 to assist in keeping the arms of the cross strap properly positioned anterior to the joint. The wrapping around the thigh 404 may also be done once or multiple times with attachment means or coupling means such as hooks, bands, buttons, buckles, loops, clips, Velcro or straps to keep the straps together and define the strap attachment point 476. To close the elastic cross strap, any connection means already disclosed, such as complementary hook-and-loop (Velcro) connectors can be used to secure the upper arms to each other. For the embodiment illustrated in FIGS. 4A and 4B, the strap attachment points 476 and 486 function generally as the upper and lower anterior resistance points respectively.

Although the embodiment in FIGS. 4A and 4B illustrate an embodiment of a single strap with two free ends, embodiments of one single strap in a loop are contemplated that can similarly be used as the brace assembly.

Figure 10:
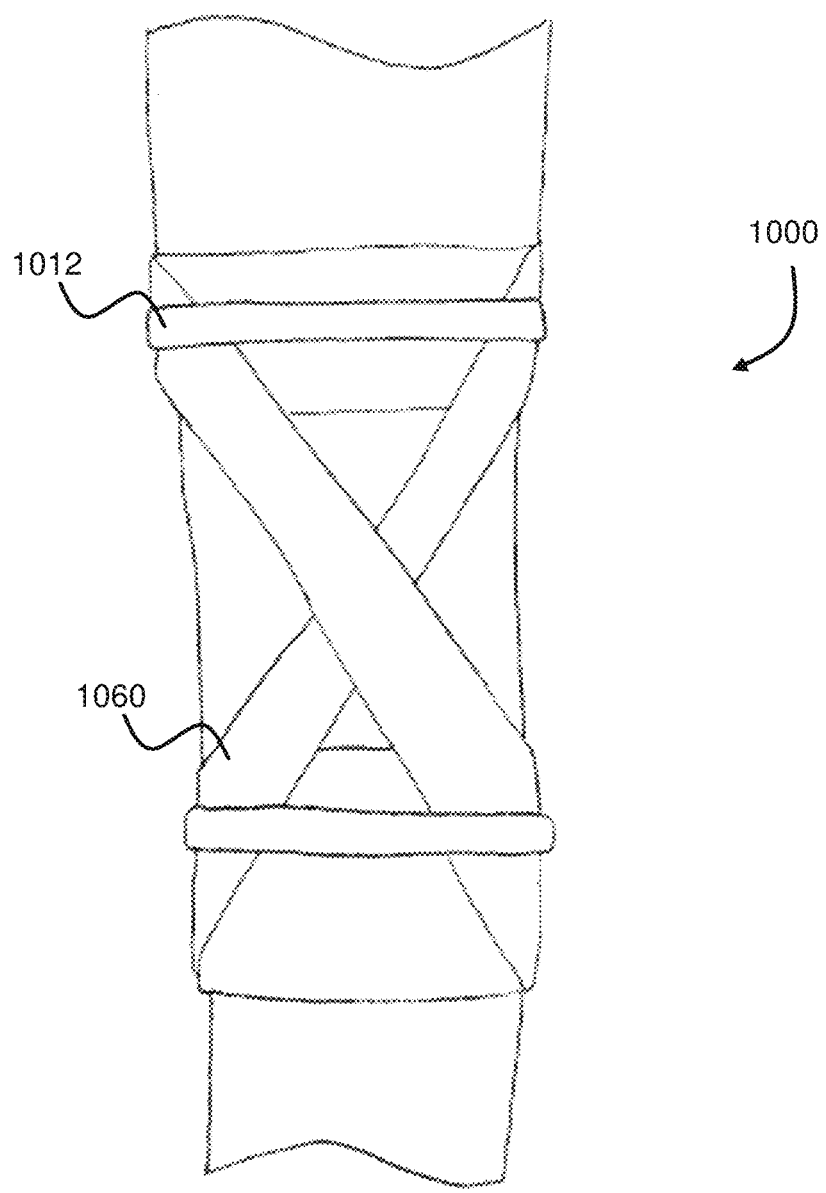
FIG. 10 illustrates a rear view of another embodiment of the brace assembly.

One embodiment similar to that in FIGS. 4A and 4B is shown in FIG. 10. This embodiment comprises an elastic wrap material such as latex or latex-free Esmark Wrap sold by Medline Industries of Mansfield Mass. being used as the cross strap. The elastic wrap 1060 is positioned about the joint as described with the embodiment shown in FIGS. 4A and B and secured about the wearer's leg by any type of securing means such as an adhesive tape 1012, securing the elastic wrap to itself by wrapping it around the leg in multiple layers or by having a multiple property elastic cross strap that allows the strap to adhere to itself.

Figure 5:
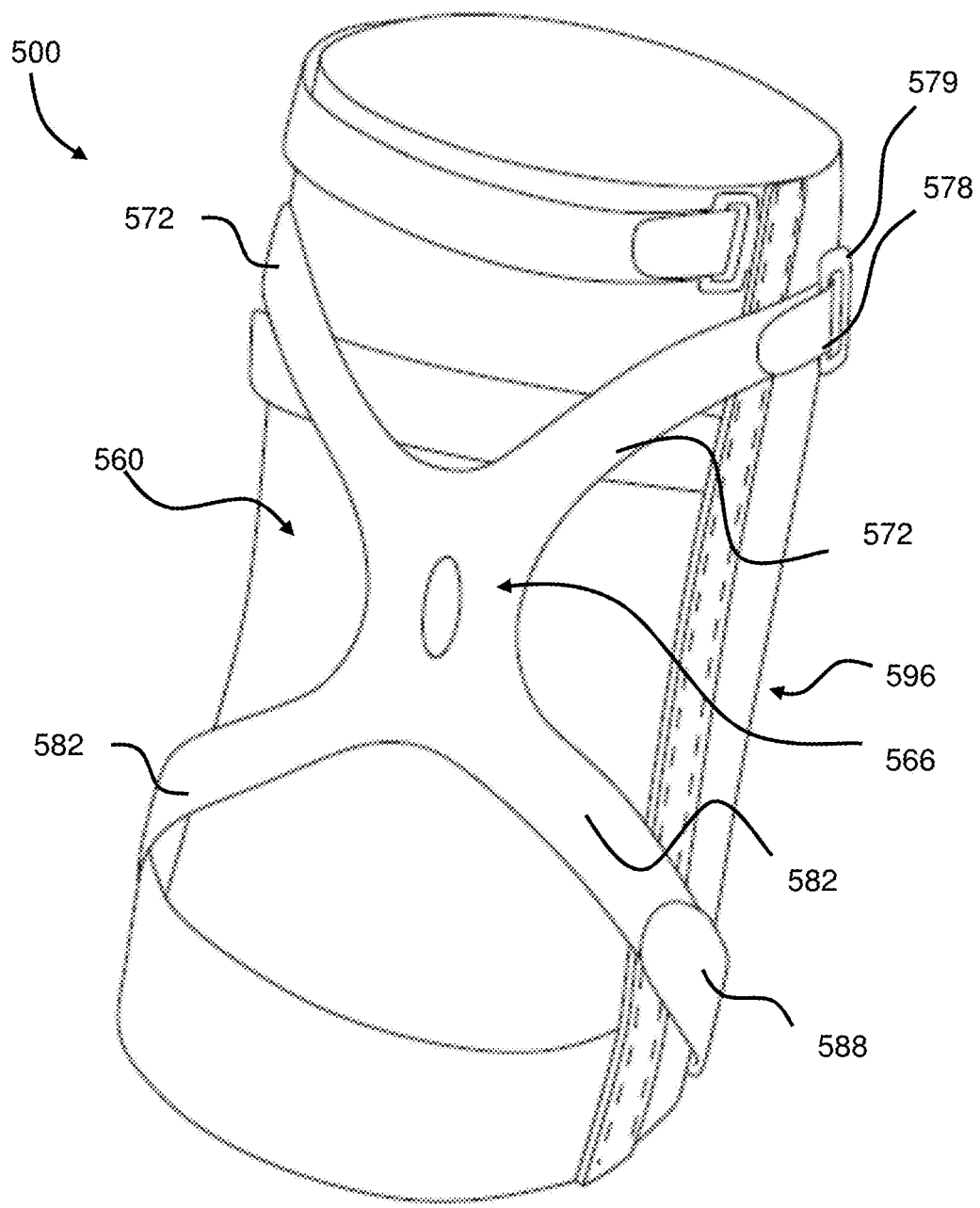
FIG. 5 illustrates a rear view of one embodiment of the brace assembly having an x-shaped cross strap cooperating with a sleeve.

Another embodiment of the brace assembly utilizes a single elastic x-strap as the elastic cross strap. As shown in FIG. 5, the assembly 500 has a single elastic cross strap 560 having a cross origin 566, upper arms 572, lower arms 582 and attachment points (shown in FIG. 6 as fasteners 673 and 683). This elastic cross strap functions similar to the crossed single elastic cross strap. As shown, the elastic cross strap arms have Velcro fasteners that act as adjusting elements 578 and 588 on their end. These ends connect through loops 579 that are attached to Velcro fasteners (not shown) on both the upper and lower mounting facility. Adjusting element 578 is able to be pulled through the loops 579 and secured to itself at different positions creating arms of different lengths. In one embodiment, this elastic x-strap is long enough to extend from the anterior tibia at the patellar attachment and wrap posteriorly with one arm wrapping medial and one wrapping laterally to attach to the wearer's anterior thigh pad. This elastic "X-strap" configuration creates arms running from an anterior tibial pad with one strap medial and one strap lateral to cross like an X in the popliteal fossa of the knee, then coming back to an anterior thigh pad in the middle to upper one-third of the thigh.

Similarly, embodiments having two elastic straps can be made where two elastic straps are used to create the elastic cross strap.

Figure 6:
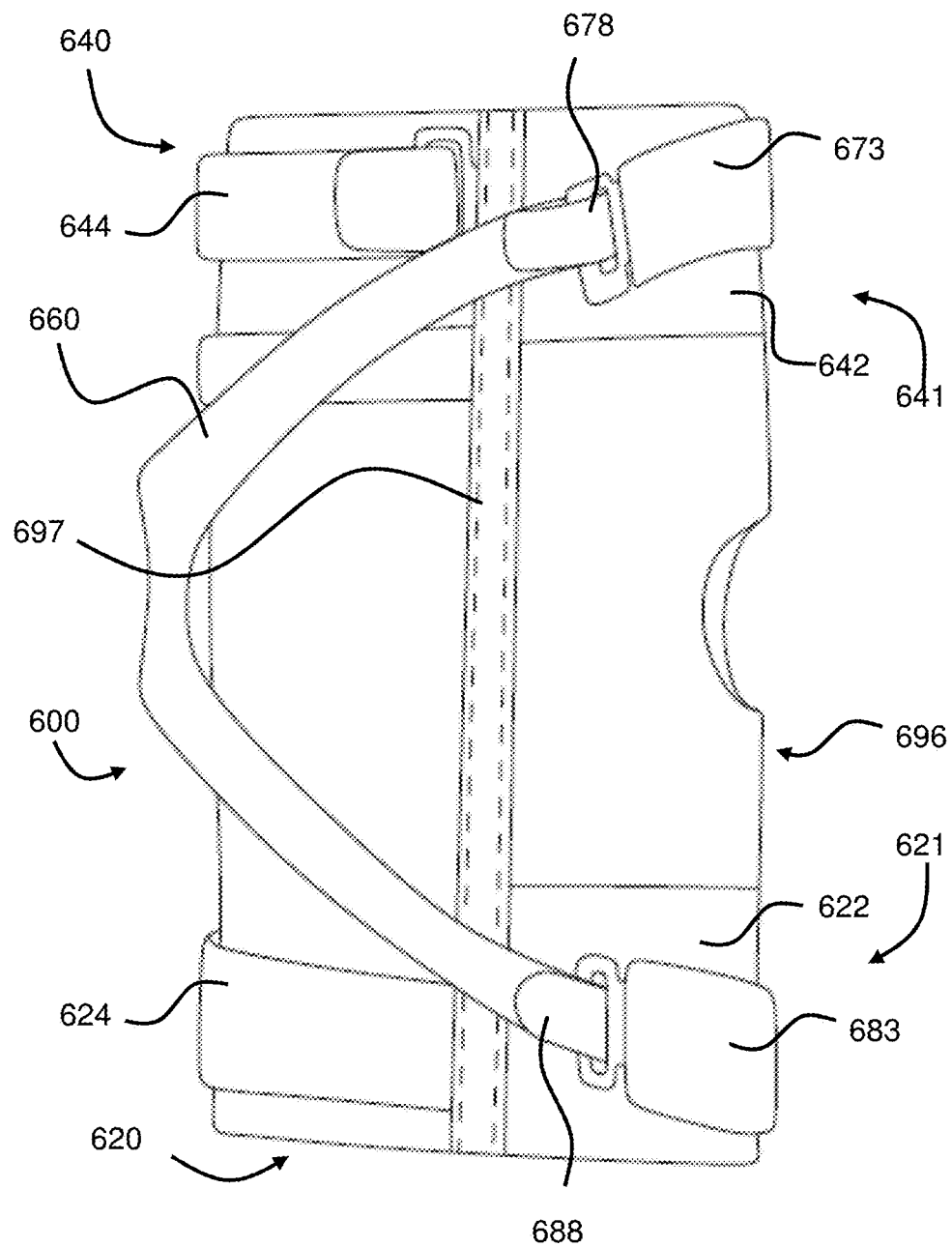
FIG. 6 illustrates a side view of one embodiment of the brace assembly showing the cross strap attachment to the upper and lower mounting facilities on a sleeve.

Embodiments of a brace assembly also include having a brace sleeve to provide assembly elements. This type of embodiment is shown in FIGS. 5 and 6. In FIG. 6, the upper and lower portions of the sleeve 696, portion 640 and 620, can function as the including the upper and lower mounting facilities respectively. The upper mounting facility 640 may comprise a portion as the upper pad/cuff 641 with an upper strap 644 helping secure the upper mounting facility 640 and cuff 641 to the leg. The lower mounting facility 620 may comprise a portion as the lower pad/cuff 621 with a lower strap 624 helping secure the lower mounting facility 620 and cuff 621 to the leg. The sleeve in these embodiments will rest against the wearer's skin and may be made of an elastic material. The surface of the sleeve that will touch the wearer's skin, the under sleeve, is a non-slick surface to frictionally engage the wearers limb. In the embodiment of FIG. 6, the inner surface of the sleeve 696 comprises an open faced diamond shaped web weave that frictionally engages the skin and also allows portions of the skin surface to be exposed. Other embodiments of the frictional surface of the under sleeve include but are not limited to high friction surfaces such as rubber, felt, mesh, elastic material or any combination of these surfaces. It is contemplated that under sleeve material can be used so that the under sleeve is in contact with the skin around the knee under the elastic straps to help keep them in place.

As shown in FIG. 6, embodiments of the brace assembly 600 can include additional fasteners 673 and 683. These fasteners provide the attachment between the upper and lower mounting facilities and the ends of the elastic cross strap 660 and function as the strap attachment points. With this configuration, the facility attachment points 642 and 622 on the mounting facilities comprises an entire anterior area of the brace having hook-and-loop type fasteners that can match with the under surface of the fasteners 673 and 683. In this configuration, the placement of the fasteners 673 and 683 up and down length of the brace adjusts the effective length of the elastic cross strap about the wearer's knee. This adjustment can be used in cooperation with the adjustment from the adjusting elements 678 and 688 to adjust the length of the elastic cross strap. Although these additional fasteners can be a separate element from the elastic cross strap and the cross strap arms, they function as an extension of the elastic cross strap.

Some embodiments of the brace assembly without metallic or rigid elements able to comply with current sporting regulations, such as the FIFA rules.

The embodiment shown in FIG. 6 also includes optional flexible uprights 697 on one or both sides of the brace. An upright as used in this description is a hinge that has a high degree of axial stiffness and a high degree of bending flexibility. Examples of suitable uprights would be coiled spring cables, chain links or ball-and-socket links, planar struts or flexible struts that prevent the upper and lower mounting facilities from urging towards each other when the assembly is subjected to the forces of the elastic straps. The upright has the capability to bend in one or more planes while not compressing. The upright can be directly connected to the pads, sewn into the sleeve or be attached to other elements that are connected to the pads to keep the pads from urging towards each other. In these embodiments, suitable material for the uprights include, but is not limited to metals, Kevlar or carbon fiber type construction that will provide flexibility but not let the upright compress. Suitable overall shapes for the upright include but are not limited to a flexible rod that easily allows flexing of the knee when the uprights are installed on the wearer's leg.

Embodiments of the brace assembly can also include traditional knee braces elements such as upper and lower frames with central hinges as well as structures for patellar control. The elastic cross strap could be added to these assemblies to provide additional support and hyperextension protection. As shown in FIG. 2, the elastic cross strap 260 can function with a thigh cuff 240 and a tibia cuff 221. The elastic cross strap crosses behind the knee and the arms attach to the facility attachment points 242 and 222 on the cuffs. The hinge 290 of the brace can be of any type uses with traditional braces to include, but not limited to monocentric hinges, polycentric hinges, flexible uprights or any other hinge commonly used in joint braces.

Embodiments of the brace assembly can also include an elastic cross strap with a single rigid side strut and hinge or flexible upright. For example, this type of embodiment could be worn as a prophylactic brace on the lateral side of the knee to reduce knee injuries and reduce the chances of rigid brace elements colliding with each other and interfering with the user's leg movement. In these embodiments, the cross strap can comprise any of the descriptions included herein and is attached to the side strut or upright using the attachments means disclosed. The single rigid side strut and hinge can be similar to any of the side brace and hinge designs disclosed and the flexible upright can be similar to any of the flexible uprights disclosed in other embodiments with or without a sleeve.

Figure 7:
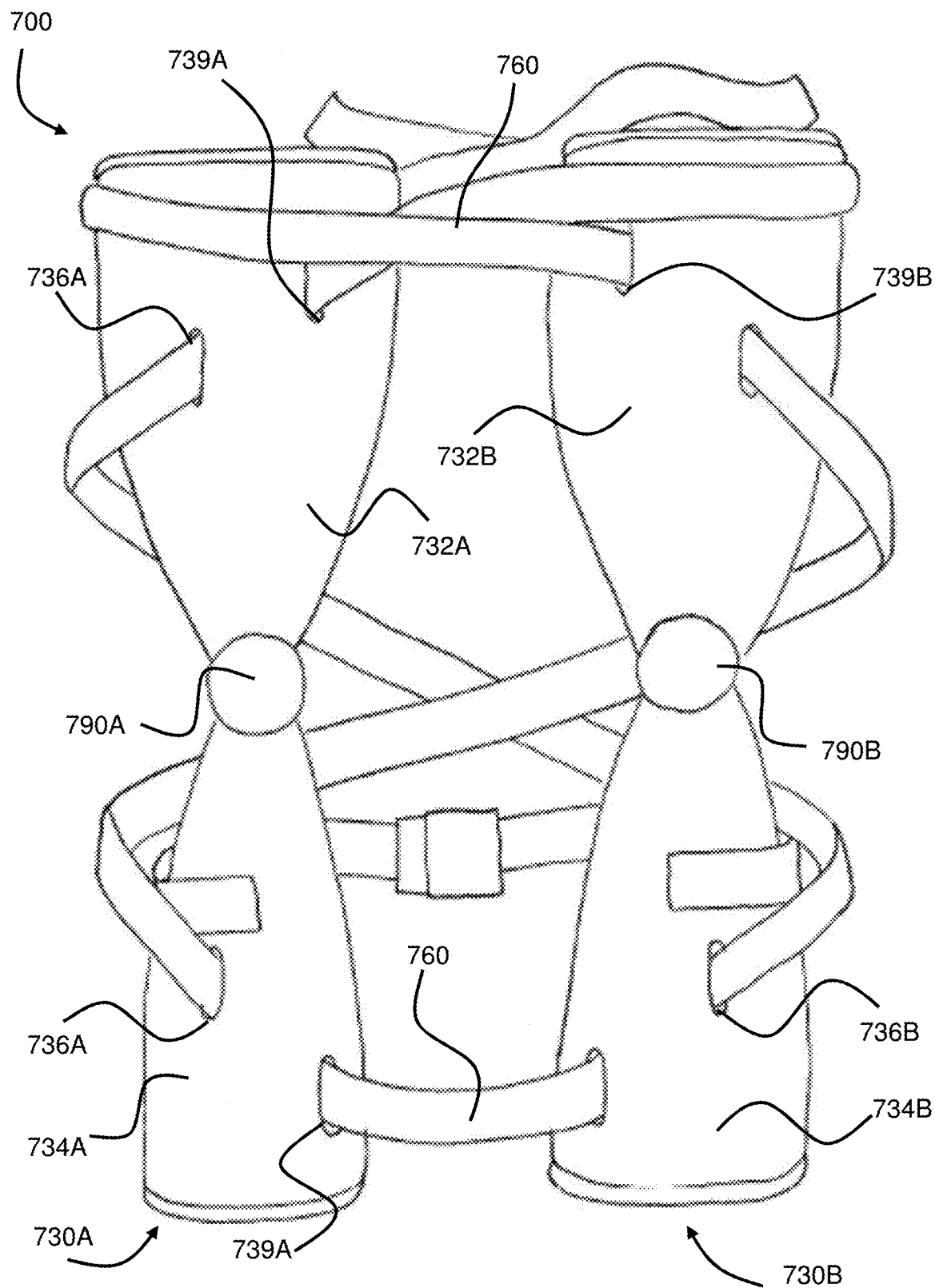
FIG. 7 illustrates a front view of another embodiment of the brace assembly with the side brace elements extended.
Figure 8:
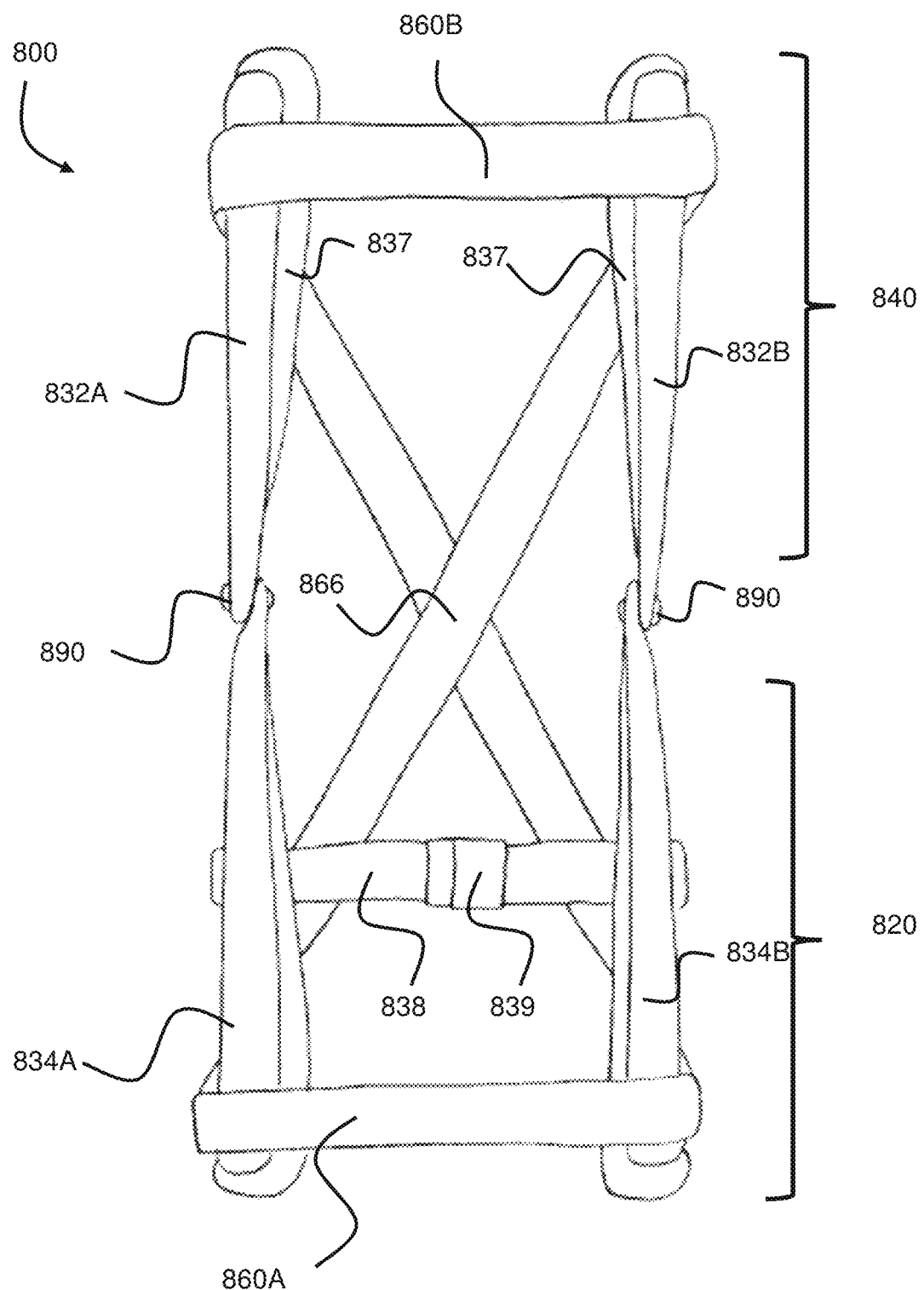
FIG. 8 illustrates a front view of one embodiment of a brace assembly positioned as if it were put on a wearer's leg.
Figure 9:
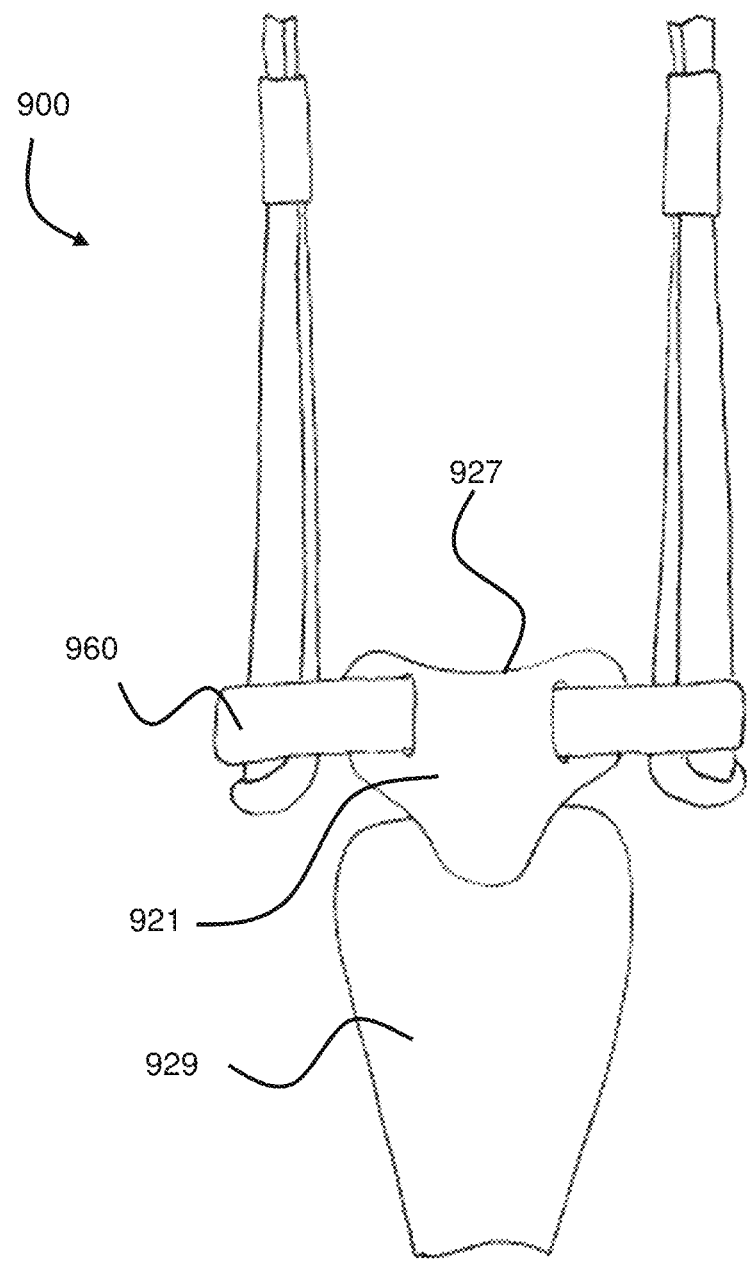
FIG. 9 illustrates a front view of another embodiment of the lower portions of a brace assembly with a shin shell positioned as if it were on a wearer's leg.

Additional embodiments of the brace assembly are shown in FIGS. 7, 8 and 9.

FIG. 7 shows a front view of one embodiment of the brace assembly 700 with the side brace elements 730A and 730B turned forward for illustration. In this embodiment, the upper and lower mounting facilities are defined by upper and lower portions of multiple side brace elements together with connector elements. One side brace element (e.g. medial) comprises an upper portion 732A, a lower portion 734A and a hinge 790A that allow the upper and lower portions to pivot relative to each other. Similarly, the other brace element (e.g. lateral) comprises an upper portion 732B, a hinge 790B and a lower portion 734B. This embodiment cooperates with an elastic cross strap 760 that is attached at various points to the side brace elements. As shown, the lower mounting facility is defined by the lower portion of both side brace elements (portions 734A and 734B) together with the portion of the elastic cross strap 760 attached to the lower brace portions. In a similar fashion, the upper mounting facility is defined by the upper portions (732A and 732B) of the medial and lateral brace elements cooperating with portions of the attached elastic cross strap 760.

The composition of the side brace elements in this embodiment can be of any rigid or semi-rigid material that can engage the side of a wearer's leg, attach the side elements to the elastic cross strap and provide a degree of rigidity to the assembly when stationary or when the upper and lower mounting facilities pivot about the hinges. Suitable materials include but are not limited to plastics, metals, composites or any combination of these materials. The brace elements may further include padding or may be heat pliable, molded or contoured to be more comfortable for the wearer. As shown (FIG. 8, 837), the side brace element includes an interior pad portion such as but not limited to foam, rubber, cloth, cotton, plastic, leather or any combination of these materials. The pad portion provides a comfortable surface between the more rigid side element portions and the wearer's skin. Side attachment points and on the side brace elements can include any means of attaching the elastic cross strap to the brace elements. As shown, one embodiment of the side attachment means comprises a series of slots such as 736A and 736B in the side brace elements. In this embodiment, the slots allow the elastic cross strap to be put into one slot such as 736A and exit another slot such as 739A. This "weaving" of the elastic cross strap through the side brace element attaches that portion of that elastic cross strap to that portion of the brace element. The side attachment points may allow the elastic cross strap and brace elements to be adjusted for each user. As shown, the weaving of the strap through the brace allows the strap to move within the slots and therefore adjust the position and/or tightening of the brace on a wearer. Although not required, in some embodiments, the attachment means are offset as shown with one means, typically the attachment means posterior to the joint, closer to the brace hinge and the other means, typically the means most anterior, furthest from the brace hinge. This configuration assists in the proper positioning of the cross strap within the brace and about the joint. Although weaving through slots are shown as an example attachment means in this embodiment, it is understood that any method of attaching the elastic cross strap to the side brace element is anticipated such as but not limited to hook-and-loop fasteners, hooks, buttons, clips, adhesives or any other attachment or connection means. When using the side brace elements, the side attachment points between the brace elements and the elastic cross strap do not always coincide exactly with the configurations of attachment points as described above and shown in FIGS. 1, 2, 4, 6 and in particular FIG. 3. It is understood that with side brace embodiments, the resistance to hyperextension can still be performed by the elastic cross strap that is wrapped around the front portion of the wearer's leg. In configurations that have attachment points about the side of side brace elements and the strap wraps around the limb, the elastic cross strap defines an anterior resistance point that will typically lie somewhere about half-way between the elastic cross straps attachment to one brace element and the other (for example, between 739A and 739B). It is from this anterior resistance point of the elastic cross strap, that the attachment point and anterior resistance point benefits described in FIGS. 3A and 3B are gained.

Figures 11A, 11B:
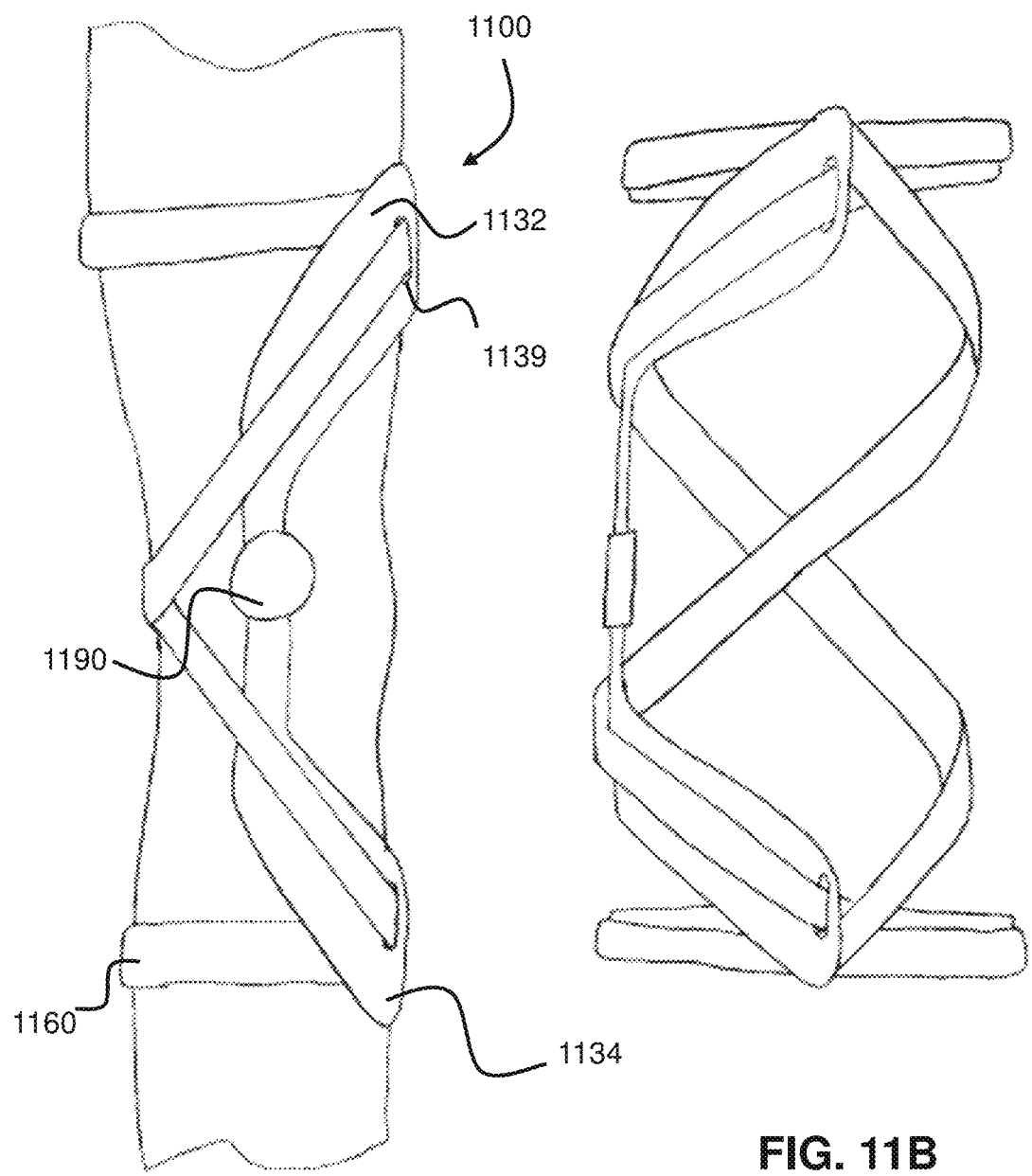
FIG. 11A illustrates a side view of another embodiment of the brace assembly mounted about a wearer's knee with lateral hinge side paddle.
FIG. 11B illustrates a front view of the embodiment in FIG. 11A as if it were on a wearer's leg.

It is understood that alternative shapes of side braces may be used. For example, and not for limitation, one embodiment shown in FIGS. 11A and 11B comprises brace assembly 1100 having a single lateral side brace configured with upper and lower paddle shaped side brace elements 1132 and 1134 respectively, extending from the hinge 1190 and hooking towards the anterior side of the brace assembly. In this embodiment, the paddle shape provides some rigidity to the brace assembly while also helping the cross strap 1160 maintain a beneficial position anterior to the joint providing a better anterior resistance point. Additionally, because only one lateral side brace is used, this can minimize the collision of brace assembly elements that may otherwise occur with rigid or semi-rigid medial side brace elements. In this embodiment shown, the attachment means, such as slot 1139, can be positioned on the end of the paddle so that it will allow both the attachment of the cross strap coming from the lateral side of the joint, as well as help secure the cross strap coming from the medial side of the joint. As shown, the slot 1139 is positioned lower on the paddle end so that the cooperation of the paddle end and the cross strap coming lateral helps position the cross strap portion going medial from the upper mounting facility so that it is not urged towards the joint when put under tension. The same type of configuration can be used on the lower paddle as shown. It is understood, that other means to guide the cross strap at the ends of the paddles can be used such as but not limited to ridges, multiple slots, channels, rings or other attachment means. For example, in one embodiment, the distal ends of the paddles can have two open slots that are dimensioned to allow the cross strap to be easily put into the slots while the slots help prevent the cross strap portions in the slots from urging towards the joint when the strap is put under tension.

The composition of the elastic hyperextension cross strap is similar to the descriptions described for other embodiments. The composition, function and design of the elastic cross strap and other elastic components of the brace assembly may be similar to the elastic portions of the training brace assembly as described in U.S. patent application Ser. No. 13/541,796 filed Jul. 5, 2012 and published as U.S. Pub. No. 2012/02700708 on Oct. 25, 2012, now U.S. Pat. No. 9,320,634 issued Apr. 26, 2016, which application is herein incorporated by reference in its entirety.

When assembled, as shown in FIG. 8 (with the wearer's knee), embodiments of the brace assembly function similar to the embodiments describe herein. The upper mounting facility is shown generally as 840 and the lower mounting facility is shown generally as 820. The upper portions (832A and 832B) and lower portions (834A and 834B) of the brace elements can pivot about the hinges 890. A portion of the elastic cross strap (860B) wraps around the front of the wearer's leg about the thigh, another portion of the elastic cross strap (860A) wraps around the front of the wearer's leg about the tibia and the elastic cross strap crosses behind the knee creating a cross-origin 866. The side brace elements help keep the position of the elastic cross strap as well as provide some rigidity to the assembly.

Shown in FIGS. 7 and 8, an optional securing strap 838 can be strapped around the wearer's leg to help secure the brace assembly on the leg. The securing strap is secured to both of the side brace elements at a securing point and can include a buckle 839 or other means to connect/couple the ends of the securing strap. It is understood that securing straps can be used on either the upper or lower portions or both portions. The securing strap may also be used around the front of the wearer's leg if necessary and can be positioned at various locations between the hinge and the distal end of the brace portions.

In one embodiment shown in FIG. 9, the brace assembly 900 with side brace elements can be integrated with embodiments similar to those shown in FIGS. 1A and 1B. As shown in FIG. 9, a shin shell 921 can be attached to portions of the elastic cross strap 960 so that the shin shell provides some protection to the shin of the wearer. As shown, the upper shaped edge 927 of the shin shell in embodiments can be shaped to align with the exterior shape of the tibial tubercle of the knee. As described above, the shin shell can also be made of a flexible material or when desired, it can be made of more rigid material to provide some tibial protection to the wearer.

One embodiment of the brace assembly further comprises configuring the tibial pad to function as an endo-skeleton such as with a wearer's shin guard, as may be required in a sport such as soccer, to support anterior tibia and anterior drawer control. FIG. 9 shows the shin shell attached to a shin guard 929.

Although not necessary, it is contemplated that some embodiments of the assembly can be capable of being integrated with a patellar control-open patellar donut as prescribed. In these embodiments, the assembly may include straps for patellar subluxation that stabilizes the elastic cross strap or hinges.

Although the above description and terminology of the components of the embodiments above utilize the terminology of a knee, it is understood and contemplated that the assembly can be applied to other joints. For example, and not for limitation, embodiments of the assembly can also be used with a person's elbow, back, shoulder or ankle. Such embodiments of the brace assembly are shown in FIGS. 12-16. For these other embodiments, the terms "upper" and "lower" such as in describing the mounting units, are still used to mean mounting units on sides of a joint whether they are on opposite sides or relatively higher or lower relative to the joint or not. For example, in braces used for a shoulder, the upper mounting unit can be mounted about the torso or shoulder of the wearer and the lower mounting unit can be mounted around the humerus. Similarly, in braces for an elbow, the upper mounting unit can be mounted about the humerus and the lower mounting unit can be mounted about the radius and ulna. In braces for an ankle, the upper and lower mounting facilities may both be above the ankle, but the brace may still function satisfactorily.

Additionally, for some of these alternative embodiments for joints other than knees, it is understood that the general description of the placement of the brace elements about the joint accommodates different joints and accommodates the extension/flexion resistance the brace is intended to provide. Posterior placement of the cross origin generally means on the opposite side of the extension or flexion that the brace is resisting and anterior placement of elements such as resistance points is on the same side of the body part going into extension or flexion. For example, the posterior placement of the cross origin is on the opposite (posterior) side of the extension of the elbow even though that side of an arm is generally anterior to the wearer's body when the arms are down. Similarly, the resistance points of the brace are on the same side as the extension even though that side of the arm is typically on the posterior side of the wearer's body.

Figure 12A:
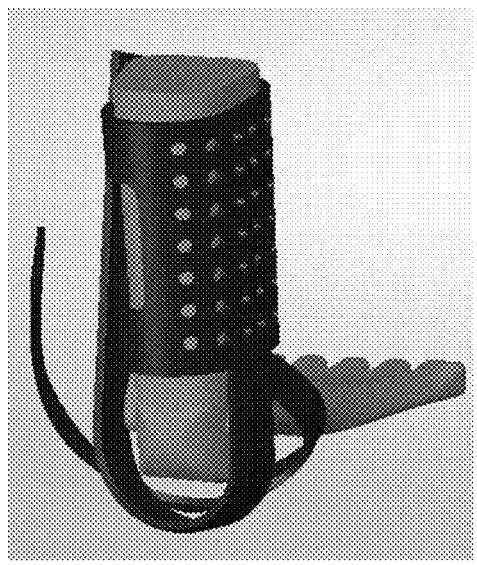
FIGS. 12A-12F illustrate different views of embodiments of an ankle brace assembly.
Figure 12B:
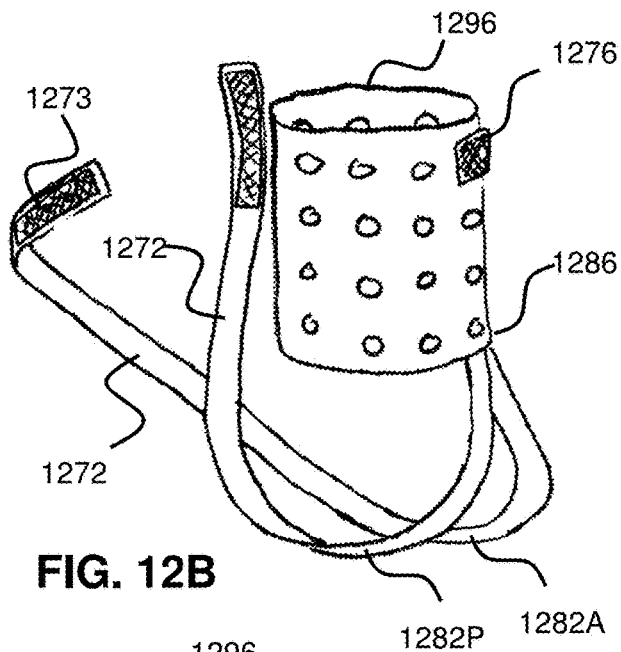
Figure 12C:
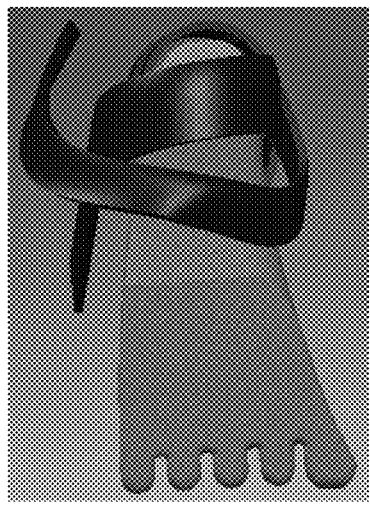
Figure 12D:
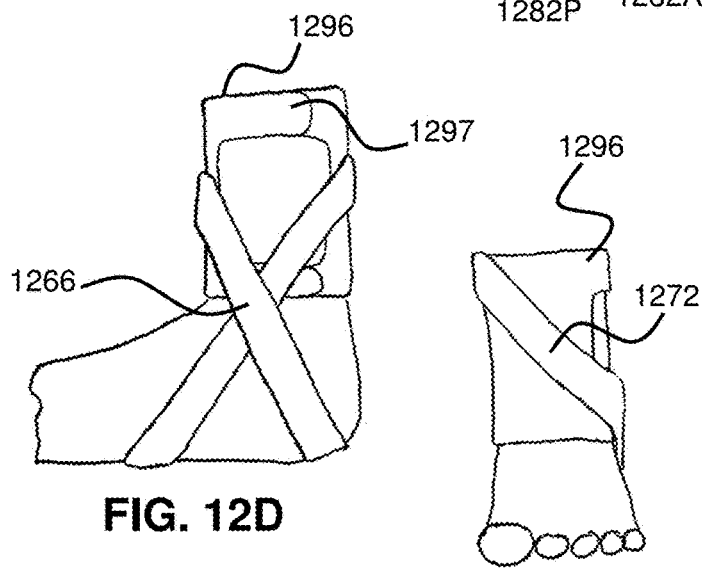
Figure 12E:
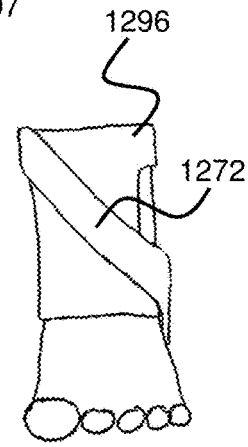
Figure 12F:
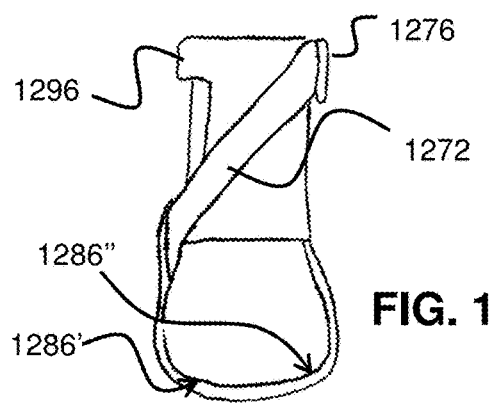

FIGS. 12A-12F illustrate one embodiment of a brace to be used on an ankle. In this embodiment, as shown in FIG. 12A, a single flexible sleeve is wrapped tightly around the lower portion of the leg above the ankle with two straps extending from the lower portion of the sleeve. The cross strap arms extend from the lower attachment point of the sleeve (lower mounting facility) through the cross origin and back to the upper attachment point of the sleeve (upper mounting facility). As illustrated in FIG. 12B, the lower portion of the cross strap arms 1282 extend from the lower attachment point 1286 and the upper portion of the cross strap arms 1272 are attached to the upper attachment point 1276 at the upper portion of the sleeve 1296 through an attachment means 1273 such as, but not limited to hook and loop fasteners, clips, buttons, snaps or any other method of attaching. FIG. 12C illustrates how the cross strap arms are positioned under the foot of the wearer. FIG. 12D shows how the cross straps form the cross origin 1266 on the lateral ankle. FIG. 12E shows a front view of an installed brace showing how one cross strap 1272 passes anterior to the leg to attach medially to the brace upper attachment point. FIG. 12F illustrates a rear view of an installed brace showing one cross strap 1272 passing posterior to the leg and attaching medially to the brace upper attachment point 1276. The positioning of the brace elements as shown, help rolling of the ankle from outside to inside. Although the eventual lower attachment point for the strap is above the ankle in some embodiments, the point of resistant force (as described above in FIG. 3A-3B) for the lower portions of the cross straps can be at a point proximal to the bottom of the wearer's foot. In this embodiment, because of the relative location of the upper and lower attachment points relative to the cross origin, the angles between the attachment points about the cross origin can be different than in other embodiments and still provide satisfactory results.

In some embodiments for the ankle, the lower mounting facility or the lower attachment point can located at or near the bottom of the wearer's foot. For these embodiments, the mounting facility may be a frictional engagement of the strap with the bottom of the foot or an additional element such as a sole pad that also attaches to the strap.

Another embodiment could include a non-elastic portion of the cross strap that extends from the bottom of the sleeve to a point proximal to the sole of the foot such that the attachment of the non-elastic portion of the strap to an elastic portion functions as the lower attachment point. An embodiment of this type may be configured so that the lower resistance point is about where the sole of the foot transitions to the medial inside of the foot.

In some embodiments of the ankle, the brace can be positioned such that the cross origin is on the medial ankle to prevent the rolling of the ankle from the inside to out. It is also contemplated that the brace can be configured so that cross strap create a cross origin on the lateral ankle as well as create a cross origin on the medial ankle to help resist rolling of the ankle in either direction.

Although the embodiment in FIGS. 12A-12D resist rolling of the ankle, it is understood that other embodiments can be used to resist other movement of the ankle. For example and not for limitation, the cross origin can also be placed above the area of the talus bone of the ankle with the upper attachment point being at a position posterior to the tibia and the lower attachment point being near the bottom of the foot to help resist dorsiflexion of the ankle.

Additional brace embodiments for the ankle are contemplated that include cuffs, frames, sleeves, hinges, struts and other elements as described herein.

Figure 13A:
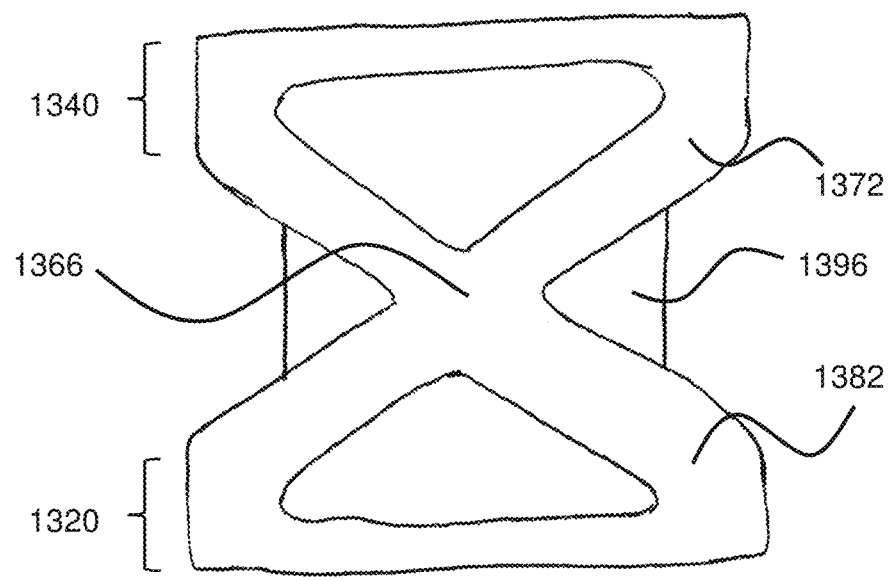
FIGS. 13A-13B illustrate one embodiment of a brace assembly for a wearer's back.
Figure 13B:
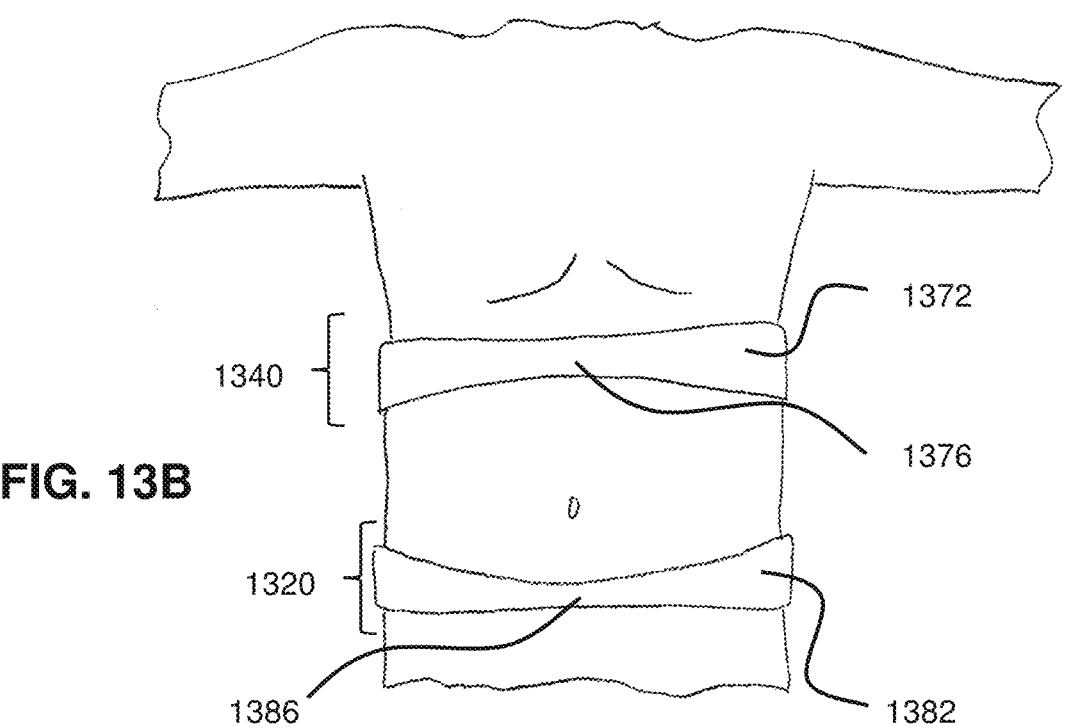

FIGS. 13A-13B illustrate an embodiment of the brace for a wearer's back where the back is viewed as a joint. FIG. 13A illustrates a rear view of a brace having a frame 1396 and a cross brace having a cross origin 1366, arms 1382 and 1372 and the arms creating the upper and lower mounting facilities 1340 and 1320. The frame helps guide the cross strap arms and provide some rigidity to help the mounting facilities and attachment points maintain their position on the back. The positioning of the cross origin in the small of the wearer's back helps resist bending forward of the wearer. As illustrated in FIG. 13A, it is understood that the cross straps can be integrated into portions of the frame (as shown) as well as be separate straps interoperating with the frame. FIG. 13B shows how the brace is mounted from the front of the wearer with the attachment points 1376 and 1386 being where the straps attach to themselves as the upper and lower mounting facilities. Additional embodiments for the back are contemplated that include cuffs, frames, sleeves, hinges, struts and other elements as described herein.

Figure 14A:
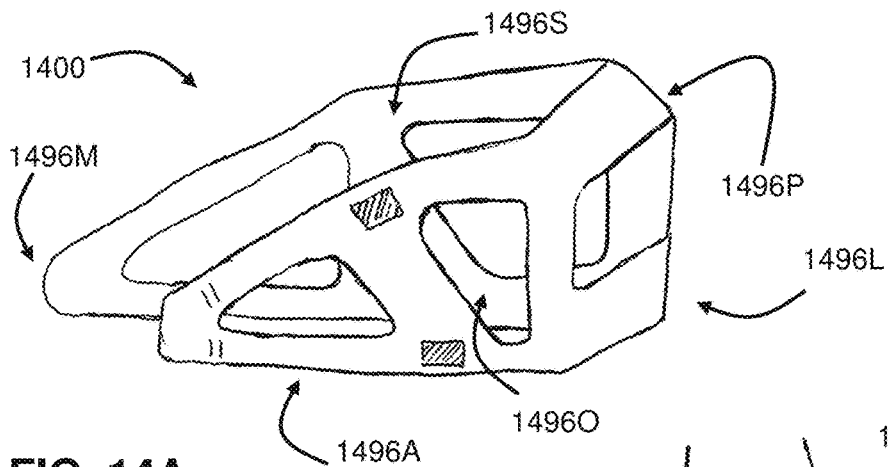
FIG. 14A-14C illustrate one embodiment of a brace assembly for a wearer's shoulder.
Figure 14B:
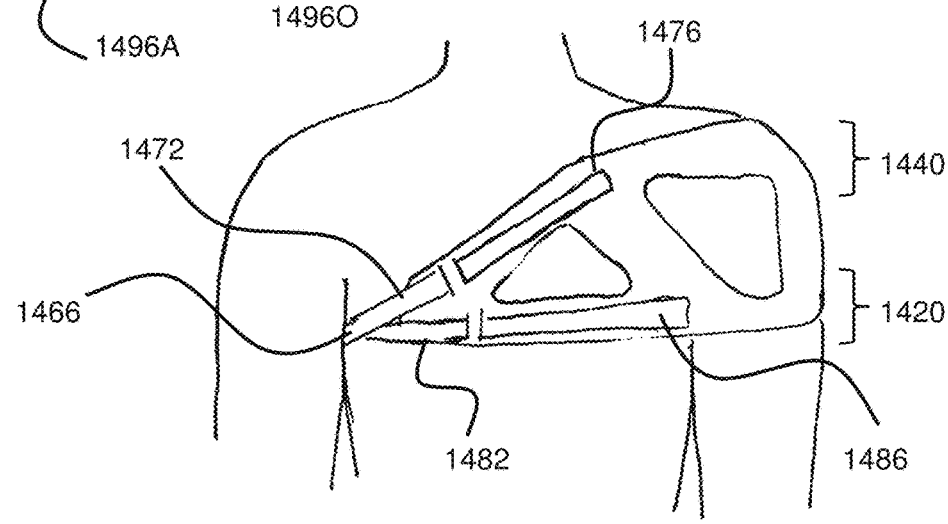
Figure 14C:
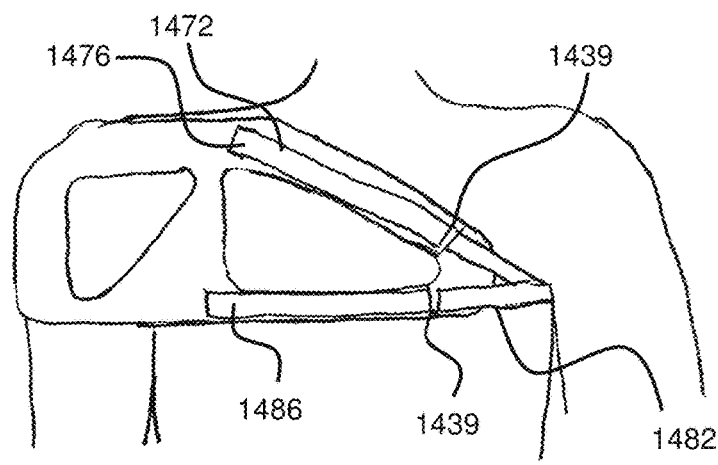

FIGS. 14A-14C illustrate one embodiment of the brace for a wearer's shoulder. As shown in FIG. 14A, the brace has a frame and attachment points for an elastic cross strap. The frame has a medial 1496M, lateral 1496L, anterior 1496A, superior 1496S and posterior 1496 (behind) portion. There are various openings 14960 designed into the brace for wearer comfort but still allow for the proper transfer of force within the brace. The positioning of this brace helps resist abduction and external rotation of the humerus. As shown in FIGS. 14B and 14C, the cross strap is configured such that a cross origin 1466 is positioned across the torso from the shoulder being braced. In this example embodiment, the cross origin is about in the axillary fossa of the user's opposite shoulder. As shown in the front view of FIG. 14B, from the cross origin 1466, cross strap arms 1472 and 1482 extend towards and attach to the attachment points 1476 and 1486 on the portion of the brace functioning as the upper mounting facility 1440 and the lower mounting facility 1420. As shown, the upper mounting facility is located above the shoulder joint and the lower mounting facility is located below the shoulder joint. As shown in the rear view of FIG. 14C, and consistent with the other descriptions herein, the cross strap arm 1472 that is attached to the lower attachment point in the front is the cross strap arm 1472 that is attached to the upper attachment point 1476 in the back and vice versa. Although not required, this embodiment contains guide rings 1439 through which the cross strap arms pass on the anterior and posterior portion of the brace to help guide the cross strap arms. Additional embodiments for the shoulder are contemplated that include cuffs, frames, sleeves, hinges, struts and other elements as described herein.

Figure 15A:
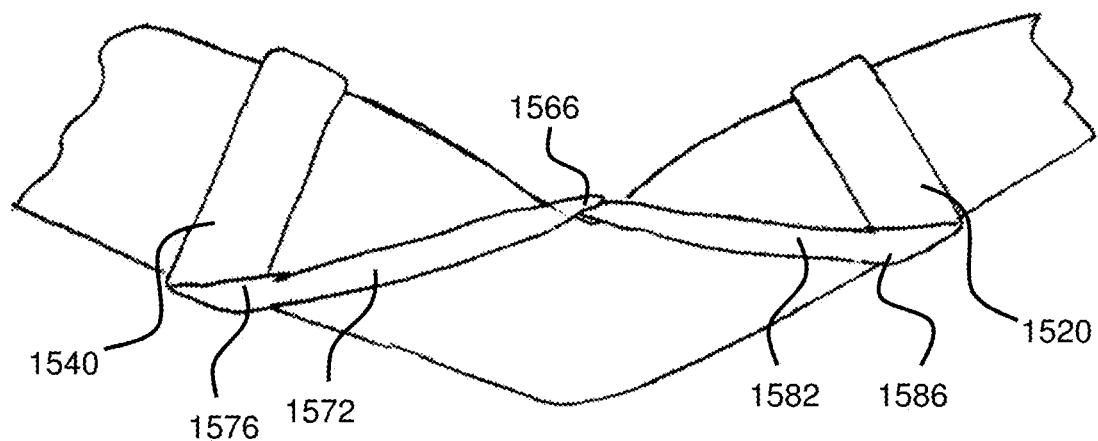
FIG. 15A-15B illustrate one embodiment of a brace assembly about a wearer's elbow.
Figure 15B:
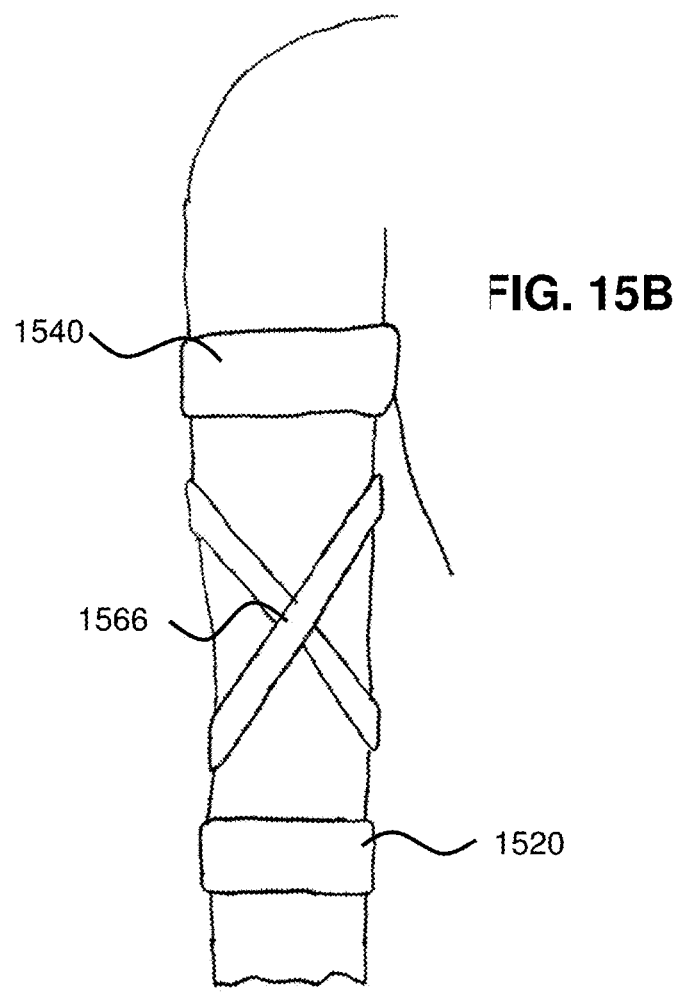

FIGS. 15A-15B illustrate one embodiment of the brace for a wearer's elbow. As shown in FIG. 15A, the brace has a cross brace having a cross origin 1566, cross strap arms and the arms create the upper and lower mounting facilities 1540 and 1520. The positioning of the cross origin in the antecubital fossa of the elbow and the strap attachment points on the other side of the arm helps resist hyperextension of the elbow. Additional embodiments for the elbow brace are contemplated that include cuffs, frames, sleeves, hinges, struts and other elements as described herein.

Figure 16A:
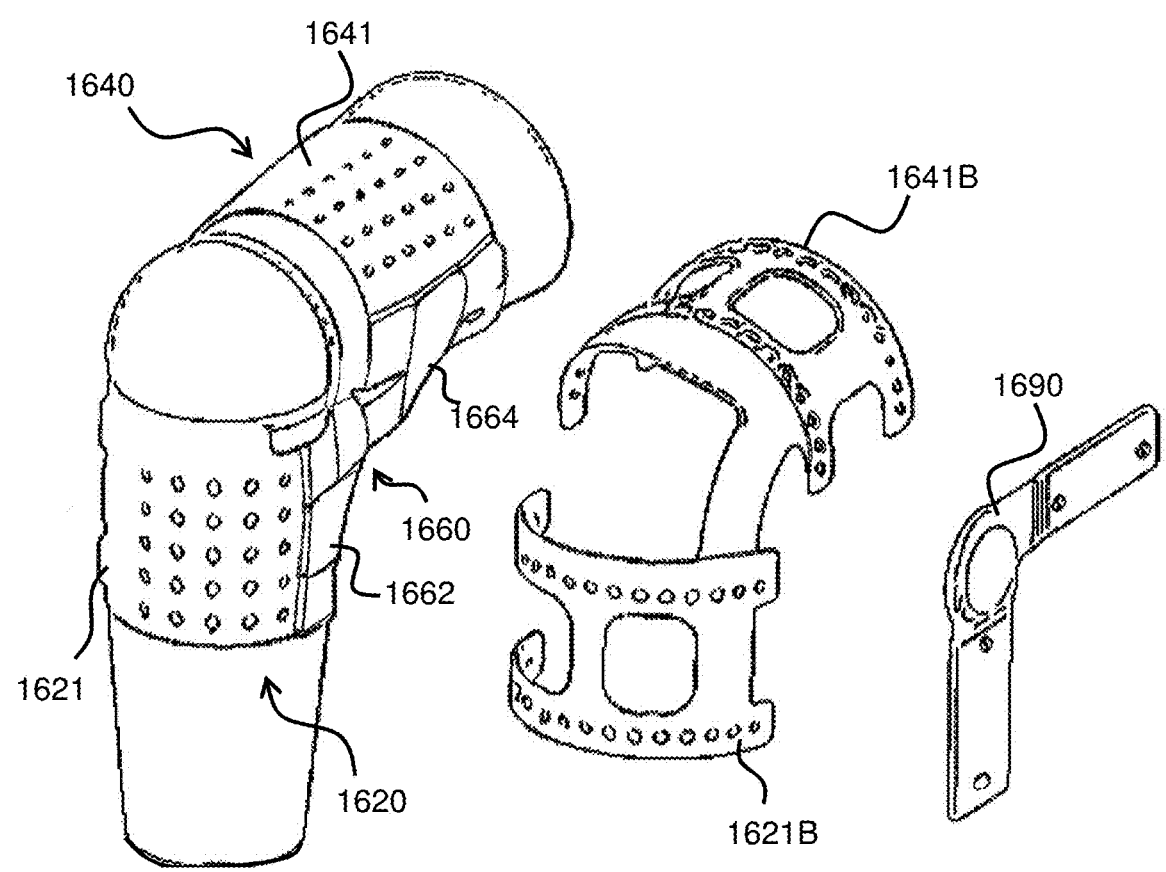
FIG. 16A illustrates an exploded view of another embodiment of a brace for a wearer's knee.
Figure 16B:
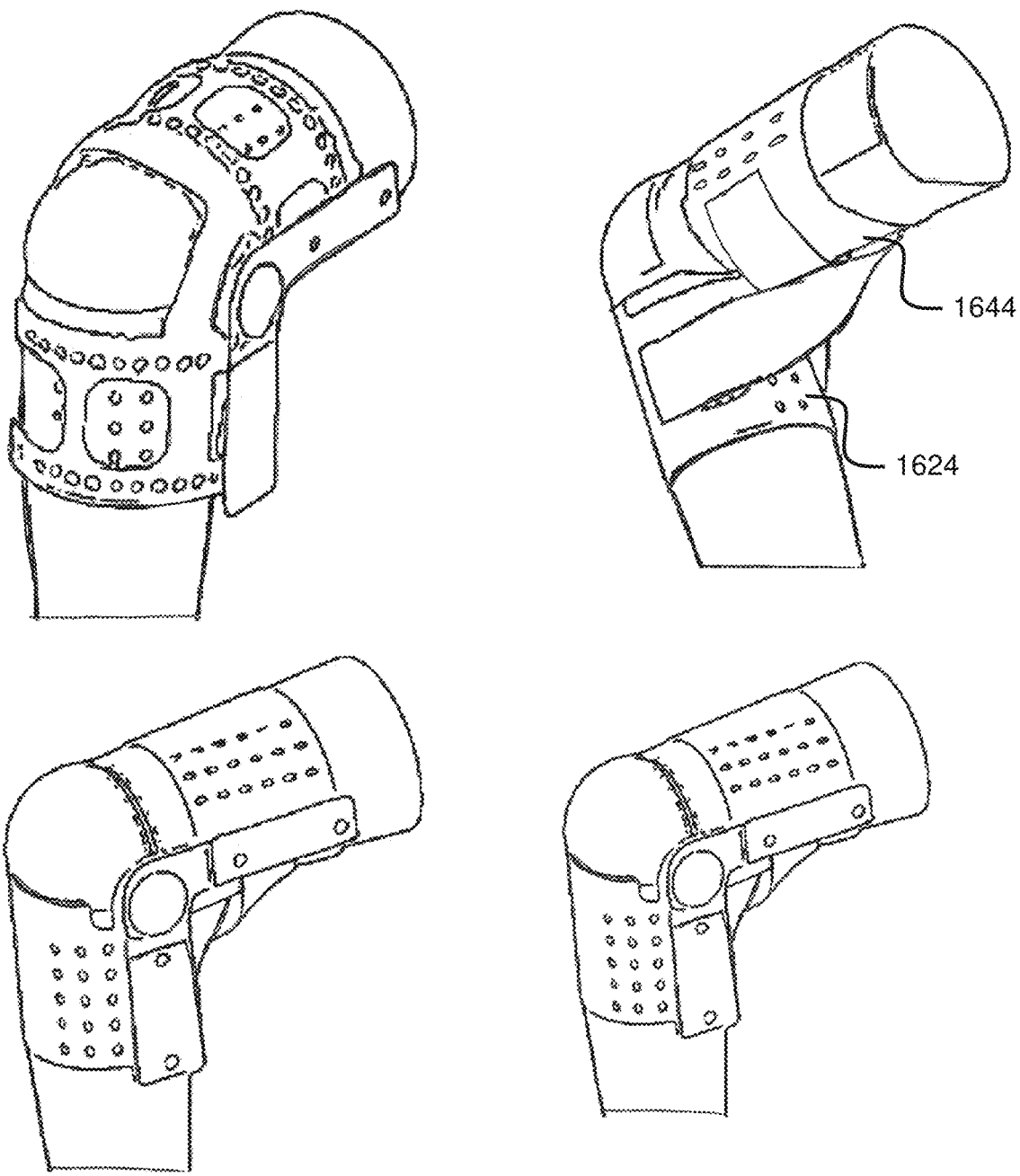
FIG. 16B illustrates different views of the embodiment of FIG. 15A for a wearer's knee.

FIGS. 16A-16B illustrate another embodiment of the brace for a wearer's knee. As shown in FIG. 16A, this embodiment has a cross strap brace with an upper mounting facility 1640, lower mounting facility 1620 and a cross strap 1660 configured to create a cross origin behind the wearer's knee to resist hyperextension. The cross strap 1660 may comprise multiple cross straps as shows 1664 and 1662. The upper mounting facility 1640 comprises an upper cuff 1641 with a portion of the cuff functioning as a strap (shown in FIG. 16B as 1644) to secure the upper cuff 1641 to the leg. The lower mounting facility 1620 comprises a lower cuff 1641 with a portion of the cuff functioning as a strap (shown in FIG. 16B as 1624) to secure the lower cuff 1641 to the leg. This embodiment may optionally also comprise an additional upper cuff brace 1641B, a lower cuff brace 1621B and a hinge 1690 capable of connecting the cuff braces. FIG. 16B illustrates how elements of this embodiment are positioned relative to each other and the wearer's knee.

Figure 17A:
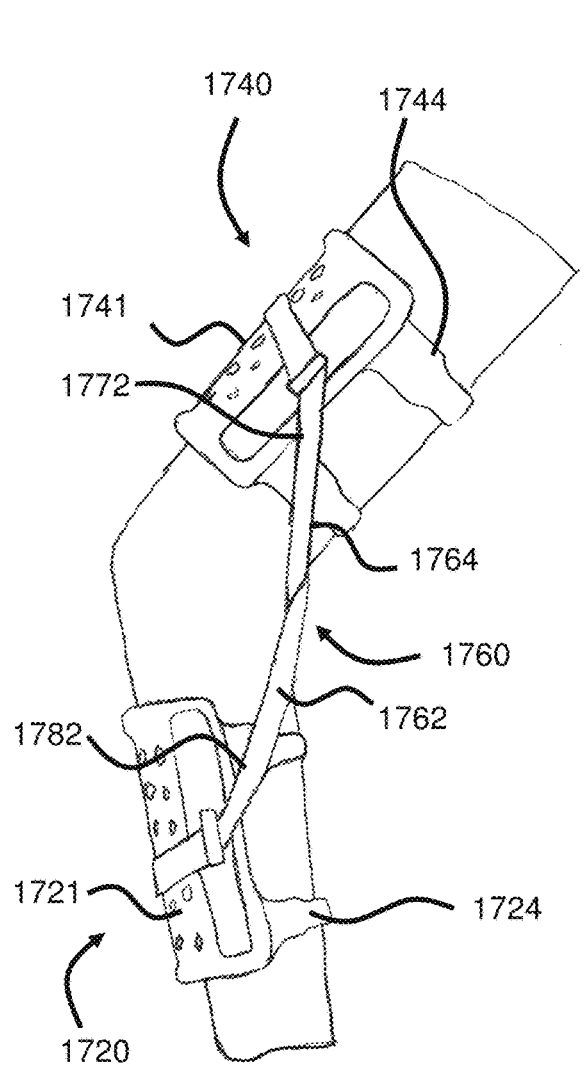
FIG. 17A illustrates a medial view of an example embodiment of a brace for a wearer's knee.
Figure 17B:
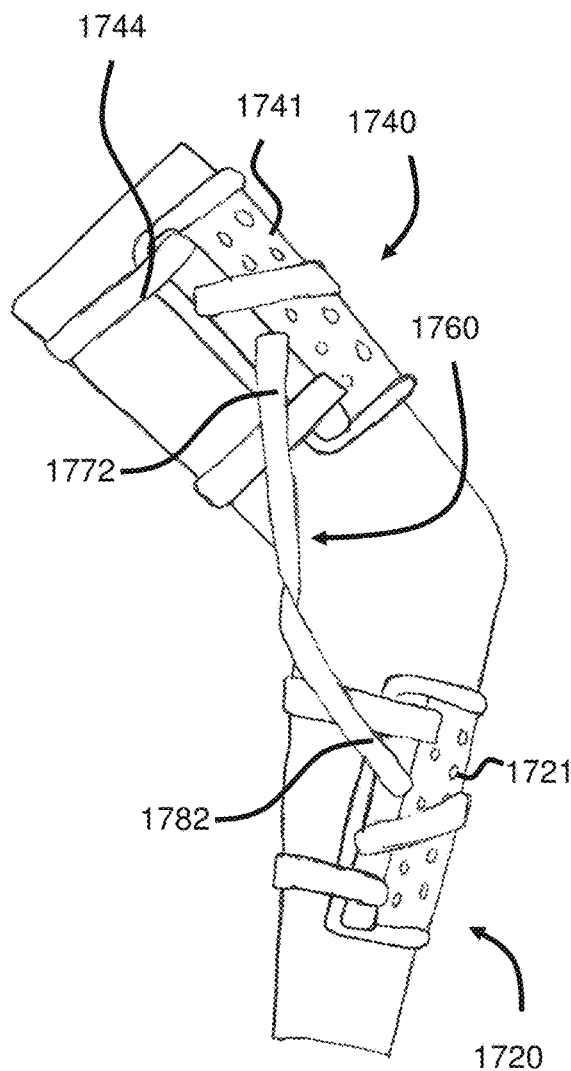
FIG. 17B illustrates a lateral view of an example embodiment of a brace for a wearer's knee.

Additional embodiments of the brace assembly are shown in FIGS. 17A-17F and 18. Although these example embodiments are illustrated through the use of the brace assembly on a knee joint, it is understood that some of these embodiments, as some of the above embodiments, may also be used on other joints such as but not limited to the back, ankle, shoulder and elbow. Referring to FIGS. 17A-17D, in these additional example embodiments, the elastic hyperextension cross strap 1760 comprises two elastic straps 1762 and 1764 each having an upper arm 1772 and a lower arm 1782. The upper mounting facility 1740 comprises an upper elastic pad/cuff 1741 and one or more elastic securing straps 1744 to secure the upper elastic pad to the leg. The lower mounting facility 1720 comprises a lower elastic pad/cuff 1721 and at least one elastic securing strap 1724 to secure the lower elastic pad/cuff 1721 to the lower leg. The elastic hyperextension cross straps 1762 and 1764 attach to the upper and lower mounting facilities whereby the elastic cross straps provide progressively increasing resistance to the extension of the user's knee when the elastic cross straps are properly positioned posterior to the user's knee. In some embodiments, as shown in FIG. 17B, the elastic cross strap is coupled to the mounting facilities as an attachment point lateral or medial to an anterior point of the mounting facility. As shown, lower arm 1782 is attached to a point of the lower mounting facility 1720 at a point lateral to the anterior point of lower mounting facility 1720. Although not required, in these embodiments, the upper and lower mounting facility are separate elements defined by portions of brace elements cooperating with the elastic cross strap.

Figure 17C:
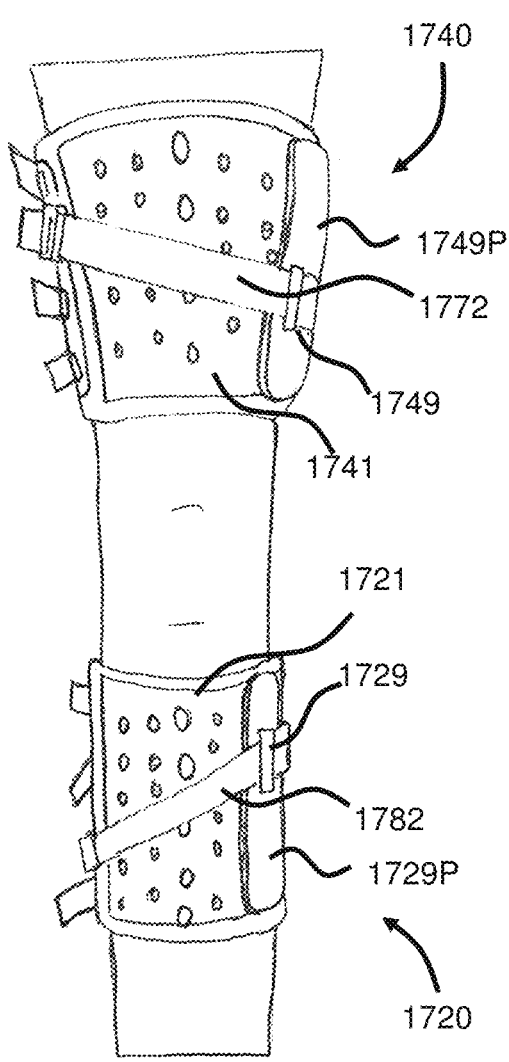
FIG. 17C illustrates an anterior view of an example embodiment of a brace for a wearer's knee.
Figure 17D:
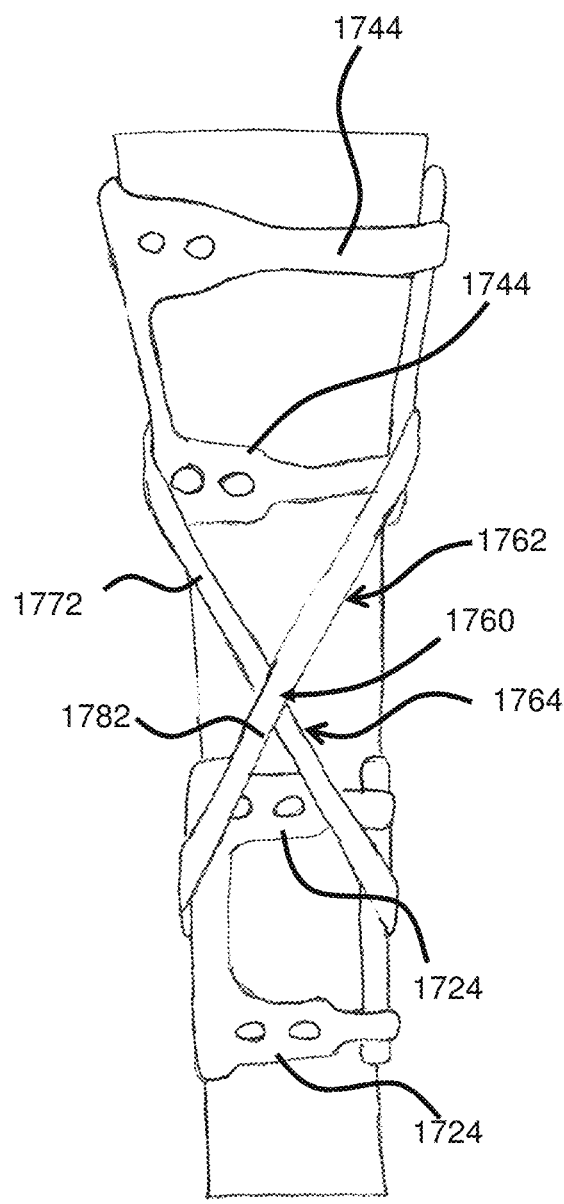
FIG. 17D illustrates a posterior view of an example embodiment of a brace for a wearer's knee.
Figure 17E:
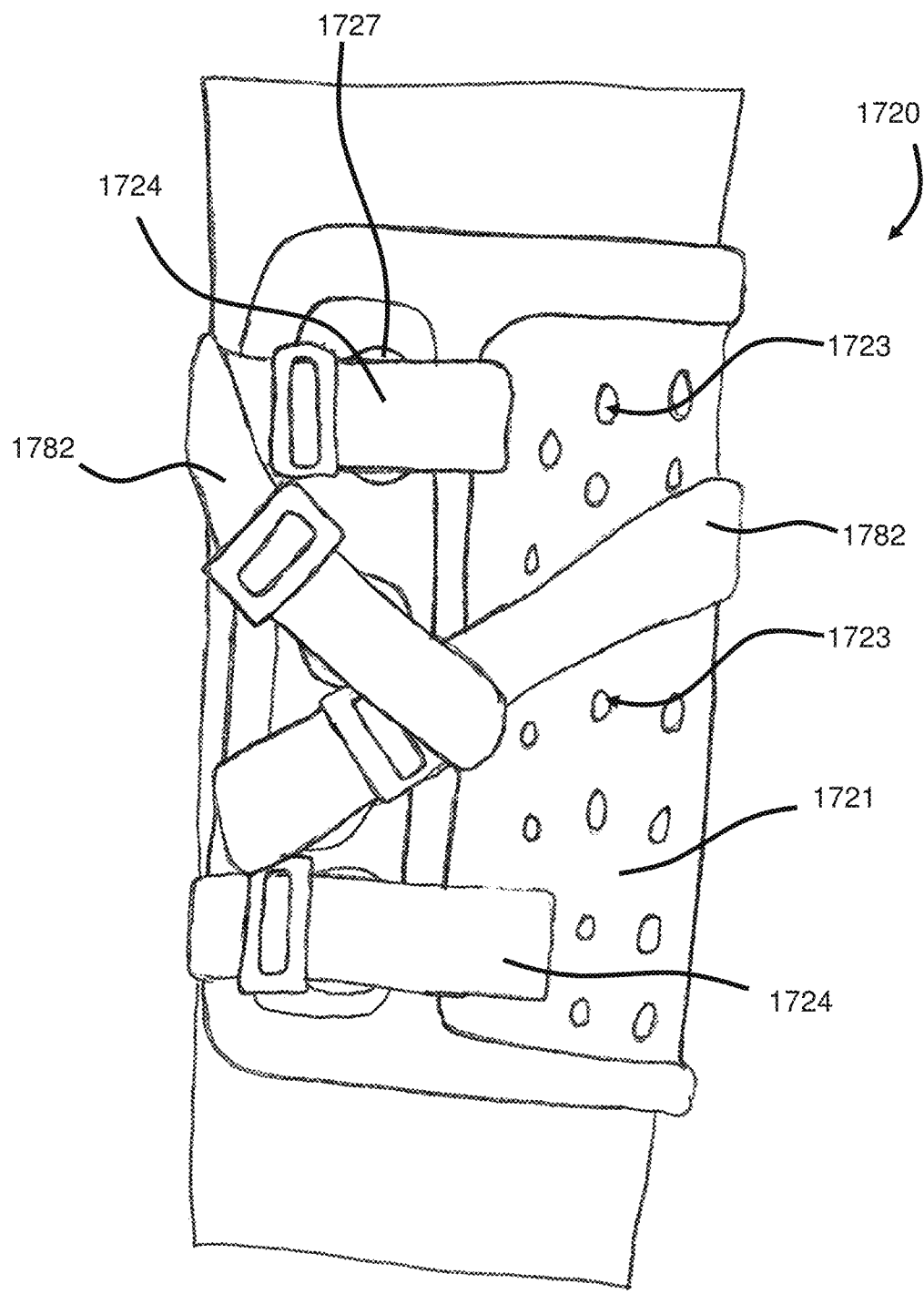
FIG. 17E illustrates a lateral view of an example embodiment of lower mounting facility for a brace for a wearer's knee.

FIGS. 17C and 17D further illustrate example embodiments as viewed from positions posterior and anterior to the brace worn on a knee. As shown in FIG. 17C, some embodiments also include an additional guide 1749 and 1729 through which the arms of the cross straps pass to help keep the cross straps positioned during use. The guides 1749 and 1729 may be part of the cuffs 1741 and 1721 or they may be part of reinforced guide pads 1749P and 1729P as shown. The guide pads may be made of the same material as the upper and lower cuffs and be removably or permanently coupled to the cuffs.

Referring to FIG. 17 E, the lower mounting facility 1720 comprises a lower pad/cuff 1721 which may have interspaced openings 1723 through the thickness of the cuff. As shown, one embodiment of the openings 1723 are through holes extending through the thickness of the mounting facility to increase friction and to allow perspiration to escape from under the mounting facility. Also shown in this embodiment are strap buckles 1727 to secure the straps 1724 to the mounting facility. Suitable buckles 1727 for embodiments include, but are not limited to, those disclosed in pending U.S. patent application Ser. No. 13/654,476 filed on Oct. 18, 2012 and US Pub. No. 20130097826 published Apr. 25, 2013, which is herein incorporated by reference in its entirety.

Figure 17F:
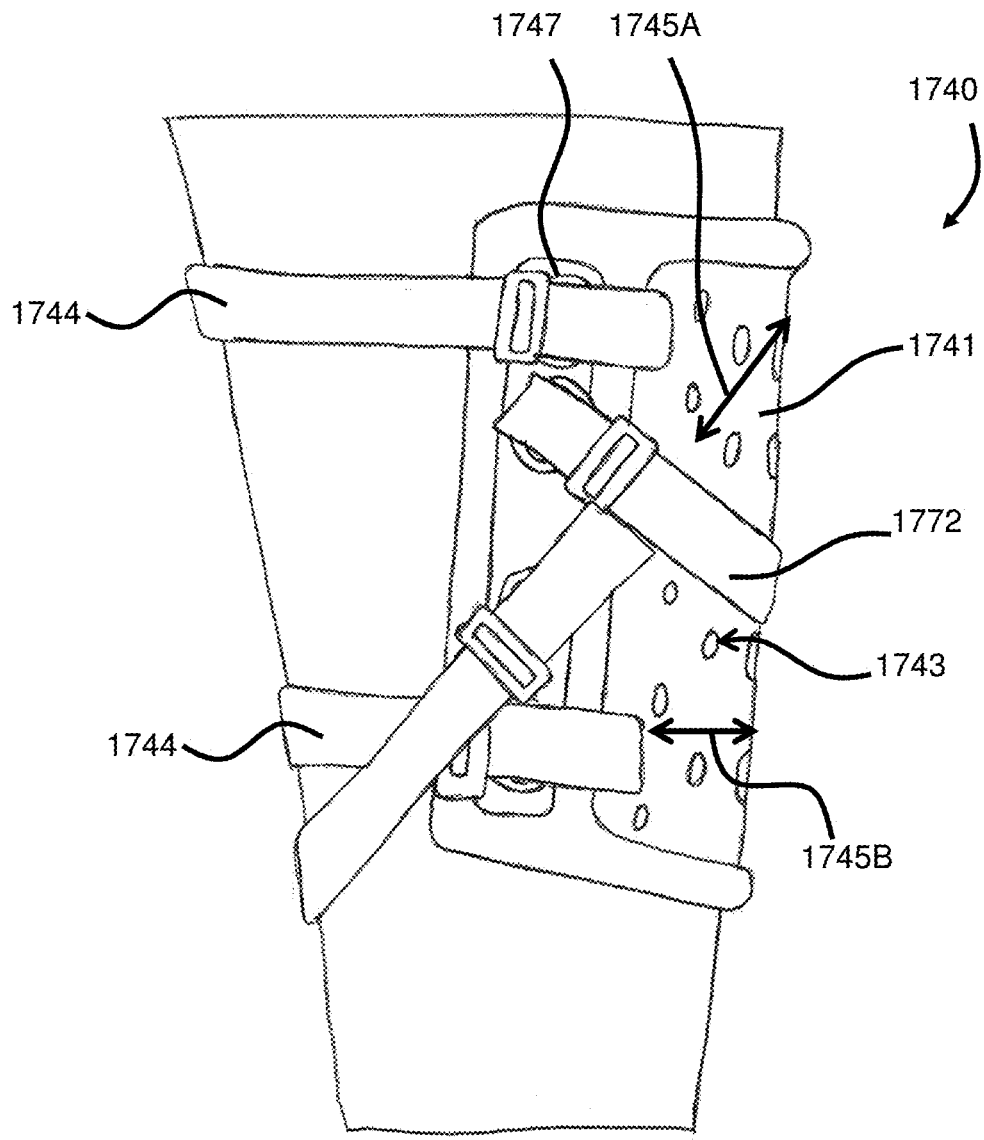
FIG. 17F illustrates a lateral view of an example embodiment of an upper mounting facility for a brace for a wearer's knee.

Referring to FIG. 17F, the upper mounting facility 1740 comprises an upper pad/cuff 1741 with interspaced openings 1743 through its thickness. The openings 1743, buckles 1747, upper arms 1772, securing straps 1744 and other similar elements may be configured to function similar to those described for the lower mounting facility.

As shown in FIGS. 17A-17F, the mounting facilities may have openings that provide comfort and friction features such as an ability for the skin under the mounting facility to have some exposure to the outside environment and to provide some irregular surfaces on the inside of the mounting facility to increase friction with the skin and/or underclothing. As detailed in FIG. 17E, the openings 1743 may also be aligned in a manner such that the mounting facility still has non-intermittent and continuous "strips" of mounting facility material (between and uninterrupted by openings) extending along and in alignment with the direction of the resistance force that is put onto the cuff by the elastic hyperextension cross strap and/or the elastic securing straps. Arrows 1745A and 1745B show examples of these strips of continuous material.

In some embodiments, when the elastic cross strap is attached to the mounting facility at an attachment point that is a distance from the resistance point, the strips of mounting facility material are able to function as extensions of the elastic cross strap and extend the material providing the resistance force to a more ideal resistance point. For example, if the elastic cross strap was to attach to the mounting facility on a generally medial or lateral position around the knee of a leg, the continuous strips of mounting facility material may extend upward or downward from the attachment point to an anterior point on the leg and allow the resistant point of the brace to be higher and lower on the joint and in a more anterior position. The pads/cuffs may also be made from a non-elastic materials or an elastic material, similar to the elastic cross strap that allows the continuous strips to extend the elastic properties of the elastic cross strap. This can be done consistent with and with similar "strips" of mounting facility material allowing the mounting facility to provide resistance to the elastic securing straps.

The elastic cross straps may also be configured with openings. The openings in the cross straps may provide similar comfort and friction benefits as do the openings in the mounting facilities. In addition, the openings in the cross strap may allow for one design of a strap to have different resistance properties based on the size and/or the shape of the openings. For example, a similar elastic cross strap design can be made to have two resistance properties by having one size openings for one configuration and have less resistance by having larger sized openings (across the width of a strap designed to provide resistance along its length) for another configuration.

FIGS. 17A-17F also show example embodiments of buckles that may be used to attach or couple the elastic cross straps and securing straps to the pad/cuffs. The example buckles have mating elements with one secured to the strap and another element secured to the pad/cuffs. The elements on the straps allow the element to be adjusted along the length of the strap to adjust the effective length of the strap and therefore alter the resistance properties of the strap when both ends of the strap are attached to the brace assembly. As shown, the buckles may be arranged at predetermined angles that correspond to the angles of the strap attachments.

Figure 18A:
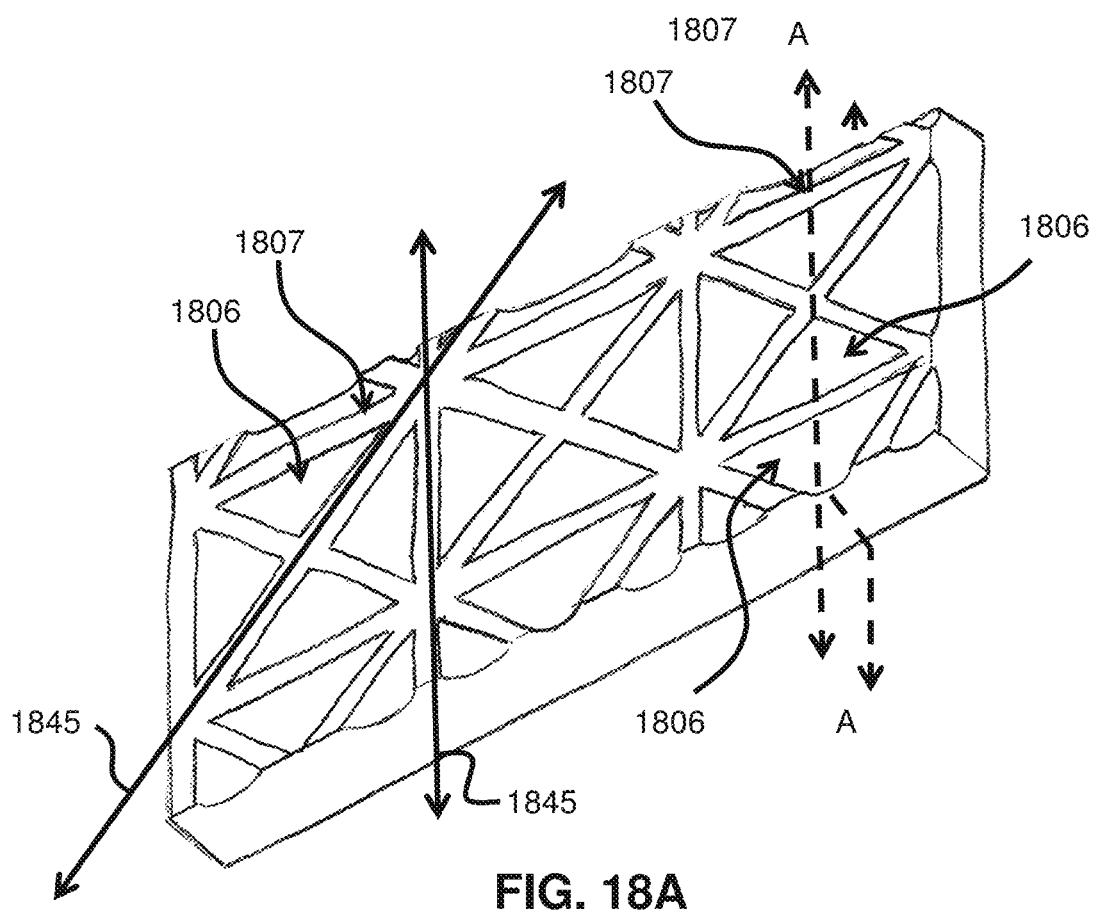
FIG. 18A illustrates one example embodiment of the under surface of a mounting facility material showing diamond shaped indentations between a flat surface, here an interlaced flat surface, that increases the friction of the brace element with the user's skin or underclothes.
Figure 18B:
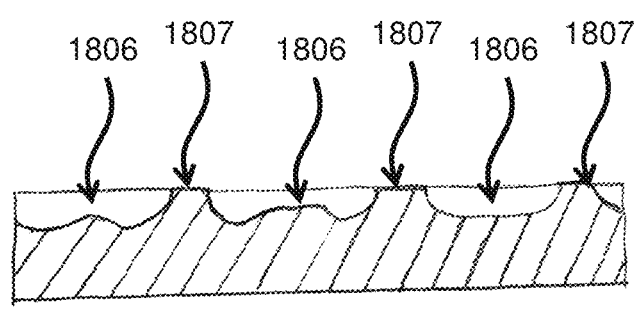
FIG. 18B illustrates a cross-sectional profile of the mounting facility material of FIG. 18A.

Referring to FIGS. 18A and 18B, one embodiment of an inner surface of brace elements is shown where the inner surface is designed to enhance the frictional engagement of the brace with the skin or underclothing of the user. As shown, the elastic material has a multiple of faced diamond shaped indentations 1806 between a generally planar surface, here an interlaced flat surface 1807, that increases the friction of the brace element with the user's skin. The diamond shaped indentations 1806 create an irregular surface and an increased surface area of the inner surface against the skin or underclothing. Additionally, the indentations 1806 allow a portion of the skin to occupy some of the space of the indentation and this irregular surface of the skin also increases the friction of the skin against the brace inner surface. As shown, the alignment of the flat surfaces 1807 may provide the non-intermittent and continuous strips of material (along arrows 1845) extending along and in alignment with the direction of the resistance force that is put onto the material to extend and/or enhance the resistance properties of the brace assembly elements. FIG. 18B shows a cross-sectional view of the material of FIG. 18A at section A-A. FIG. 18B illustrates the indentations 1806 and the raised surface 1807. In some embodiments, the indentations may be substituted or combined with through hole openings to enhance the frictional engagement of the material and to enhance breathability of the cuff and assembly.

In some embodiments, the brace assembly may also include adjusting facilities to allow portions of the brace assembly to be adjusted. These adjustments may be used to accommodate different users or to accommodate different situations encountered by the same user. In these embodiments, adjusting facilities may comprise a cable or lace and a tightening mechanism such that they cooperate with brace elements to move one portion of the brace assembly relative to another portion of the brace assembly. As used herein, the terms lace and cable have the same meaning unless specified otherwise. When used with the brace assembly, the cable and the tightening mechanism are able to put tension on portions of the brace. For example, in some instances the adjusting facilities may reduce the circumference of the mounting facility by wrapping the cable around the mounting facility and tightening the adjusting facilities similar to pulling a belt on both ends to provide varying degrees of tightness around your waste and using a buckle to hold the tension. In some instances, the cable is wrapped around one or more latches coupled to the mounting facilities and tightening the adjusting facilities acts like using shoe laces going thru shoe eyelets (latches) to tighten shoes on your feet. For example, the adjusting facilities may reduce the circumference of the inner surface of the mounting facility by tightening the adjusting facilities and therefore making the mounting facility tighter around the thigh or calf of the wearer of the brace. Additionally, the adjusting facilities may be coupled to one or more ends of the elastic cross strap so that tightening the adjusting facilities may reduce the effective length of the elastic cross strap and therefore create greater resistance of the brace to extend.

The cable may be any type of element capable of transferring a tensile force from one portion of the brace to another. For example only and not for limitation, the cable or lace may be made be a metallic cable, a nonmetallic cable, a lace or a fabric strap. In some embodiments, the cable is a nonmetallic, non-elastic and low-friction cable.

In some embodiments, the tightening mechanism may comprise a base and a control for drawing the cable towards the base thereby providing a tensile force onto the cable and portions of the brace assembly. In some embodiments, the tightening mechanism functions similar to a ratchet or a fishing reel. The mechanism function with the control configured to rotate in relation to the base such that it rotates in one direction to tighten the cable and the ratchet secures the position of the cable throughout the rotation and prevents rotation in the other direction. An example of a cable and tightening mechanism suitable for some embodiments of the adjustable brace assembly comprises the BOA Closure System sold by Boa Technology Inc. of Denver, Colo. USA. In some embodiments, the tightening mechanism may further comprise a housing. For illustration only, and not for limitation, examples of adjusting facilities, including cables and tightening mechanisms, may be similar to the tightening devices disclosed in U.S. Pat. No. 7,992,261, filed Aug. 20, 2007 and in U.S. Pat. No. 7,198,610 filed Dec. 21, 2005 both of which are herein incorporated by reference in their entirety.

In some embodiments, for example only and not for limitation, the cable and tightening mechanism may be similar to the lace and tightening mechanisms disclosed in U.S. Pat. No. 8,277,401, filed Sep. 12, 2007; the entire contents of which are herein incorporated by reference. In some embodiments, for example only and not for limitation, the cable and tightening mechanism may be similar to the cable and adjusting mechanisms disclosed U.S. Pat. No. 8,128,587, filed Oct. 1, 2010; the entire contents of which are herein incorporated by reference.

Figure 19A:
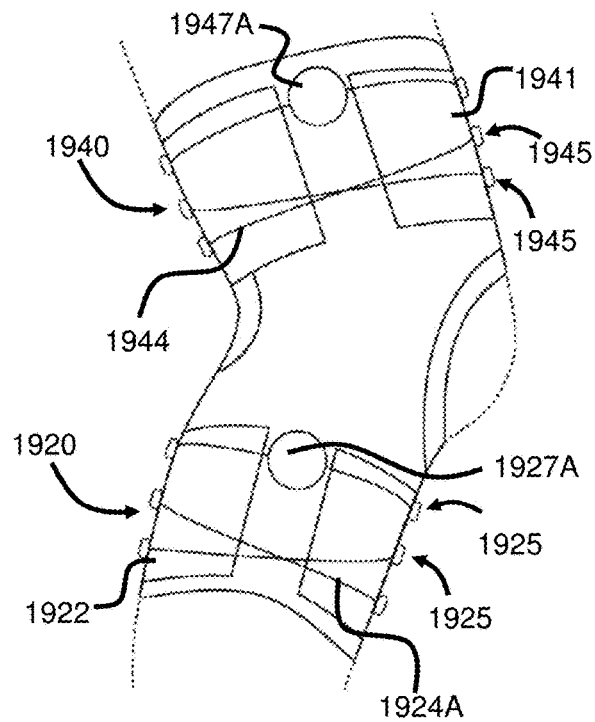
FIG. 19A illustrates a lateral view of an example embodiment of an adjustable brace assembly with adjusting facilities.
Figure 19B:
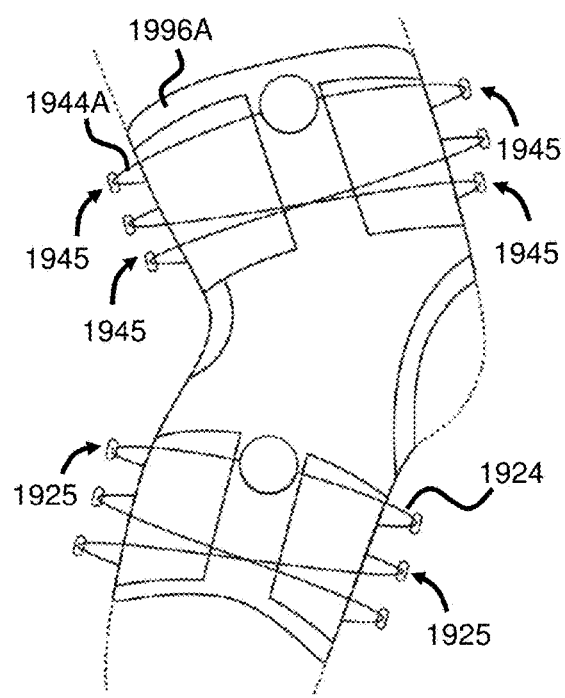
FIG. 19B shows a partially exploded view of the embodiment of FIG. 19A.
Figure 19C:
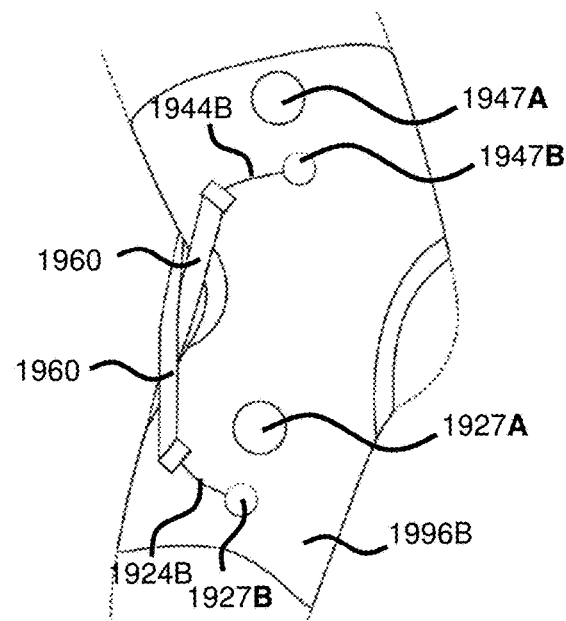
FIG. 19C shows a lateral view of an example embodiment of an adjustable brace assembly with cross straps.

Referring to FIGS. 19A-19C, some example embodiments of an adjustable brace assembly are shown. FIG. 19A shows an embodiment having two tightening mechanisms (1947A and 1927A) and cables (1944A and 1924A) on the mounting facilities (1940 and 1920) allowing independent adjustment of each mounting facilities. In this embodiment, the mounting facilities (1940 and 1920) comprise an inner sleeve 1996A and pads (1941 and 1942). The cables 1944A and 1924A are spiraled around the mounting facilities and through one or more eyelets (1945 and 1925) and at least one end is attached to the tightening mechanism (1947A and 1927A) so that the effective length of the tensioned cable 1944A and 1924A around the mounting facilities is shortened as the tightening mechanism is turned. The effective length of the tensioned cable 1944A and 1924A is the length of the cable that provides tension on the mounting facilities. For example, the cable (1944A or 1924A) may be anchored or otherwise coupled to the brace assembly at one end and the other end may be coupled to the tightening mechanism (1947A or 1927A). The cable may also be anchored on both ends with the tightening mechanism positioned between them. Or the cable may have both ends coupled to the tightening mechanism as shown. As shown in FIG. 19A, in one embodiment of the upper mounting facility, the cable 1944A is coupled to the tightening mechanism 1947A with both ends of the cable 1944A extending out opposite directions through low-friction eyelets 1945 and coiling around the pad and mounting facilities to form a continuous loop. FIG. 19B shows the embodiment of FIG. 19A with the eyelets and cable "exploded" off of the mounting facilities mounting facilities to show their positioning in this example embodiment.

Figure 20A:
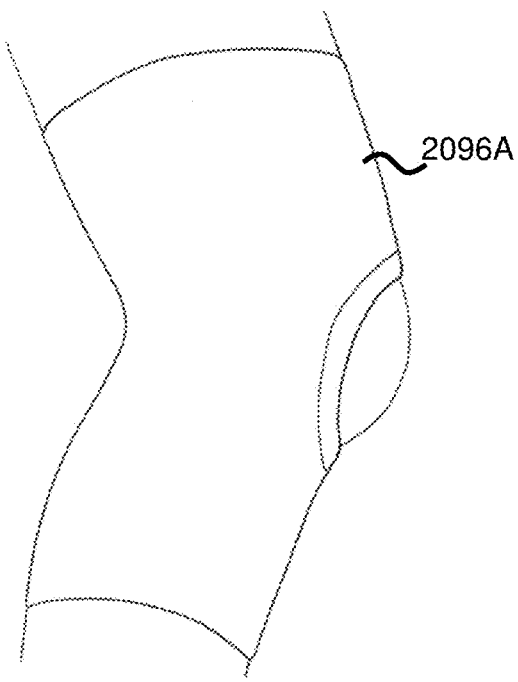
FIG. 20A shows a lateral view of an example embodiment of an adjustable brace assembly with an inner sleeve.
Figure 20B:
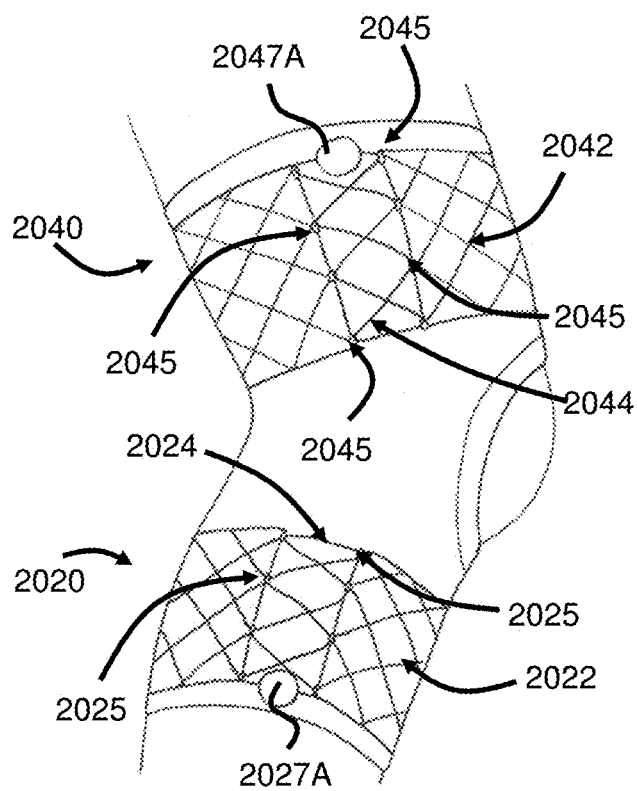
FIG. 20B shows a lateral view of an example embodiment of an adjustable brace assembly with adjusting facilities.
Figure 20C:
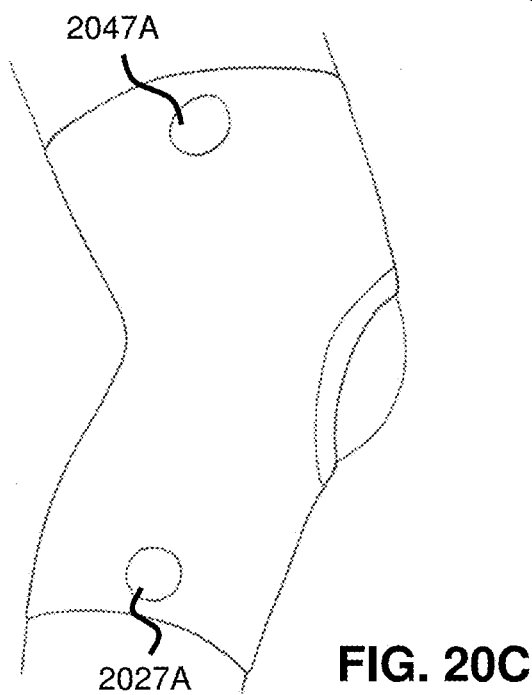
FIG. 20C shows a lateral view of an example embodiment of an adjustable brace assembly with an outer sleeve.

Referring to FIGS. 20A-20C, example embodiments of an adjustable brace assembly are shown that include a mesh material as part of the mounting facilities. In the example embodiments shown, the mounting facilities (upper 2040 and lower 2020) comprise an inner sleeve 2096A (FIG. 20A) and compression cuffs with mesh material (2042 and 2022) to assist in transferring the tension of adjusting facilities onto the mounting facilities. The mesh may be metal or nonmetal and it may be designed and fabricated with low friction conduits or passageways, here eyelets (2045 and 2025), to allow an adjusting facility comprising a cable (2024 and 2044) and a tightening mechanism (2047A and 2027A), such as disclosed with FIGS. 19A-19B, to adjust the tension on the mounting facility. The adjusting facilities allow contraction and expansion of the mounting facilities as the cables are shortened by turning the control, or knob, of the tightening mechanism to which they are attached to, causing and the eyelets (2045 and 2025) on the edge of the mesh material (2042 and 2022) are be pulled towards each other.

In some embodiments, the brace assembly may include elastic cross straps which may also have one or more adjusting facilities or the elastic cross straps may be coupled to these adjusting facilities. The configuration of the cross straps and adjusting facilities may be any configuration that allows the tension on the cross strap to be increased and decreased. In some embodiments, one end of the cross straps are coupled to an attachment point of the brace assembly on the medial side of the knee and, after passing posterior to the knee, the other end is coupled to an adjusting facility, such as a cable and the tightening mechanism, at an attachment point of the brace assembly on the lateral side of the knee. In some embodiments, the cross straps are wrapper further around the leg. For example, in some embodiments, one end of the cross straps are coupled to an attachment point of the brace assembly on the anterior side of the knee on one side of the joint, and after passing posterior to the knee, the other end is coupled to the adjusting facility, such as a cable and a tightening mechanism, at an attachment point of the brace assembly on the anterior side of the knee on the other side of the joint. Positioning the adjusting facilities on the lateral and anterior side of the joint makes it easier for a user to access and adjust the tightening mechanism.

Figure 19D:
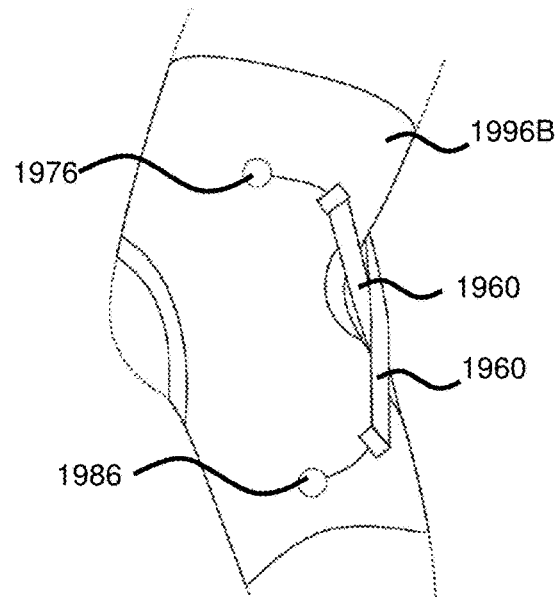
FIG. 19D shows a medial view of an example embodiment of an adjustable brace assembly with cross straps.

Referring to the example embodiment of FIG. 19C showing a lateral view on a knee, a tightening mechanism 1947B may be provided to adjust the tension on one or more cross strap 1960. FIG. 19D shows a medial view of the embodiment shown in FIG. 19C. As shown, one end of the cross strap 1960 is coupled to the attachment point on the brace assembly on the medial side of the knee (see FIG. 19D 1986) and the other end is coupled to one or more cable 1924B and the tightening mechanism 1947B at an attachment point on the brace assembly on the lateral side of the knee. In some embodiments, multiple cross straps are used. As shown, another cross strap 1960 may be coupled to attachment point 1976 and extend to cable 1924B and tightening mechanism 1927B. In this example embodiment, the cross straps 1960 are coupled to the outer sleeve 1996B. Either end of the cross strap 1960 may be rigidly or removable coupled to the brace assembly. The coupling of either end may also include a quick release type connector. In some embodiments, similar to other embodiments of the cross straps described herein, the cross strap 1960 is coupled to the brace assembly at an anterior position and wrapped around and over the fossa of the joint and coupled back to the brace at an anterior position on the other side of the joint. For example, the strap tightening mechanism 1947B may be coupled to an attachment point anterior to the joint and the cross strap 1960 is wrapped distally lateral, then posterior, then medial and anterior and coupled to an anterior attachment point below the knee. In some embodiments, another strap tightening mechanism 1927B is coupled to an attachment point anterior to and below the joint with the cross strap 1960 being wrapped proximally lateral, then posterior, then medial and anterior and coupled to an anterior attachment point above the knee. As shown, having the controls of the tightening mechanism 1947B and 1927B lateral and/or anterior allows the user to have access to the controls and therefore allows them to more easily adjust the straps. The tightening mechanisms 1947B and 1927B in this embodiment will function similar to those described above such that it will be able to adjust the tension on the cross straps 1960. In some embodiments, the cross strap 1960 may comprise an elastic portion and a more rigid portion or a coupled element that couples to the cable. Some embodiments may have a sleeve 1996B over other brace elements, such as over the cable around the mounting facilities, and include openings that still allow the tightening mechanisms 1947A and 1927A for the mounting facilities to be exposed so that the control can be manipulated.

Figure 19E:
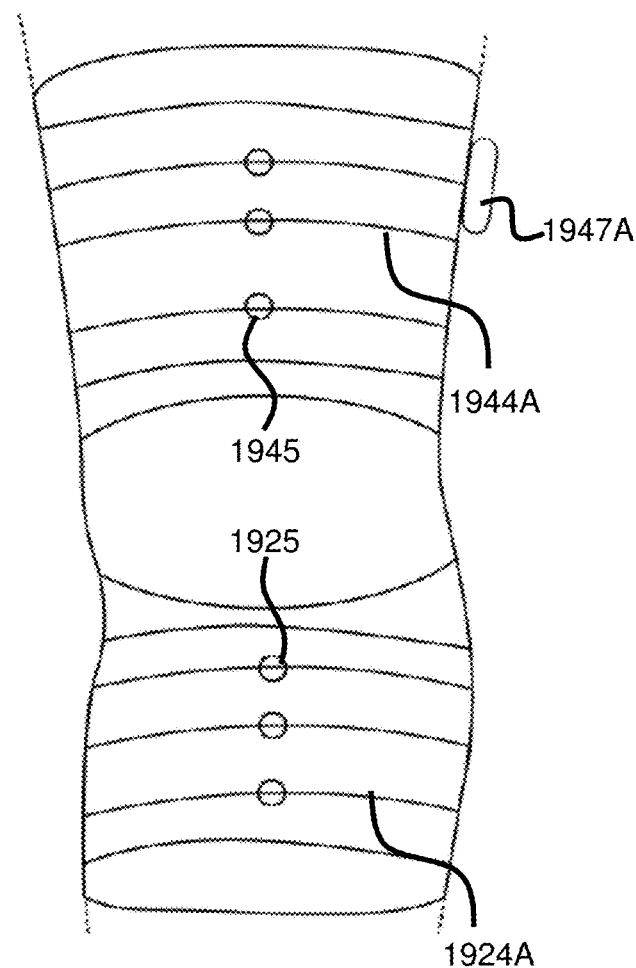
FIG. 19E shows a rear/posterior view of an example embodiment of an adjustable brace assembly with adjusting facilities.
Figure 19F:
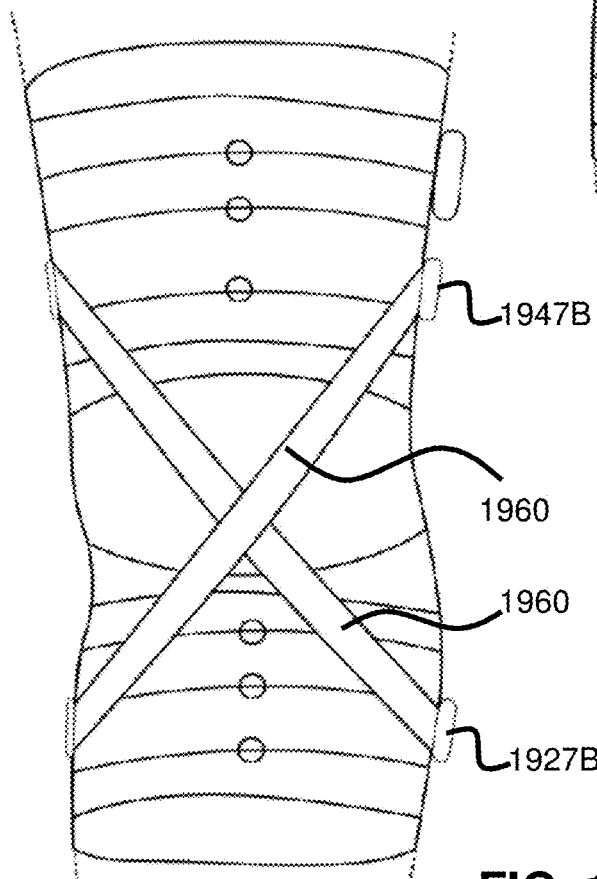
FIG. 19F shows a rear/posterior view of an example embodiment of an adjustable brace assembly with cross straps.

FIG. 19E shows a posterior view of the brace assembly with two cables 1944A and 1924A, multiple eyelets 1945 and 1925 and tightening mechanisms 1947A without the outer sleeve and without a cross strap. FIG. 19F shows a similar view of FIG. 19E with multiple cross straps 1960 and tightening mechanisms 1947B and 1927B.

It is contemplated that the embodiments of an outer sleeve with tightening mechanisms, similar to those shown in FIGS. 19C and 19D, may also be used with brace assemblies without the tightening mechanism or cables for the mounting facilities.

It is also contemplated that the embodiments with cross straps, tightening mechanisms and cables may be used with the embodiments having a mesh material as disclosed above and shown in FIGS. 20A-20C. Examples of these embodiments are shown in FIGS. 20D-20E showing the mesh 2042 and 2022, the cross strap 2060 and tightening mechanisms 2047A and 2027A.

In some embodiments, the mounting facilities may include a mesh material as a liner or as one of the materials forming the mounting facility. The mesh material may be a cylindrical, helically wound braid such as a biaxial braid, that fits around the wearer's leg as a helically wound braided sleeve. As a helically wound braid, the mesh functions like a "Chinese Finger Trap" that tightens around the wearer's leg as the ends of the mesh/cylindrical shape are pulled from each other. One of the benefits of this type of mesh design is that it helps to equalize the pressure applied by the mesh material across the surface engaged with the mesh as it tightens. This is different than the pressure that may be applied by straps or adjusting facilities that would apply pressure more locally to those areas were the straps or adjusting facilities engage the mounting facility. For example, if the mounting facilities were adjusted on a wearer's leg with two straps, the pressure on the leg may be more localized to the portion of the mounting facility that is attached to the straps. Furthermore, if the two straps had different tension applied to them, the pressure on the wearer's leg may be different at the different portions of the mounting facility that are more closely associated with each of the straps.

Figure 21:
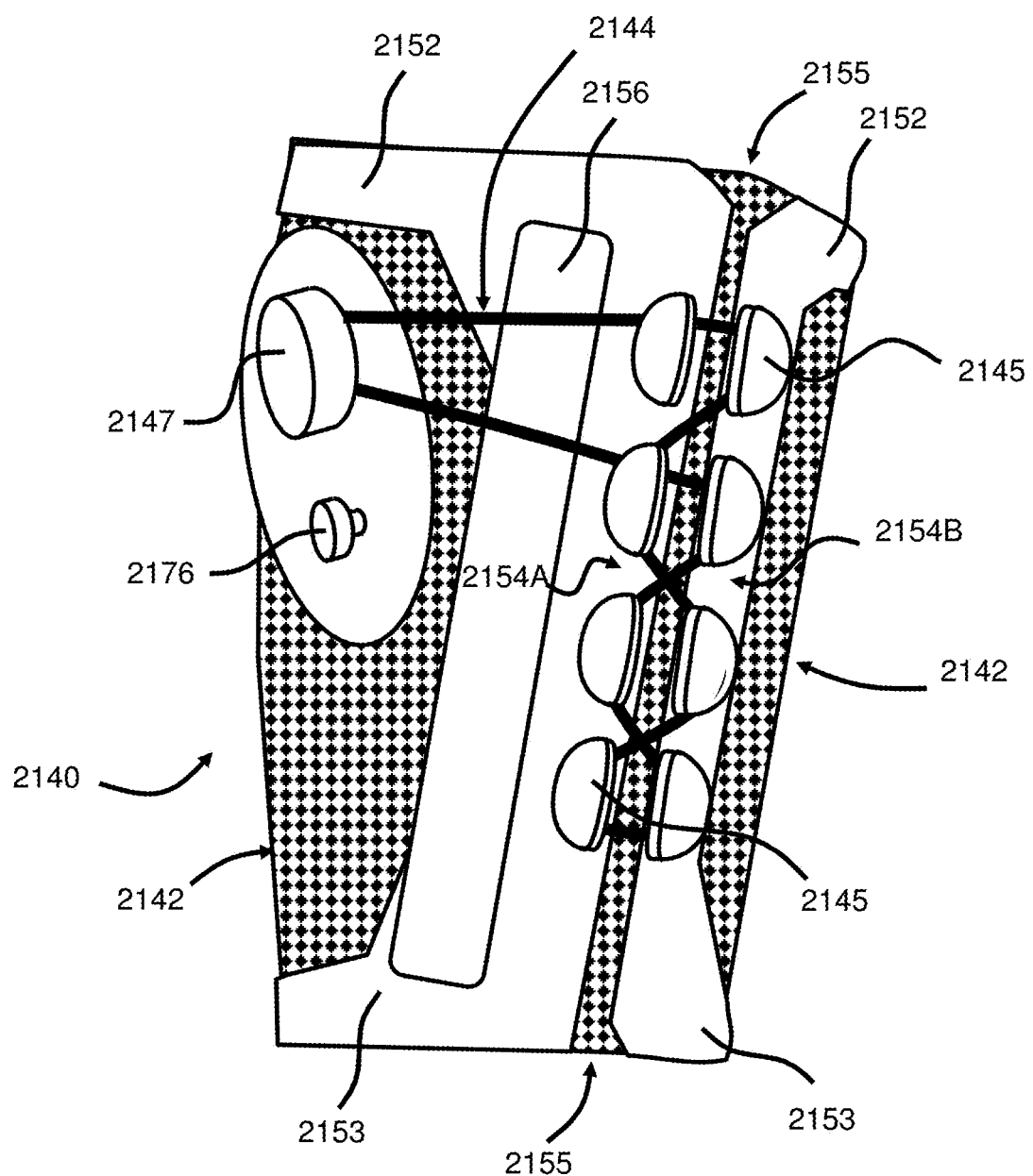
FIG. 21 shows an example embodiment of an upper mounting facility having a mesh material and an adjusting facility to adjust the inside radius of the mounting facility.

One embodiment of a mounting facility comprising a mesh material is shown in FIG. 21. As shown, the upper mounting facility 2140 comprises a mesh material 2140 and an adjusting facility comprising a tightening mechanism 2147 and a cable 2144. As shown, the mesh material 2142 comprising a helically wound braided sleeve and functions as the main material comprising the mounting facility 2140. The braided sleeve is configured as a cylindrical sleeve having a longitudinal axis, an internal radius, a distal end and a proximal end. The mesh material 2142 may or may not have a lining material. The mesh material 2142 is held in shape by being coupled to more rigid portions of the upper mounting facility 2140. The more rigid portions comprise a distal edge stiffener 2152 coupled to the distal end of the braided sleeve and a proximal edge stiffener 2153 coupled to the proximal end of the braided sleeve. Also providing some rigidity to the mounting facility are two closing edge stiffeners (2154A and 2154B) running between the distal edge 2152 and the proximal edge 2153. These stiffeners may be made of any material that provides some rigidity to the mesh to help the mounting facility 2140 maintain its shape. Additional materials, such as strut 2156 may be provided to provide additional rigidity to the mounting facility. The adjusting facility, here a tightening mechanism 2147 and a cable 2144, interoperates with multiple clasp elements 2145 on the mounting facility 2140. The cable 2144 and the tightening mechanism 2147 are configured to operably couple with one or more clasps 2145 on the upper mounting facility or the lower mounting facility, such as weaving around the clasps 2145, whereby a tightening of the cable 2144 moves the clasps 2145 to reduce the edge gap 2155 and tightens the mounting facility. The clasp 2145 is a protrusion coupled to the mounting facility 2140 that allows the cable 2144 to be weaved around them and allows the cable 2144 to slide around the clasp 2145. As the tightening mechanism 2147 pulls on the cable 2144 to make the effective length of the cable shorter, cable 2144 slides around the clasp 2145 and the inner circumference of the mounting facility 2140 gets smaller and tightens on the wearer. As shown, the cable 2144 is weaved around the clasps 2145 in a pattern that tightens the facility 2140 as the effective length of the cable 2144 is shortened. Tightening mechanism 2147 (in most uses) will be recessed or protected by a raised rim area so that the tightening mechanism will be flush with the surrounding area (not proud to the surrounding area) (see FIG. 23A).

Also shown in FIG. 21 is an attachment point 2176 for one end of the cross-strap. Another attachment point may be provided on the other side of the mounting facility to provide and attachment point for the end of another cross-strap. The attachment point 2176 is configured to receive a tensile force pulling in a proximal direction (proximal to the joint) of the mounting facility. The attachment point 2176 is coupled to the proximal edge stiffener 2153 whereby the tensile force from the proximal direction urges the proximal edge stiffener 2153 to move in the proximal direction and the braided sleeve is urged to extend along the longitudinal axis and reduce the internal radius of the braided sleeve. The attachment point may 2176 also be used to couple other elements to the mounting facility such as side paddles or patella restraints as described below.

Figure 22A:
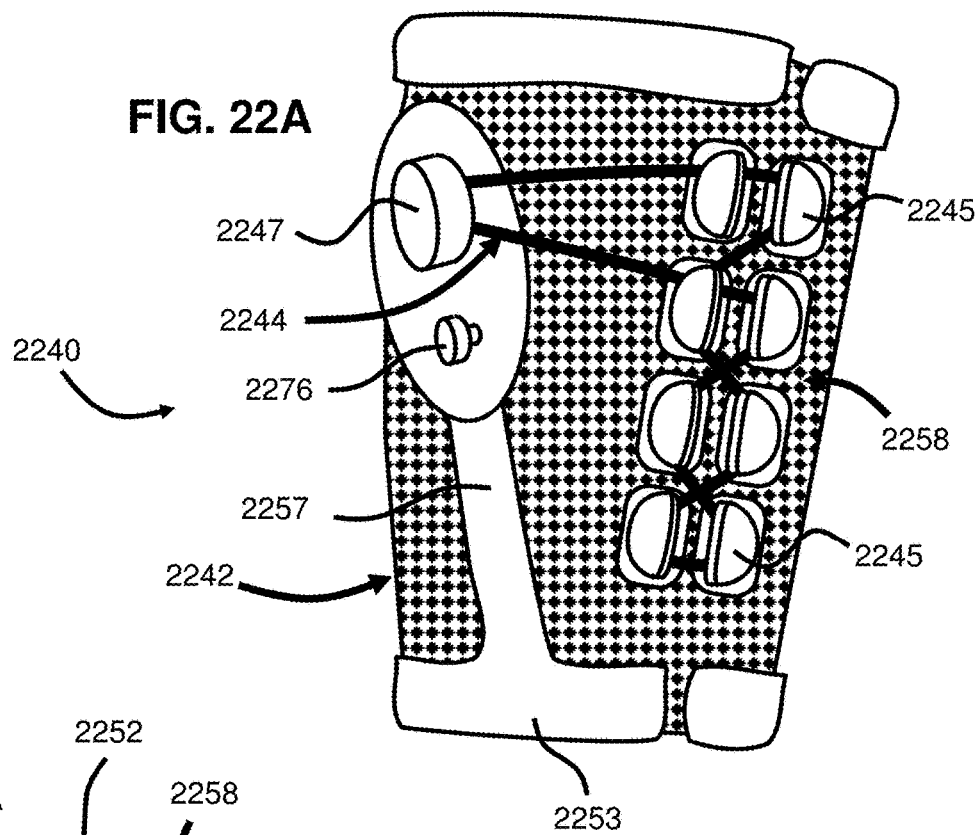
FIG. 22A shows an example embodiment of an upper mounting facility having a mesh material, a bottom stave and an adjusting facility to adjust the inside radius of the mounting facility.

FIG. 22A illustrates another embodiment of a mounting facility comprising a mesh material. This embodiment is similar to the embodiment of FIG. 21 with a few differences. This embodiment includes a proximal stave 2257 that rigidly couples the attachment point 2276 to the proximal edge 2253 of the facility. As configured, this proximal stave transfer a force (here downward) on the attachment point to the proximal edge of the facility. As a helically wound braid, the mesh contracts as it is lengthened along its longitudinal axis. This contraction increases the pressure of the mounting facility on the wearer's limb and helps to prevent a migration of the mounting facility toward the force (here towards the joint). Furthermore, this embodiment has a clasp gap 2258 that provides a space separating the clasps 2245 along the closing edges of the brace. This clasp gap 2258 allows the mesh to more freely lengthen and contract as force is applied to the proximal edge 2253.

Figure 22B:
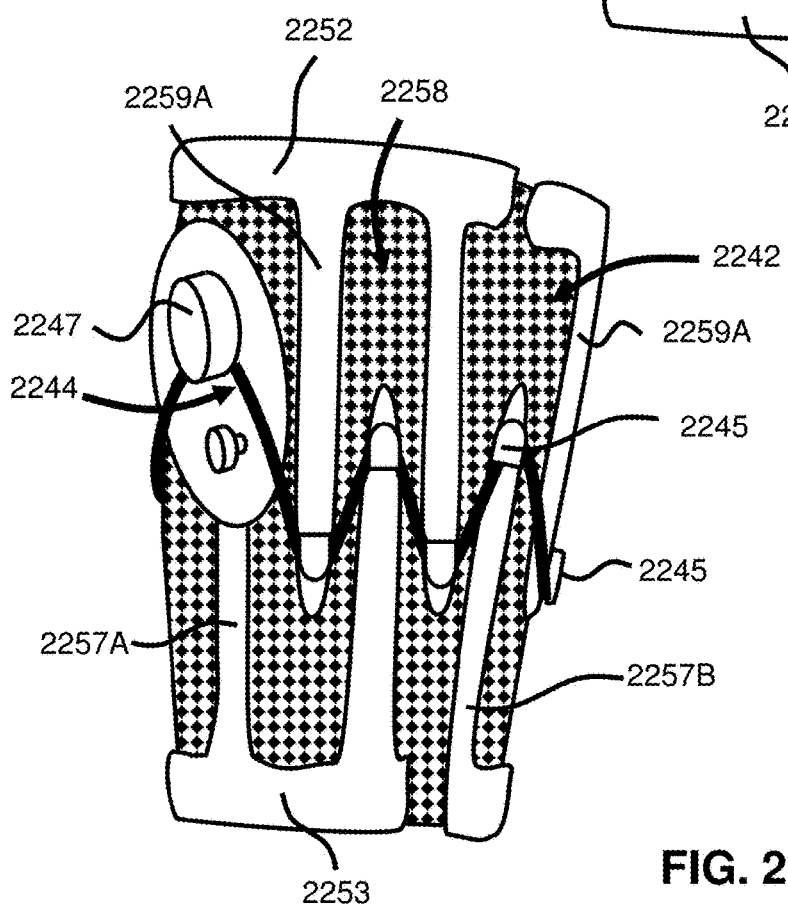
FIG. 22B shows an example embodiment of an upper mounting facility having a mesh material, top and bottom staves and an adjusting facility to adjust the inside radius of the mounting facility.

FIG. 22B illustrates another embodiment of a mounting facility comprising a mesh material and staves (2259A, 2257A and 2257B). As shown, this embodiment has a proximal stave 2257A similar to the proximal stave of FIG. 22A. This embodiment also have a series of additional proximal staves 2257B. The proximal staves 2257B are configured to transfer a force (here downward, proximal to the joint) to the proximal edge 2253. This force urges the mesh material 2242 to lengthen and contract and increase the frictional engagement of the mounting facility 2240 with the wearer's body. This embodiment also has one or more distal staves 2259A that are rigidly coupled to the distal edge 2252 of the mounting facility. These distal staves 2259A are generally configured to transfer a force (here upward) on the distal stave 2259A to the distal edge 2252. Also on some of the top and proximal staves 2257B are the clasps 2245 that allow the cable 2244 of the adjusting facility 2247 to be woven such that the adjusting facility 2247 also provides a force on the staves (2257A, 2257B and 2259A) to urge the mesh material 2242 to lengthen and contract. The cable 2244 also provides some contracting force on the mounting facility 2240 to further frictionally engage the facility to the wearer's body.

Although a lower mounting facility is not shown, similar features may be provided in a lower mounting facility to complement and be used with these embodiment of the upper mounting facility.

Some embodiments of the brace assembly may be utilized as a hyperextension prevention brace with hinges. Embodiments may be unilateral or bilateral. Embodiments may maintain position of brace on the knee sliding due to the elastic cross straps. Embodiments may be used as post-operative hyperextension prevention for ACL surgery.

Some embodiments of the brace assembly may be utilized as a hyperextension patellar-femoral brace. Embodiments may apply a hinge unilaterally or bilaterally with extension stops and the elastic cross strap design to help position the knee for patella tracking in the grove. Embodiments may apply lateral buttress and straps to apply medial force to the patella.

In some embodiments, the mounting facilities may be calibrated and configured to restrict the blood-flow to the muscles around the joint to provide the benefits referred to as "occlusion training". In these embodiments, the mounting facilities are configured to wrap around the top of a limb (proximal to the heart) at a pressure sufficient to occlude, or obstruct, blood flow to the veins but not in the arteries. A pressure from about a 70% of maximum tightness is typically sufficient to provide the benefits of occlusion training. The pressure is intended to allow the arteries to continue to deliver blood to the limb but the blood is retained in the limb since the veins cannot take it back to the heart. Occlusion training provides benefits of positive physiological adaptations at lower muscle loads which can benefit postoperative patients or patients who are unable to sustain high muscle loads due to joint pain. Occlusion training produces muscle development by reducing the oxygen supply to the muscles which results in the development/adaptation of the large fast twitch muscle fibers to handle any muscle load and allows the accumulation of compounds in the blood that simulates other beneficial reactions such as the release of human growth hormones.

In some embodiments, the cable and tightening mechanism for use with brace elements such as cross straps, training straps or patella stabilizers may be similar to the cable and tensioning mechanisms disclosed in U.S. Pat Pub. No. 2013/0184628, filed Jan. 11, 2013 to Ingimundarson et al.; the entire contents of which are herein incorporated by reference. In some embodiments, the cable and tightening mechanism for use with brace elements such as cross straps, training straps or patella stabilizers may be similar to the cable and tightening devices disclosed in U.S. Pat. Pub. No. 2014/0194801, filed Jul. 10, 2014 to Thorsteinsdottir et al.; the entire contents of which are herein incorporated by reference.

Some embodiments are capable of providing a dynamic elastic brace assembly that protects the knee by keeping it in an 'athletic position' protecting the ligaments and allowing the muscles around the knee to stabilize while protecting against muscle atrophy. These embodiments may be an alternative to taping the joint whereby there is no need to re-apply loose tape between events and no more costly continuous tape purchases. These embodiments provide an alternative to functional braces providing less slippage due to heavy, rigid structures and reduced skill limitations. Embodiments may provide extension prevention like a rigid brace but with the comfort and normal control of a taping procedure. Embodiments may be capable of being designed without metal and therefore may be used in sports that do not allow metal braces.

Some embodiments may be less costly, lighter weight, can be loosened between break times, intermissions and time-outs. Embodiments may control against knee hyperextension; a major cause of ACL tears and failure of ACL surgical repairs. Embodiments may control hyperextension by gradually increasing resistance such that the athlete experiences a "soft stop" which is more comfortable and doesn't shift the brace down the leg like a normal metal brace with hinges that creates a "hard stop". Embodiments may mimic taping procedures that have been proven to outperform expensive functional braces. Embodiments may be less expensive and less irritating than repeatedly taping the knee or purchasing a custom fit or off-the shelf functional brace for sports, thereby increasing the number of athletes of all ages that can protect their knee during sports. Embodiments may be used as a training brace by adding a hip rotation strap that will teach athletes how to properly jump and land without tearing their ACL. Embodiments may be easily removed or partially released during short and long rest periods during athletic events, unlike functional braces that have to remain applied and often taped in place to prevent slippage. Embodiments may be applied to all leg shapes and sizes without losing its effectiveness. Many body types and heavy people cannot wear a functional knee brace. Embodiments may be used on both knees at the same time for training and preventative use.

Some embodiments may also increase quadriceps muscle strength because they provide resistance to extension. Embodiments may be light weight and easy to apply. Embodiments may allow the elastic/dynamic cross straps to be inexpensively replaced after multiple uses or breakage thus maintaining the active control of knee motions. Embodiments can act as the foundation to add accessory pieces that will protect against side blows (hinged lateral paddle), unstable knee caps (lateral buttress), or shin guards for soccer and motocross. Embodiments may be comfortably worn under pants or athletic gear. Embodiments may be worn during skiing without requiring shorter ski boots or shorter less effective braces.

Figures 23A, 23B:
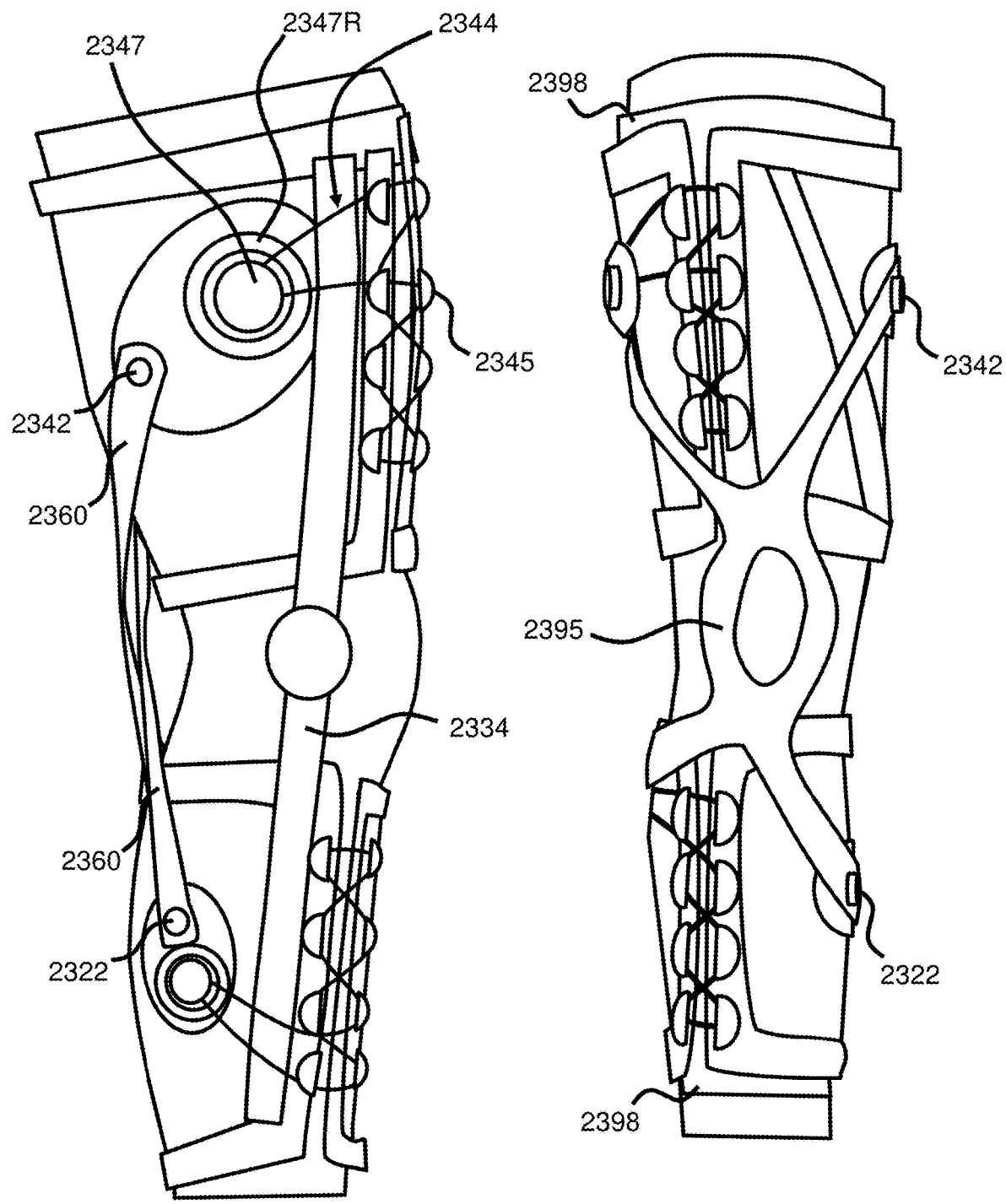
FIG. 23A shows a side view of an example embodiment of a brace assembly with a side paddle.
FIG. 23B shows a front view of an example embodiment of a brace assembly with a patella stabilizer.

In addition, some embodiments may further include additional features such as, but not limited to: side paddle with a hinge that can be added for lateral support, breathable over-sleeve, hip rotation training strap and different colors. FIG. 23A shows a side view of an embodiment of the brace assembly having two elastic cross straps 2360 and a side paddle 2334. The cross straps 2360 are attached to the attachment points (shown 2342 and 2322). FIG. 23A also shows a raised rim area 2347R which raises the area surrounding the tightening mechanism 2347 so that the head of the mechanism is not proud and is less likely to interfere with the wearer's use of the brace. As can be seen, the tightening mechanism 2347 is able to shorten the effective length of the cable 2344 around the clasps 2345 to tighten the mounting assembly on the wearer's leg. The lower mounting facility operates similarly. FIG. 23B shows a front view of an embodiment of the brace assembly having a sleeve 2398 and a patella stabilizer 2395 attached to the mounting facilities at attachment points 2342 and 2322.

Figure 23C:
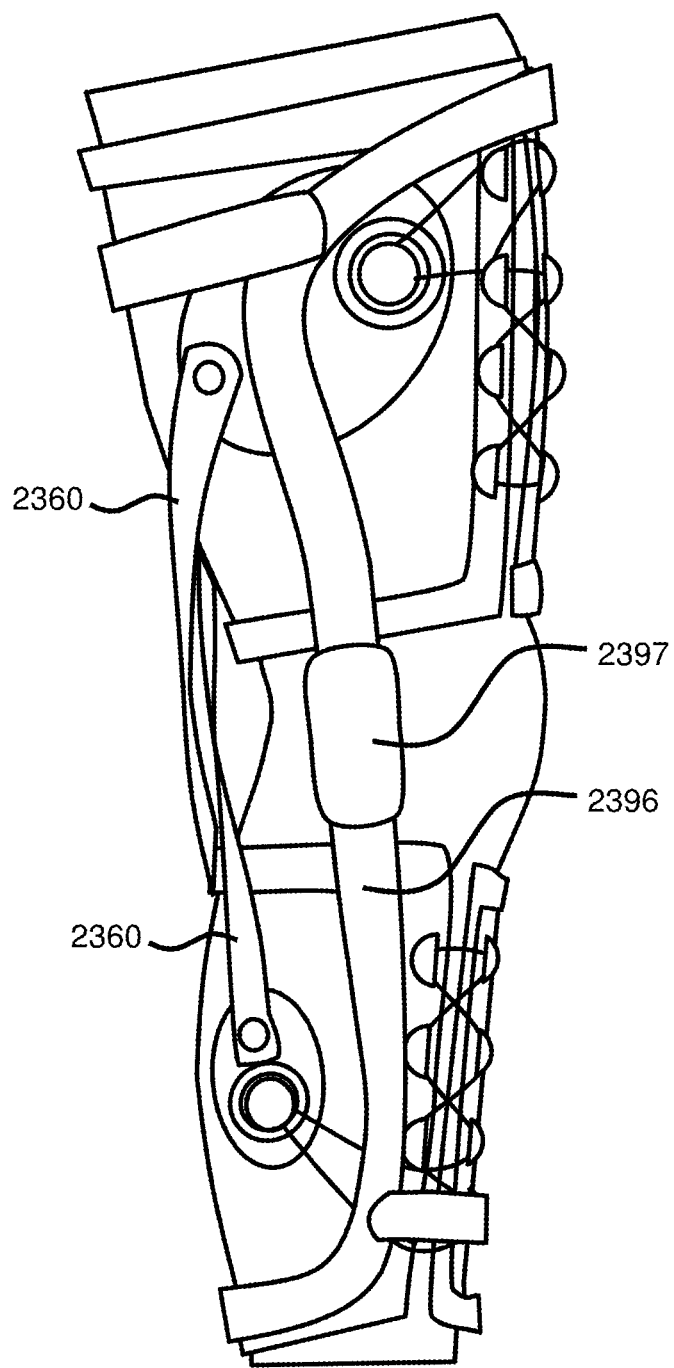
FIG. 23C shows a side view of an example embodiment of a brace assembly with a side paddle, a patella stabilizer and a hinged brace.

FIG. 23C shows a side view of an embodiment of the brace assembly have elastic cross strap 2360 and a brace 2396 and hinge 2397 where together they provide functionality similar to that of an exoskeleton.

Figure 24A:
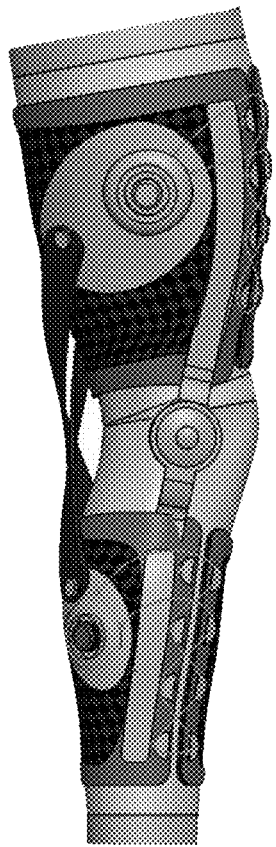
FIGS. 24A-24C show images of the example embodiments of FIGS. 23A-24C.
Figure 24B:
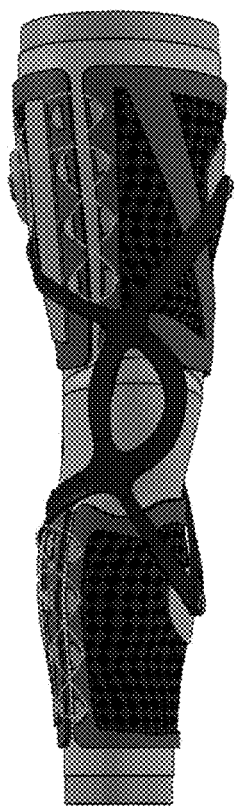
Figure 24C:
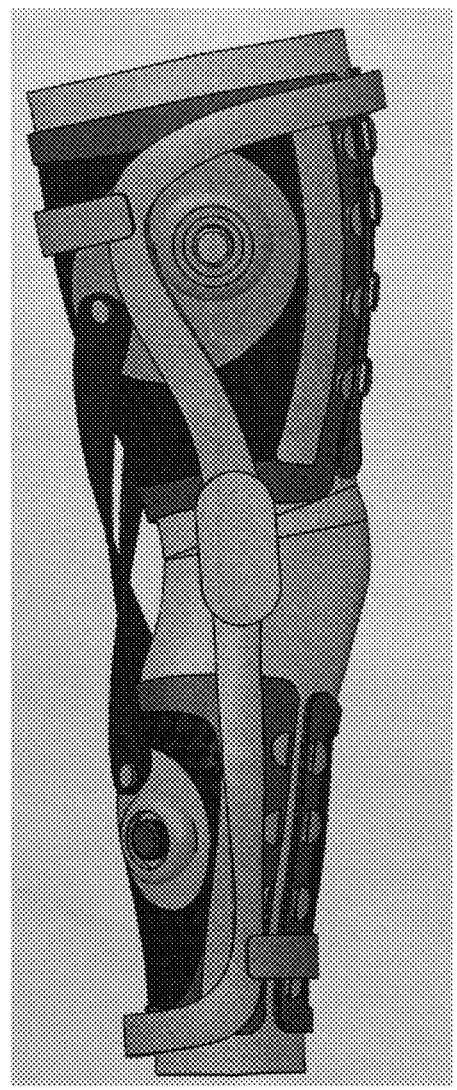

FIGS. 24A-24C show images of the example embodiments of FIGS. 23A-24C.

Figures 25A, 25B, 25C:
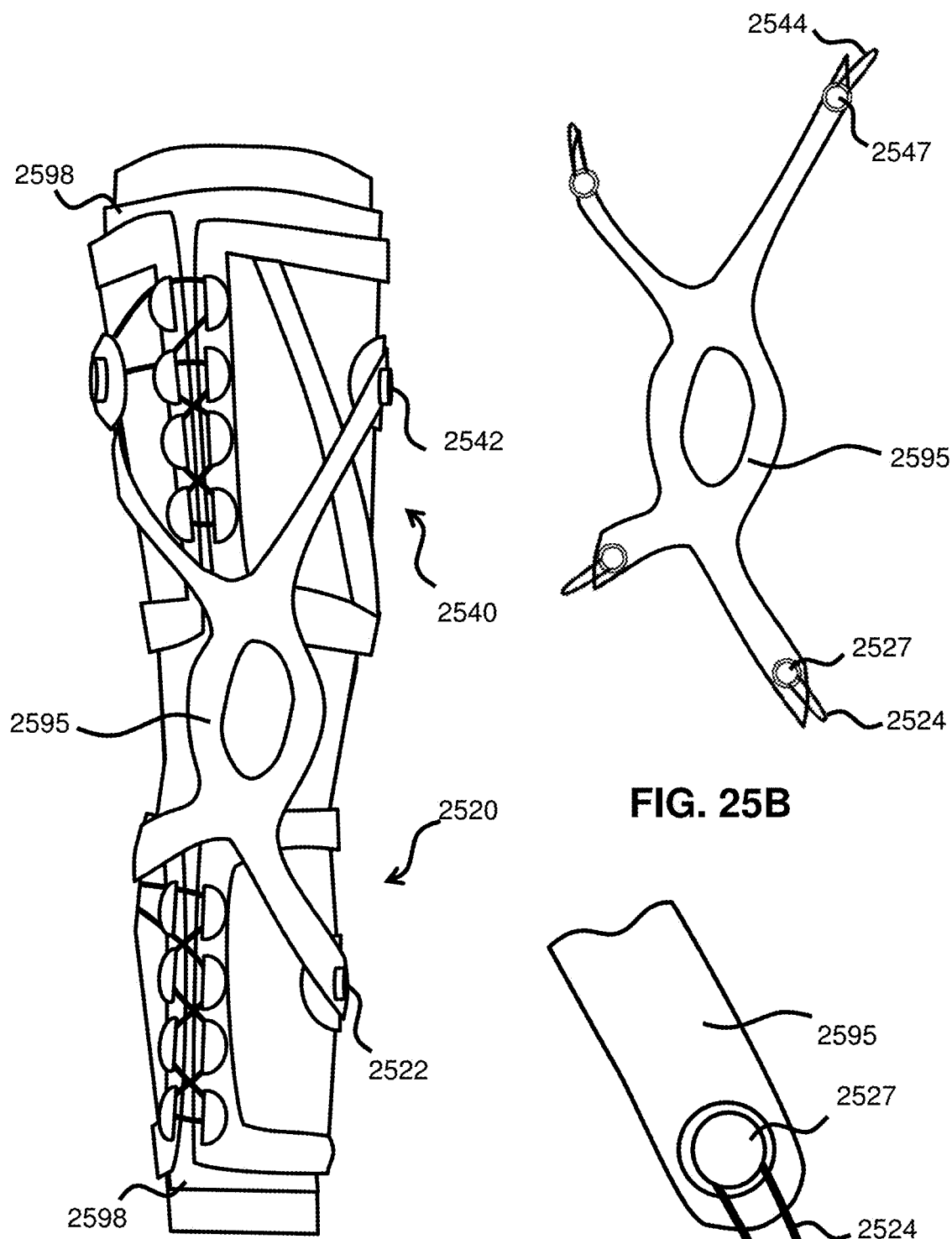
FIG. 25A shows an example embodiment of the brace assembly with a patella stabilizer.
FIG. 25B shows an example embodiment of a patella stabilizer with adjusting facilities.
FIG. 25C shows an example embodiment of an end of a patella stabilizer and an attachment point.

FIGS. 25A-25BC illustrate details of another example embodiment consistent with FIGS. 23B and 24B. As shown in FIG. 25A, the brace assembly includes a patella stabilizer 2595 which may be attached to the mounting facilities at attachment points 2542 and 5222 (lateral attachment points not shown). As shown in FIG. 25B, the patella stabilizer 2595 may have adjusting facilities comprising tightening mechanism 2547 and 2527 and cables 2544 and 2524. Similar to their use with the cross-straps, the adjusting facilities and cables are configured and positioned to allow for an adjustable tension to be applied to the patella stabilizer 2595 when the stabilizer is attached to the mounting facilities 2540 and 2520 at the attachment points 2542 and 2522 of the mount. This tension of generally provided by shortening the effective length of legs of the stabilizer so that the tension is increased. As shown in more detail at FIG. 25C, ends of legs of the patella stabilizer 2595 may have a tightening mechanism 2527 and cable 2524 that is configured to attach to attachment points on the mounting facilities, here attachment point 2522. In some embodiments, the adjusting facility may be mounted on the mounting facilities and the ends of the stabilizer use the attachment means disclosed herein to couple the stabilizer to the adjusting facilities and the mounting facilities.

Figures 26A, 26B:
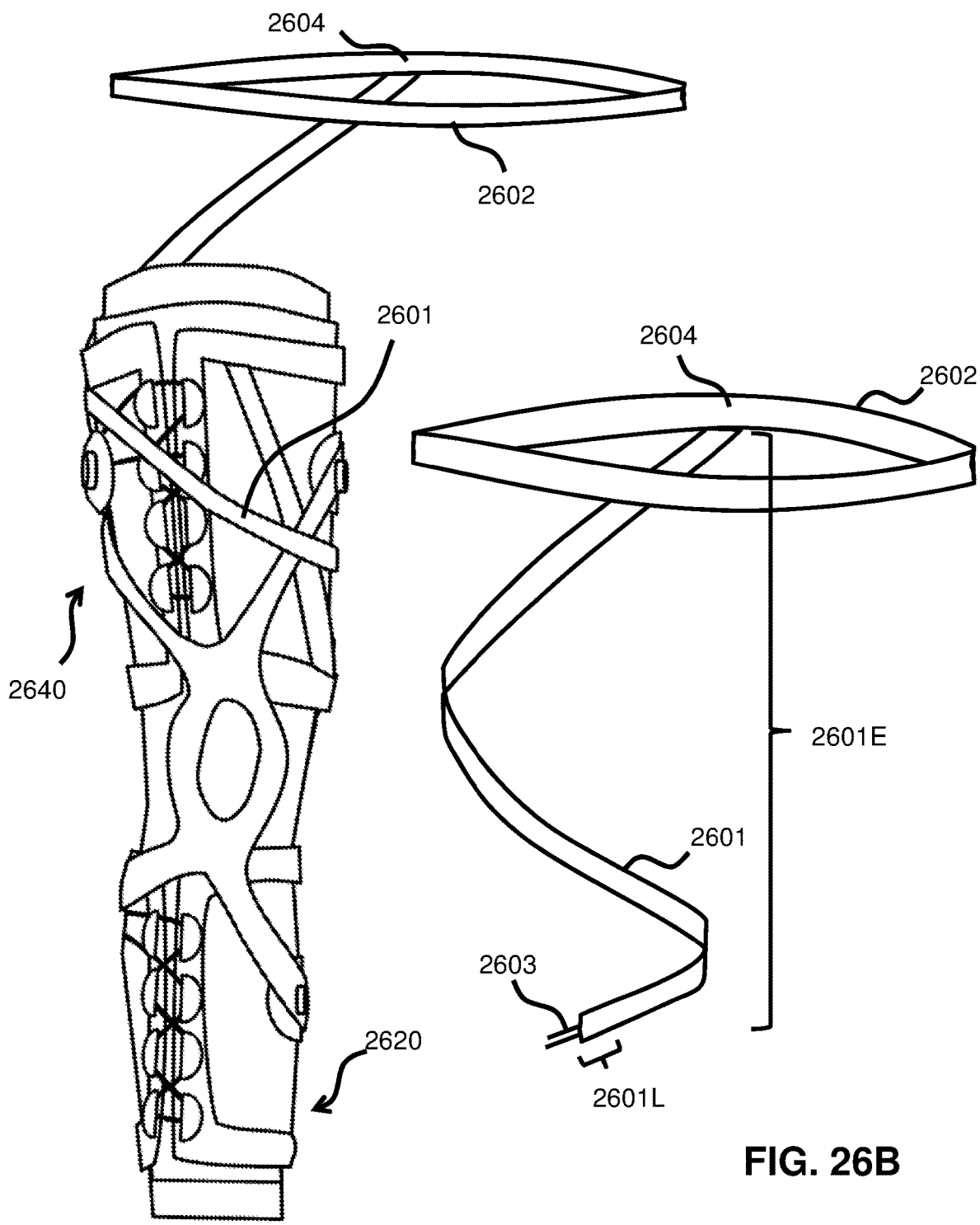
FIG. 26A shows an example embodiment of the brace assembly with a training strap.
FIG. 26B shows an example embodiment of the training strap.

FIG. 26A illustrates another example embodiment of a brace assembly with a training strap. Details of suitable training strap embodiments include those disclosed in U.S. Pat. No. 9,320,634 issued on Apr. 26, 2016, the entire content of which is herein incorporated by reference in its entirety. Generally, the elastic training strap is configured to provide a change in a resistance force on an upper and a lower training strap mounting portion when one of the training strap mounting portions is moved from a first position to a second position relative to the other training strap mounting portion whereby the change in resistance force affects the neuromuscular training of the body portion. The resistance force is applied by the elastic training strap through upper and lower resistance points on the upper and lower training strap mounting portions. Generally, the upper training strap mounting portion is positioned and secured about one side of the limb or joint and the lower training strap mounting portion is positioned and secured about the other side of the limb or joint so that the training strap can provide neuromuscular training of that body portion. The training strap mounting portions themselves, or a coupling of the training strap mounting portions to mounting facilities, may position the training strap mounting portions on each side of the limb or joint and provide the upper and lower resistance points.

Referring to FIG. 26A, the training strap 2601 is coupled to the upper mounting facility at an attachment point that may function as the lower resistance point for the training strap. The training strap 2601 is wrapped around the brace assembly and the leg up to an upper training strap mounting portion 2602 secured around the waist of the wearer. For the training strap 2601, the upper training strap portion 2602 functions as the upper training strap mounting portion of the training strap and the mounting facility 2640 functions as the lower training strap mounting portion of the training strap. The portion of the training strap 2601 between these two mounting portions comprises the elastic training strap portion (e.g. 2601E of FIG. 26B). The attachment point 2604 of the training strap 2601 to the upper training strap mounting portion 2602 functions as the upper resistance point for the training strap 2601.

FIG. 26B illustrates an embodiment of an elastic training strap that may be used with embodiments of the adjustable brace assembly without the brace assembly. The training strap 2601 has an upper training strap mounting portion 2602 configured to wrap around the wearer's waist. The elastic training strap portion 2601E of the training strap 2601 is integral with the upper training strap mounting portion 2602 or otherwise coupled at an attachment point 2604. The training strap 2601 also has a lower training strap mounting portion 2601L to couple to a mounting facility (e.g., 2640 of FIG. 26A). Cables 2603 or other means of attaching are used to attach the end of the training strap 2601 to the mounting facility. As shown in FIG. 26D, some embodiments of the training strap 2601 may have the adjusting facility comprising a tightening mechanism 2627 and cable 2624 mounted on the training strap and configured to attach to an attachment point on the mounting facility.

FIG. 26C illustrates a side view of an example embodiment with the training strap 2601 wrapped around the brace assembly with the lower end of the training strap 2601 attached by cable 2624 to an attachment point 2627 that may also be an adjusting facility. The upper end of the training strap is integral with or otherwise coupled to the upper training strap mounting portion 2602 of the training strap. Some embodiments of the brace assembly may be utilized as a hyperextension prevention brace where it may prevent hyperextension of the knee during activity, they may be used as a training brace for practice or game keeping the knee in a "athletic" position, and they may be used in sports in which braces with any metal can't be used (e.g., soccer, etc.).

In some embodiments, the proximal and distal straps may be wider than shown, about three inches (3") that wrap around the front and then attach to help hold the mounting facilities down. In some embodiments, the stabilizing straps also may be longer and wrap around the anterior of the limb and then attach to help hold the mounting facilities on the limb. In some embodiments, the elastic cross straps may be moved to the most distal position with the angle of the buckle changed to align with the direction of the strap. In some embodiments, conform tape may be used on the skin to enhance the interface with the brace.

Although not necessary, in some embodiments of the assembly, the assembly further includes a covering that can be decorative and/or can provide a sleek/smooth surface for the wearer.

One Example Embodiment of the Brace Assembly in Operation:

One example embodiment of the disclosed inventions will be used to further illustrate the operational aspects of the invention. Although the embodiment discussed utilizes an assembly embodiment with a shin shell as the lower mounting facility, it is understood that embodiments of the invention may be applied to an assembly without a shin shell. For those other embodiments, such as shown in FIG. 5, the attachment of the straps on or around the wearer's thigh in a sleeve provides many of the same functions as the upper mounting facility described below.

One example embodiment of the invention, as shown in FIGS. 1A and 1B, is used about a wearer's knee 105. The brace assembly 100 is initially secured on the wearer's shin 102. This is done by securing the shin shell 121 on the shin 102 and wrapping the securing straps 124 around the calf. This securing is done at a point of that calf such that the movement of the shell towards the knee is minimized. Once secured on the shin, the elastic cross strap arms 162 and 164 are wrapped behind or posterior to the knee creating an x-pattern as the cross origin 166 in the popliteal fossa of the knee and then wrapped anterior and around the thigh. The cross strap arms are wrapped so that one arm wraps from the lower attachment point 122 laterally, then behind the knee and then medial and upwards to the upper attachment point 142. The other arm wraps from the lower attachment point 122 medial, then behind the knee and them lateral and upward to the upper attachment point 142. Connectors 146A and 146B, such as Velcro, of the cross strap arms 162 and 164 are secured to each other forming the upper mounting facility 140. The upper arms of the cross strap are attached to matching Velcro fasteners on the cross strap such that they create facility attachment point 142 anterior on the thigh. As with the shin shell 121, the placement of the upper mounting facility 140 is done to minimize the movement of the facility towards the knee 105.

Once secured on the thigh 104 and the tibia, the presence of the elastic straps in the X configuration provides resistance to knee extension and helps prevent the knee from hyperextension. Hyperextension is prevented by the cooperation of the secured ends of the straps with the positioning of the straps behind the knee. The elastic properties of the cross strap can provide resistive properties early in the motion arch of the joint thereby help control extension early in the motion arch. As the joint extends, the elastic straps stretch and provide progressively more resistance. When the knee reaches a desired limit, the elastic straps reach a significant resistance level that prevents further extension. This resistance does not provide a hard stop of the extension. By not having a hard stop, brace migration is minimized as well as the discomfort caused by sudden jerking of the brace when the hard stop if reached. Additionally, this resistance approach uniquely provides therapeutic benefits such as increasing neuromuscular control and causing the extensor muscles to gradually strengthen which is beneficial for joint stability.

The point of attachment, facility attachment points 142 and 122, of the elastic straps and the thigh and tibial pad respectively are such that the desired resistance provided by the anterior resistance points allow proper knee movement but prevents hyperextension. Additionally, if the brace assembly 100 has good frictional contact with the skin, rotational support of the knee joint is also provided. As the wearer uses the brace assembly, and as their need for support and/or comfort changes, the elastic straps can be tightened or loosened to change the elastic tension on the system by simply removing and reattaching the straps with the Velcro attaching means.

The embodiment of FIG. 4 operates similar to FIG. 1. In this embodiment, the elastic cross strap 460 is used to function as both the lower mounting facility 420 and the upper mounting facility 440. This can start with the elastic cross strap being initially wrapped around the shin 402 of the wearer and crossing the arms around each other anterior to the shin. Once secured on the shin 402, the same methods described for FIG. 1 can be followed to mount the brace assembly on the knee. In this embodiment, the anterior resistance points are at points of the elastic cross strap at the front of the wearer's thigh and shin such as at strap attachment points 476 and 486.

The embodiment of FIG. 10 operates similar to the embodiments described for FIGS. 1 and 4.

Other Embodiments of the Brace Assembly in Operation:

The embodiments of FIGS. 2, 5 and 6 operate in a similar manner to those shown in FIGS. 1 and 4. With the embodiments of FIGS. 2, 5 and 6, the upper and lower cuff or the sleeve is mounted around the knee and the cross strap is attached to the attachment points and adjusted. The elastic cross straps can be adjusted so that the length of the upper and lower arms between the attachment points is made longer or shorter depending on the person wearing the brace assembly and the desired tension. In embodiments, the uprights can be contained within the under sleeve or other covering that connects the hinges to the upper and lower pad. The placement of the uprights maintain the relative distance between the upper and lower pad and therefore help maintain the resistance and support provided by the elastic straps.

The embodiments of FIGS. 7-9 operate similar to those in FIGS. 1 and 4. With the embodiments of FIGS. 7-9, the elastic cross strap can already be attached through the slots in the brace elements or it can be attached as part of putting the brace on by the wearer. The wearer puts their leg between the cross origin of the elastic cross strap and the portions of the elastic cross strap that become positioned on the front of the wearer's leg. The brace assembly is positioned so that the upper mounting facility is positioned above the joint and the lower mounting facility is positioned below the joint. The elastic cross strap is then adjusted with respect to the side attachment points by sliding the strap in and out of the slots. If necessary, the connectors on the end of the strap are unconnected to allow more adjustment of the strap. Once adjusted, the connectors are secured to each other so that the brace assembly is secured around the wearer's leg about the joint and provides the adequate amount of tension. If provided, the securing strap can be adjustably connected/coupled by a buckle to help further secure the brace on the wearer's leg. Once secured, the upper mounting facility is able to pivot about the hinge while the cooperation of the cross-origin with other portions of the elastic cross strap help prevent the wearer's knee from hyperextension.

The example embodiments illustrated in FIGS. 12A-12F operate in similar fashion to the embodiments already described. In this embodiment, the wearer positions a sleeve 1296 on the lower leg above the wearer's ankle joint. This may be positioned by sliding a closed sleeve (FIG. 12B) over the foot and the ankle or it may be positioned by wrapping an open sleeve (FIGS. 12A, 12D-12F) around the ankle joint and closing with closing means 1297 such as hook and loop type fasteners. The sleeve includes lower attachment points 1286 that attach two cross straps 1282A and 1282P with the sleeve medially at the lower attachment points 1286. The unattached ends of the two cross straps are then positioned about the wearer's foot and ankle. One cross strap, the anterior strap 1282A, is brought under the middle of the foot and back over the lateral ankle bone and brought behind the leg up to an upper attachment point 1276 on the sleeve on the lower leg. The upper attachment point 1276 is on a posterior or medial side of the lower leg. The other cross strap, the posterior strap 1282P, is brought under the heel of the foot, over the lateral ankle bone and brought in front of the leg up to an upper attachment point 1276 on the sleeve on the lower leg. The upper attachment point 1276 is on an anterior or medial side of the lower leg. This configuration positions the cross origin 1266 at a location on the lateral ankle bone and creates resistance points for the strap at both attachment points. To analyze the forces consistent with FIGS. 3A and 3B in this ankle joint embodiment, the upper attachment point 1276 represents the upper point of resistance, however the lower attachment point 1286 may not always define the lower point of resistance. The lower point of resistance, when the straps are frictionally engaged with the bottom of the foot, is the point where this frictional engagements starts along the strap from the cross origin such as 1286' and 1286". For embodiments with a mounting means under the foot as described earlier, the point at where this mounting means is attached to the strap may function as the point of resistance.

The embodiments of FIGS. 13A-13B start operation by positioning the frame portion 1396 on the back around the waist joint. Typically, this is positioned proximal to the lumbar area of the spine. Whether positioned already on the frame or separately, the cross strap arms 1382 and 1372 are configured on the frame such that the cross origin 1366 is positioned generally in alignment with, and in the middle of the lumbar area of the spine. In this embodiment, two cross straps extend from this cross origin, each having an upper arm 1372 and a lower arm 1382. The upper arm 1372 of a first strap extends up the torso to the right lateral side and wraps around the front of the wearer. The lower arm 1382 of the first strap extends down the torso to the left lateral side and wraps around the front of the wearer about at a waist position. The second strap has an upper arm extending up the torso to the left lateral side and wraps around the front of the wearer and the lower arm extends down the torso to the right lateral side and also wraps around the front of the wearer about at a waist position. The upper arms can be secured to each other creating the upper mounting facility 1340. The lower arms are also secured to each other creating the lower mounting facility 1320.

The embodiments of FIGS. 14A-14D utilize the cross strap to restrict the abduction and external rotation of the shoulder. This is typically configured by locating the point for the cross origin 1466 in the axillary fossa of the opposite shoulder. From this point, arms 1482 and 1472 extend across the torso and attach at attachment points 1476 and 1486 on the upper and lower mounting facilities respectively. These facilities are shown as being positioned on the upper shoulder above the joint and on the humerus below the shoulder joint. The arms of the straps are such that a continual strap extends from the upper mounting facility around the back, through the cross origin and around the front of the wearer to attach on the lower mounting facility. Another set of arms extend from the lower mounting facility around the back, through the cross origin and around the front of the wearer to attach on the upper mounting facility.

The example embodiments of FIGS. 15A-15B function similar to the knee embodiments except they are applied to the elbow joint. In these embodiments, the cross strap is configured such that the cross origin is positioned to resist extension of the radius and ulna relative to the humerus. This is typically configured by locating the point for the cross origin in the antecubital fossa of a wearer's elbow and having the cross strap arms extend up and down the arm of the wearer. As shown in the side view of FIG. 15A, the cross strap arms wrap around the upper part and the lower part of the arm such that the attachment points are on the opposite side of the arm from the antecubital fossa. In the embodiment shown, the cross strap is also wrapped around the arm to have that portion of the strap function as both the upper and the lower mounting facilities. FIG. 15B shows a front view of the elbow brace.

The embodiment shown in FIGS. 16A-16B operates similar to the other knee brace embodiments described above such as described for FIG. 2. Operationally, the cuff brace elements 1621B and 1641B as well as the hinge 1690 may be optionally provided and used to provide additional support for the brace.

The embodiments shown in FIGS. 17A-17F and FIG. 18 operate similar to the other brace embodiments described above such as described for FIG. 2.

The embodiments shown in FIGS. 19A-19F operate consistent with the brace assembly embodiments defined herein. The adjusting facilities for these embodiments may be loosened initially to allow the user to don the brace over distal limb features such as an ankle on a leg. When positioned about the joint, the adjusting facilities may be tightened to secure the brace assembly about the joint. The adjusting facilities may be donned with the brace assembly, for example when they are coupled to an inner sleeve, or they may be coupled separately and then tightened. For embodiments that also include cross straps, the tension on the cross strap may be loosened and then may be donned with an outer sleeve or they may be coupled separately to the attachment points on the brace assembly. The outer sleeve may be used over the inner sleeve and mounting facilities or it may be used separately. Once positioned properly, the adjusting facilities may be used to tighten the cross strap to a point that is comfortable for the wearer or to a point that otherwise provides the proper protection for the joint.

The embodiments shown in FIGS. 20A-20E, 21, 22A-22B, 23A-23C and 24A-24C generally operate similar to the brace assembly embodiments of FIGS. 19A-19F.

The example embodiments illustrated in FIGS. 25A-25C and 26A-26D operates consistent with those of FIGS. 1A and 1B with additional operational elements provided by enhancements such as the patella stabilizer in FIGS. 25A-25C and the training strap shown in FIGS. 26A-26D.

Referring to FIGS. 25A-25C, in operation the patella stabilizer 2595 may be mounted on the mounting facilities 2540 and 2520 after mounting facilities are donned by the wearer. The upper ends of the patella stabilizer 2595 may be attached to the upper mounting facility 2540 at attachment points 2542 and the lower ends are attached to the lower mounting facility 2520 at attachment points 2522 so that the stabilizer opening in properly positioned over the wearer's patella. Lateral attachment points may also be provide but are not shown. As shown in FIGS. 25B and 25C, adjusting facilities such as tightening mechanism 2527, cable 2524 and attachment point 2522 may be used to adjust the tension of the stabilizer on the wearer and to adjust positioning of the stabilizer.

Referring to FIGS. 26A-26D, in operation the lower end of the training strap 2601 may be attached to the mounting facility 2640 before or after it is donned. The upper end of the training strap 2602 may also be donned before or after the mounting facility 2640 is donned. Operationally, as shown in FIG. 26C (without showing the hip), the lower end of the training strap, as the lower training strap mounting portion, may be positioned on the leg of a hip joint of the wearer; the upper end of the training strap, as the upper training strap mounting portion 2602, may be positioned above the greater trochanter of the upper leg of the wearer; the upper resistance point, here attachment point 2604, is positioned posterior to and above the greater trochanter of the upper leg; and the elastic training portion of the training strap 2601 is coupled from the lower resistance point, here attachment point 2627 and the upper resistance point 2604. The lower resistance point 2627 is positioned whereby the elastic training portion of the training brace 2601 crosses from the lower resistance point 2627 to the upper resistance point 2604 in a direction at least anterior and lateral to the upper leg and below the greater trochanter of the upper leg whereby the resistance force affects an abduction of the upper leg when the leg is put in flexion.

For some embodiments, the length of the cross strap, training strap or patella stabilizer, and the tension put on the straps when attaching to the attachment points, can be varied to vary the resistance force utilizing attachment or adjusting means described earlier.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

We claim:

1. A brace assembly for use by a wearer, the brace assembly comprising:
    an upper mounting facility operably coupled to a lower mounting facility; and
    a training strap comprising:
        an upper training strap mounting portion,
        a lower training strap mounting portion coupled to the upper mounting facility at an attachment point lateral to a body portion of the wearer,
        an elastic training strap portion configured to wrap posterior, medial, anterior and lateral to the body portion and provide a change in a resistance force on the upper training strap mounting portion and the lower training strap mounting portion when one of the upper training strap mounting portion or the lower training strap mounting portion is moved from a first position to a second position relative to the other training strap mounting portion whereby the change in the resistance force affects a neuromuscular training of the body portion,
        wherein the resistance force is a progressive resistance force provided by the elastic training strap portion comprising a composite of tensile elements, and
        wherein the composite of tensile elements comprises:
            a first tensile element having a first tensile strength and a first resting length; and
            a second tensile element having a second tensile strength greater than the first tensile strength and a second resting length longer than the first resting length whereby a first resistance force is provided through a first stretch range up to the second resting length and a second resistance force is provided in a second stretch range beyond the second resting length.

2. The brace assembly of claim 1 wherein one of the upper training strap mounting portion or the lower training strap mounting portion further comprises an adjusting facility whereby the adjusting facility is configured to adjust the resistance force provided by the training strap.

3. The brace assembly of claim 2 wherein the adjusting facility comprises a cable and a tightening mechanism configured to operably couple with the training strap.

4. The brace assembly of claim 3 wherein the tightening mechanism operates as a ratchet to shorten an effective length of the cable.

5. The brace assembly of claim 1 further comprising:
    at least one elastic cross strap coupled to the upper mounting facility and the lower mounting facility; and
    the at least one elastic cross strap further forming a cross origin between the upper mounting facility and the lower mounting facility whereby the at least one elastic cross strap is configured to provide a second resistance force to an extension of the upper mounting facility and the lower mounting facility from the cross origin when the cross origin is positioned in a fossa of a wearer's joint.

6. The brace assembly of claim 5 further comprising a second adjusting facility whereby the second adjusting facility is configured to adjust an inside radius of the upper mounting facility or the lower mounting facility.

7. The brace assembly of claim 5 further comprising a second adjusting facility whereby the second adjusting facility is configured to adjust an effective length of the at least one elastic cross strap whereby the second adjusting facility adjusts the second resistance force.

8. The brace assembly of claim 2 wherein the adjusting facility comprises an attachment point of the training strap to the upper mounting facility.

9. The brace assembly of claim 1 wherein the resistance force is a configurable resistance force.

10. The brace assembly of claim 1 further comprising a patella stabilizer operably coupled to an upper attachment point on the upper mounting facility and a lower attachment point on the lower mounting facility.

11. A brace assembly for use by a wearer, the brace assembly comprising:
- an upper mounting facility operably coupled to a lower mounting facility; and
- a training strap comprising:
  - an upper training strap mounting portion,
  - a lower training strap mounting portion coupled to the upper mounting facility, and
  - an elastic training strap portion configured to provide a change in a resistance force on the upper training strap mounting portion and the lower training strap mounting portion when one of the upper training strap mounting portion or the lower training strap mounting portion is moved from a first position to a second position relative to the other training strap mounting portion whereby the change in the resistance force affects a neuromuscular training of a body portion;
- wherein the resistance force is a progressive resistance force provided by the elastic training strap portion comprising a composite of tensile elements; and
- wherein the composite of tensile elements comprises:
  - a first tensile element having a first tensile strength and a first resting length, and
  - a second tensile element having a second tensile strength greater than the first tensile strength and a second resting length longer than the first resting length whereby a first resistance force is provided through a first stretch range up to the second resting length and a second resistance force is provided in a second stretch range beyond the second resting length.

12. The brace assembly of claim 11 wherein the upper training strap mounting portion is configured to be mounted to a mounting facility about a waist of the wearer and the lower training strap mounting portion is configured to be coupled to the upper mounting facility of a joint brace.

13. The brace assembly of claim 11 wherein the upper training strap mounting portion is a portion of the training strap and the lower training strap mounting portion is a portion of the training strap.

14. The brace assembly of claim 11 wherein:
the body portion comprises an upper leg of the wearer; and
the progressive resistance force is configured to provide progressively more resistance force as the upper leg is moved from a raised position to an extended position.

* * * * *